United States Patent
Pratt et al.

(10) Patent No.: US 12,209,278 B2
(45) Date of Patent: *Jan. 28, 2025

(54) ACCELERATED SEQUENCING METHODS

(71) Applicant: Ultima Genomics, Inc., Newark, CA (US)

(72) Inventors: Mark Pratt, Bozeman, MT (US); Gilad Almogy, Palo Alto, CA (US); Dumitru Brinza, Montara, CA (US); Eliane Trepagnier, Oakland, CA (US); Omer Barad, Mazkeret Batya (IL); Yoav Etzioni, Tel Aviv (IL); Florian Oberstrass, Menlo Park, CA (US)

(73) Assignee: Ultima Genomics, Inc., Fremont, CA (US)

( * ) Notice: Subject to any disclaimer, the term of this patent is extended or adjusted under 35 U.S.C. 154(b) by 223 days.

This patent is subject to a terminal disclaimer.

(21) Appl. No.: 17/822,760

(22) Filed: Aug. 26, 2022

(65) Prior Publication Data

US 2023/0060685 A1    Mar. 2, 2023

Related U.S. Application Data

(63) Continuation of application No. 17/453,481, filed on Nov. 3, 2021, now Pat. No. 11,459,609, which is a continuation of application No. PCT/US2020/031163, filed on May 1, 2020.

(60) Provisional application No. 62/971,530, filed on Feb. 7, 2020, provisional application No. 62/904,274, filed on Sep. 23, 2019, provisional application No. 62/842,534, filed on May 3, 2019.

(51) Int. Cl.
| | | |
|---|---|---|
| *C12Q 1/68* | (2018.01) | |
| *C12Q 1/6827* | (2018.01) | |
| *C12Q 1/6869* | (2018.01) | |
| *G16B 30/00* | (2019.01) | |

(52) U.S. Cl.
CPC ......... *C12Q 1/6869* (2013.01); *C12Q 1/6827* (2013.01); *G16B 30/00* (2019.02)

(58) Field of Classification Search
CPC .. C12Q 1/6823; C12Q 1/6869; C12Q 1/6876; C12Q 1/6827; G16B 30/00
See application file for complete search history.

(56) References Cited

U.S. PATENT DOCUMENTS

| | | |
|---|---|---|
| 5,714,320 A | 2/1998 | Kool |
| 8,364,417 B2 | 1/2013 | Chen |
| 8,772,473 B2 | 7/2014 | Huang |
| 9,428,807 B2 | 8/2016 | Hubbell |
| 9,587,274 B2 | 3/2017 | Chen |
| 9,817,944 B2 | 11/2017 | Kural |
| 10,192,024 B2 | 1/2019 | Chen |
| 10,344,328 B2 | 7/2019 | Barbee |
| 11,220,709 B2 | 1/2022 | Oberstrass et al. |
| 11,220,710 B2 | 1/2022 | Oberstrass et al. |
| 11,459,609 B2 | 10/2022 | Pratt et al. |
| 11,462,300 B2 | 10/2022 | Bartov et al. |
| 11,578,363 B2 | 2/2023 | Oberstrass et al. |
| 11,763,915 B2 | 9/2023 | Etzioni et al. |
| 2009/0053724 A1 | 2/2009 | Roth |
| 2010/0093986 A1 | 4/2010 | Zwick et al. |
| 2010/0173303 A1 | 7/2010 | Ronaghi et al. |
| 2011/0270533 A1 | 11/2011 | Zhang |
| 2012/0252682 A1 | 10/2012 | Zhou |
| 2013/0090860 A1 | 4/2013 | Sikora |
| 2013/0281306 A1 | 10/2013 | Rigatti et al. |
| 2014/0052381 A1 | 2/2014 | Utiramerur |
| 2014/0315724 A1 | 10/2014 | Zhou |
| 2015/0066824 A1 | 3/2015 | Harris |
| 2015/0203910 A1 | 7/2015 | Smith et al. |
| 2016/0110499 A1 | 4/2016 | Donnet |
| 2016/0326579 A1 | 11/2016 | Olejnik |

(Continued)

FOREIGN PATENT DOCUMENTS

| | | |
|---|---|---|
| CN | 101415839 A | 4/2009 |
| CN | 103717753 A | 4/2014 |

(Continued)

OTHER PUBLICATIONS

Ali, M.M. et al. (2014). "Rolling Circle Amplification: A Versatile Tool For Chemical Biology, Materials Science and Medicine," Chem. Soc. Rev. 43:3324, 19 pages.

Chaisson, M.J. et al. (2009). "De Novo Fragment Assembly With Short Mate Paired Reads: Does The Read Length Matter?," Genome Research 19:336-346.

Dean et al. (2001). "Rapid Amplification Of Plasmid And Phage DNA Using Phi29 DNA Polymerase And Multiply-Primed Rolling Circle Amplification," Genome Research 11:1095-1099.

Depristo, M.A. et al. (May 2011, e-pub. Apr. 10, 2011). "A Framework For Variation Discovery And Genotyping Using Next-Generation DNA Sequencing Data," Nature Genetics 43(5):491-498, 20 pages.

(Continued)

*Primary Examiner* — Jezia Riley
(74) *Attorney, Agent, or Firm* — MORRISON & FOERSTER LLP

(57) ABSTRACT

Described herein are methods of generating a coupled sequencing read pair for a polynucleotide, and methods of analyzing the coupled sequencing read pair. The coupled sequencing read pair can be analyzed to detect polynucleotide variants, including at loci that are not directly sequenced within the coupled sequencing read pair. Other analytical methods can include using coupled sequencing read pairs to construct or validate a consensus sequence. The coupled sequencing read pair may be generated for a polynucleotide by generating sequencing data for a first region by extending a primer using labeled nucleotides; further extending the primer through a second region using nucleotides provided in a second region flow order, wherein primer extension through the second region is faster than primer extension through the first region; and generating sequencing data associated with a sequence of a third region of the polynucleotide by further extending the primer using labeled nucleotides.

19 Claims, 30 Drawing Sheets

Specification includes a Sequence Listing.

(56) References Cited

U.S. PATENT DOCUMENTS

| | | |
|---|---|---|
| 2017/0044601 A1 | 2/2017 | Crnogorac |
| 2017/0335387 A1 | 11/2017 | Brinza |
| 2018/0330051 A1 | 11/2018 | Hubbell |
| 2018/0363047 A1 | 12/2018 | Smith |
| 2019/0360034 A1 | 11/2019 | Zhou et al. |
| 2020/0199666 A1 | 6/2020 | Gatti-Lafranconi et al. |
| 2020/0372971 A1 | 11/2020 | Etzioni |
| 2020/0377937 A1 | 12/2020 | Pratt |
| 2020/0392584 A1 | 12/2020 | Almogy |
| 2021/0010075 A1 | 1/2021 | Oberstrass |
| 2021/0054442 A1 | 2/2021 | Pratt et al. |
| 2021/0147930 A1 | 5/2021 | Oberstrass et al. |
| 2021/0147931 A1 | 5/2021 | Oberstrass et al. |
| 2021/0366576 A1 | 11/2021 | Bartov et al. |
| 2022/0170089 A1 | 6/2022 | Pratt et al. |
| 2023/0197197 A1 | 6/2023 | Bartov et al. |
| 2023/0313289 A1 | 10/2023 | Oberstrass et al. |
| 2023/0343416 A1 | 10/2023 | Etzioni et al. |
| 2023/0407385 A1 | 12/2023 | Barad |
| 2024/0018599 A1 | 1/2024 | Barad |
| 2024/0043918 A1 | 2/2024 | Barad |
| 2024/0120025 A1 | 4/2024 | Etzioni |
| 2024/0287483 A1 | 8/2024 | Mazur |

FOREIGN PATENT DOCUMENTS

| | | |
|---|---|---|
| CN | 103917654 A | 7/2014 |
| JP | 2001517948 A | 10/2001 |
| WO | 199844151 A1 | 10/1998 |
| WO | 199844152 A1 | 10/1998 |
| WO | 2012134602 A2 | 10/2012 |
| WO | 2012166742 A2 | 12/2012 |
| WO | 2012166742 A3 | 4/2013 |
| WO | 2012134602 A3 | 12/2013 |
| WO | 2019084158 A1 | 5/2019 |
| WO | 2019099886 A1 | 5/2019 |
| WO | 2019191003 A1 | 10/2019 |
| WO | 2020172197 A1 | 8/2020 |
| WO | 2020185790 A1 | 9/2020 |
| WO | 2020186243 A1 | 9/2020 |
| WO | 2020227137 A1 | 11/2020 |
| WO | 2020236630 A1 | 11/2020 |
| WO | 2020240025 A1 | 12/2020 |
| WO | 2021007495 A1 | 1/2021 |
| WO | 2022051296 A1 | 3/2022 |
| WO | 2022056296 A1 | 3/2022 |
| WO | 2022099270 A1 | 5/2022 |
| WO | 2022099271 A1 | 5/2022 |
| WO | 2022109574 A1 | 5/2022 |
| WO | 2022204685 A1 | 9/2022 |
| WO | 2023004421 A1 | 1/2023 |
| WO | 2023288319 A1 | 1/2023 |
| WO | 2023010069 A1 | 2/2023 |
| WO | 2023010131 A1 | 2/2023 |
| WO | 2023060091 A1 | 4/2023 |
| WO | 2023081653 A1 | 5/2023 |
| WO | 2023081883 A2 | 5/2023 |
| WO | 2023081883 A3 | 6/2023 |
| WO | 2023141430 A1 | 7/2023 |
| WO | 2023164505 A2 | 8/2023 |
| WO | 2023164505 A3 | 10/2023 |
| WO | 2024102889 A1 | 5/2024 |

OTHER PUBLICATIONS

Hwang, S. et al. (Dec. 7, 2015). "Systematic Comparison Of Variant Calling Pipelines Using Gold Standard Personal Exome Variants," Sci Rep. 5(17875):1-8.

International Preliminary Report on Patentability, issued Nov. 2, 2021, for International Patent Application No. PCT/US20/31163, filed May 1, 2020, 12 pages.

International Search Report and Written Opinion of the Searching Authority mailed Oct. 9, 2020, for International Patent Application No. PCT/US20/31163, filed May 1, 2020, 18 pages.

Invitation to Pay Additional Fees mailed Aug. 3, 2020, for Patent Application No. PCT/US20/31163, filed May 1, 2020, 2 pages.

Mielczarek, M. et al. (2016). "Review Of Alignment And SNP Calling Algorithms For Next-Generation Sequencing Data," J. Appl. Genetics 57:71-79.

Miller, J.R. et al. (2010, e-pub. Mar. 6, 2010). "Assembly Algorithms For Next-Generation Sequencing Data," Genomics 95:315-327.

Nielsen, R. et al. (Jun. 2011). "Genotype And SNP Calling From Next-Generation Sequencing Data," Nature Reviews Genetics 12(6):443-451, 20 pages.

Peng, Q. et al. (2019, e-pub. Mar. 18, 2019). "Targeted Single Primer Enrichment Sequencing with Single End Duplex-UMI," Scientific Reports 9(4810):1-10.

Poplin, R. et al. (Jul. 24, 2018, e-pub. Nov. 14, 2017). "Scaling Accurate Genetic Variant Discovery To Tens Of Thousands Of Samples," BioRxiv, located at https://www.biorxiv.org/content/biorxiv/early/2017/11/14/201178.1.full.pdf, last visited on Aug. 7, 2020, 22 pages.

Zerbino, D.R. et al. (2008, e-pub. Mar. 18, 2008). "Velvet: Algorithms For De Novo Short Read Assembly Using De Bruijn Graphs," Genome Research 18:821-829.

Zook, J. M. et al. (Apr. 1, 2019). "An Open Resource For Accurately Benchmarking Small Variant And Reference Calls," Nature Biotechnology 37:561-566, 14 pages.

Mitra, R.B. et al. (2003). "Fluorescent in Situ Sequencing on Polymerase Colonies," Analytical Biochemistry 320:55-65.

Somervuo, P. et al. (2018). "BARCOSEL: A Tool for Selecting an Optimal Barcode Set for High-Throughput Sequencing," BMC Bioinformatics 19:257, 6 pages.

U.S. Appl. No. 18/281,930, filed Sep. 13, 2023, by Oberstrass et al. (U.S. Patent Application is not submitted herewith pursuant to the waiver of 37 C.F.R. § 1.98(a)(2)(iii) issued by the Office on Sep. 21, 2004).

U.S. Appl. No. 18/651,565, filed Apr. 30, 2024, by Mazur et al. (U.S. Patent Application is not submitted herewith pursuant to the waiver of 37 C.F.R. § 1.98(a)(2)(iii) issued by the Office on Sep. 21, 2004).

Van Dijk, E.L. et al. (2018). "The Third Revolution in Sequencing Technology," Trends in Genetics 34(9):666-681.

TATGGTCGTCGA       R1
TGGTCGTCGAGC       R2
TATATGGTCGTC       R3
―――――――――――――――――
TATATGGTCATCGAGCTAT   H1
TATATGGTCGTCGAGCTAT   H2
                    ↑

FIG. 15A

R1 Sequencing Data Set

| Base Count | Cycle 1 | | | | Cycle 2 | | | | Cycle 3 | | | | Cycle 4 | | | | Cycle 5 | | | |
|---|---|---|---|---|---|---|---|---|---|---|---|---|---|---|---|---|---|---|---|---|
| | 1 T | 2 A | 3 C | 4 G | 5 T | 6 A | 7 C | 8 G | 9 T | 10 A | 11 C | 12 G | 13 T | 14 A | 15 C | 16 G | 17 T | 18 A | 19 C | 20 G |
| 0 | 0.0010 | 0.0010 | 0.9998 | 0.9998 | 0.0010 | 0.9998 | 0.9998 | 0.0001 | 0.0010 | 0.9998 | 0.0010 | 0.0010 | 0.0010 | 0.9998 | 0.0010 | 0.0010 | 0.9998 | 0.0010 | 0.9998 | 0.9998 |
| 1 | 0.9979 | 0.9979 | 0.0010 | 0.0010 | 0.9979 | 0.0010 | 0.0010 | 0.0010 | 0.9979 | 0.0010 | 0.9979 | 0.9979 | 0.9979 | 0.0010 | 0.9979 | 0.9979 | 0.0010 | 0.9979 | 0.0010 | 0.0010 |
| 2 | 0.0010 | 0.0010 | 0.0001 | 0.0001 | 0.0010 | 0.0001 | 0.0001 | 0.9979 | 0.0010 | 0.0001 | 0.0010 | 0.0010 | 0.0010 | 0.0001 | 0.0010 | 0.0010 | 0.0001 | 0.0010 | 0.0001 | 0.0001 |
| 3 | 0.0001 | 0.0001 | 0.0001 | 0.0001 | 0.0001 | 0.0001 | 0.0001 | 0.0010 | 0.0001 | 0.0001 | 0.0001 | 0.0001 | 0.0001 | 0.0001 | 0.0001 | 0.0001 | 0.0001 | 0.0001 | 0.0001 | 0.0001 |

| Base Count | Cycle 1 | | | | | Cycle 2 | | | | | Cycle 3 | | | | | Cycle 4 | | | | | Cycle 5 | | | | |
|---|---|---|---|---|---|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 | 20 |
| | T | A | C | G | T | A | C | G | T | A | C | G | T | A | C | G | T | A | C | G |
| 0 | 0.0010 | 0.0010 | 0.9988 | 0.9988 | 0.0010 | 0.9988 | 0.9988 | 0.0001 | 0.0010 | 0.9988 | 0.0010 | 0.0010 | 0.9988 | 0.0010 | 0.9988 | 0.9988 | 0.0010 | 0.9988 | 0.0010 | 0.0010 |
| 1 | 0.9979 | 0.9979 | 0.0010 | 0.0010 | 0.9979 | 0.0010 | 0.0010 | 0.0010 | 0.9979 | 0.0010 | 0.9979 | 0.9979 | 0.0010 | 0.9979 | 0.0010 | 0.0010 | 0.9979 | 0.0010 | 0.9979 | 0.9979 |
| 2 | 0.0010 | 0.0010 | 0.0001 | 0.0001 | 0.0010 | 0.0001 | 0.0001 | 0.9979 | 0.0010 | 0.0001 | 0.0010 | 0.0010 | 0.0001 | 0.0010 | 0.0001 | 0.0001 | 0.0010 | 0.0001 | 0.0010 | 0.0010 |
| 3 | 0.0001 | 0.0001 | 0.0001 | 0.0001 | 0.0001 | 0.0001 | 0.0001 | 0.0010 | 0.0001 | 0.0001 | 0.0001 | 0.0001 | 0.0001 | 0.0001 | 0.0001 | 0.0001 | 0.0001 | 0.0001 | 0.0001 | 0.0001 |

FIG. 16

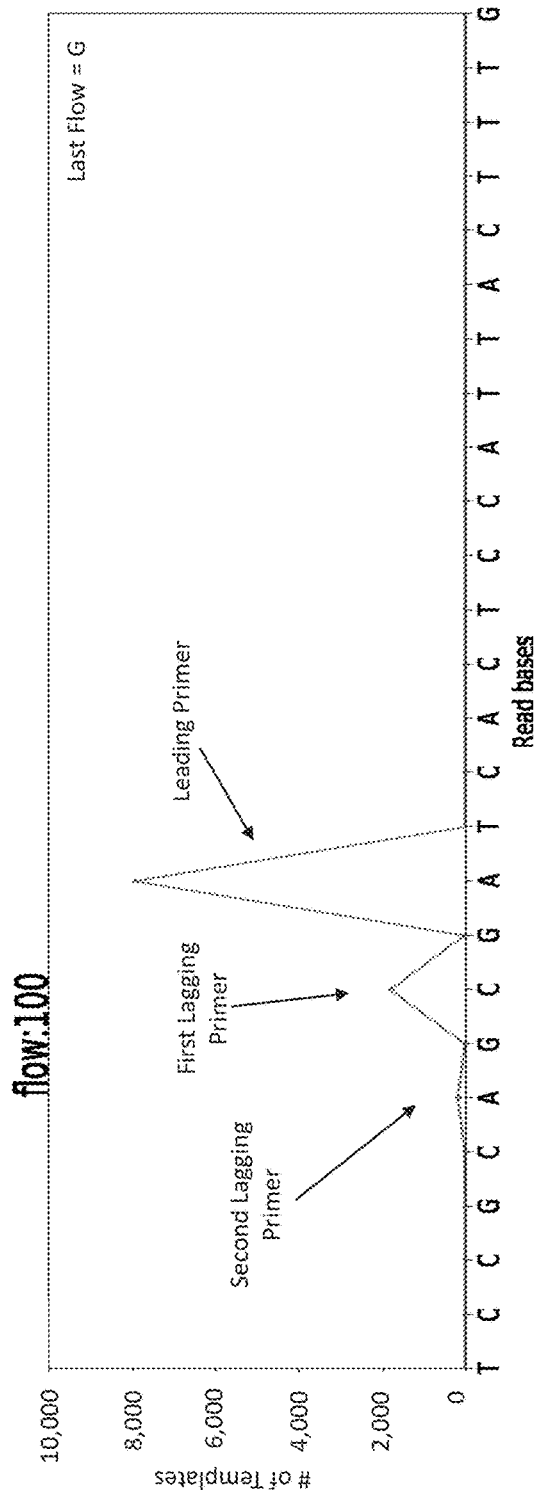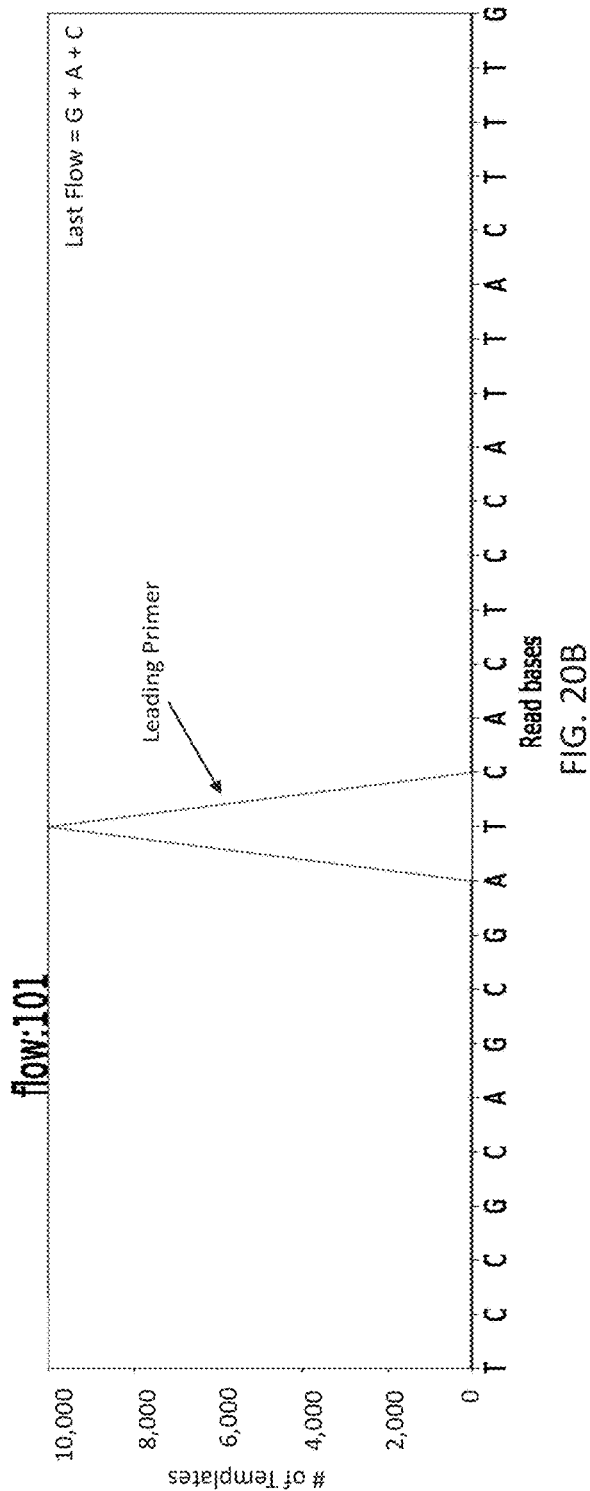
FIG. 20A
FIG. 20B

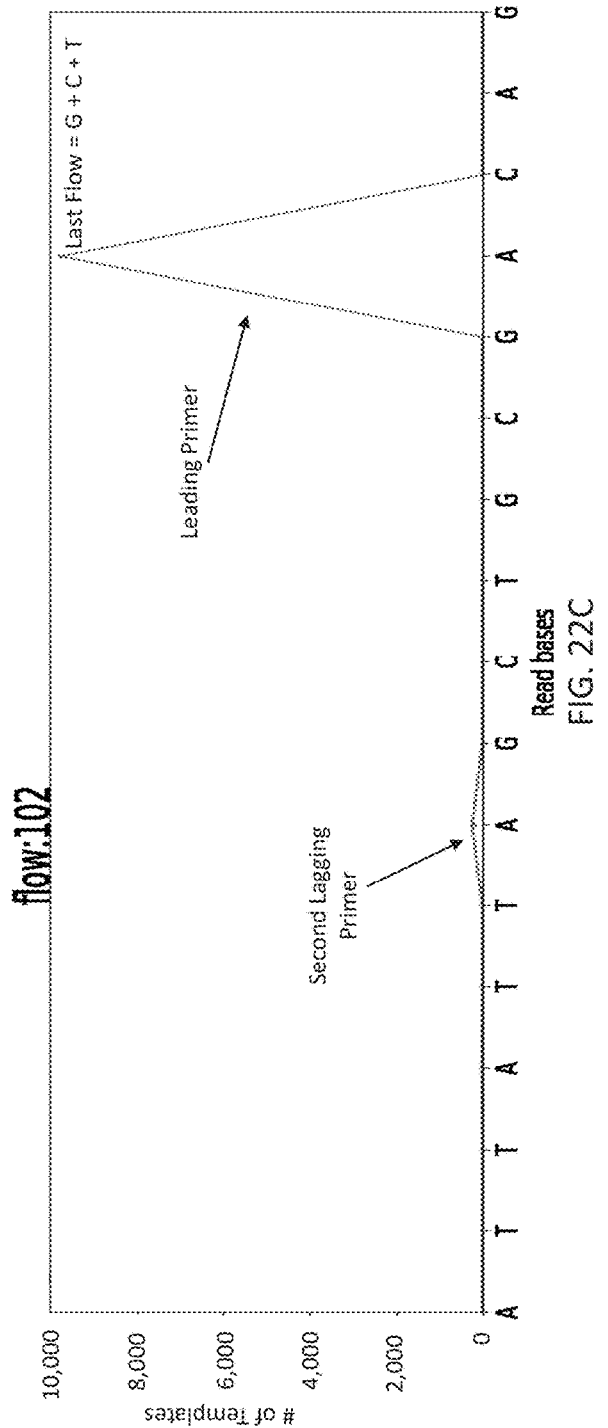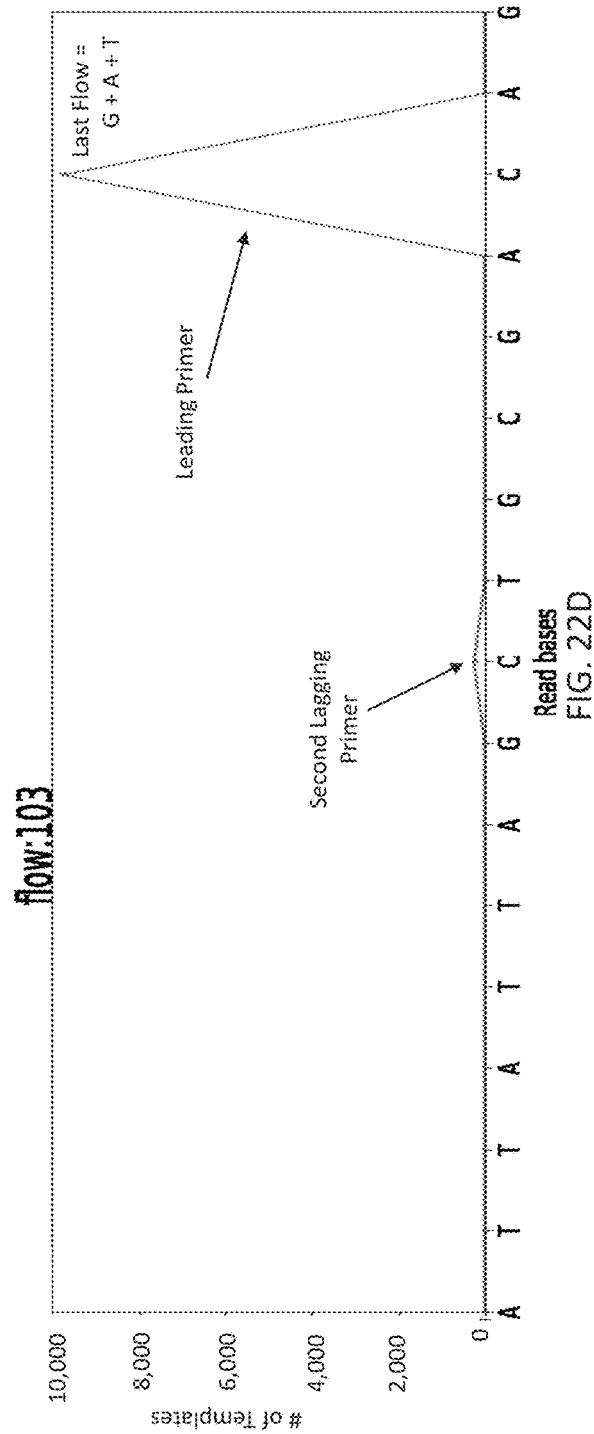

ACCELERATED SEQUENCING METHODS

CROSS-REFERENCE TO RELATED APPLICATIONS

This application is a continuation of U.S. patent application Ser. No. 17/453,481, filed Nov. 3, 2021; which is a continuation International application of PCT/US2020/031163, filed on May 1, 2020; which claims the priority benefit U.S. Provisional Application No. 62/971,530, filed Feb. 7, 2020, U.S. Provisional Application No. 62/904,274, filed Sep. 23, 2019, and U.S. Provisional Application No. 62/842,534, filed May 3, 2019; the content of each of which is incorporated herein by reference in its entirety.

REFERENCE TO AN ELECTRONIC SEQUENCE LISTING

The content of the electronic sequence listing (165272000403SEQLIST.xml; Size: 19,198 bytes; and Date of Creation: Aug. 25, 2022) is herein incorporated by reference in its entirety.

FIELD OF THE INVENTION

Described herein are methods of sequencing a polynucleotide, including methods for generating a coupled sequencing read pair, and methods of analyzing sequencing data obtained from the sequencing methods.

BACKGROUND

Paired-end sequencing methods have been used to obtain sequencing data for the 3' and 5' ends of a polynucleotide molecule. Generally, a sequencing primer is hybridized to a DNA polynucleotide to be sequenced, and several bases are sequenced to obtain sequencing data for the first end of the polynucleotide. A second sequencing primer is then hybridized to the complementary strand near the other end of the polynucleotide, and sequenced to determine sequencing data of the other end of the polynucleotide. The sequencing data for the 3' and 5' ends of the polynucleotide are coupled based on the fact that the sequencing data was obtained from the same sequencing cluster. Paired-end sequencing methods are frequently used in next-generation sequencing (NGS) protocols.

Using traditional paired-end sequencing, however, no (or very little) information is derived for the region between the 3' and 5' ends of a polynucleotide. Although the paired end sequencing data can be used for certain analytical purposes, it cannot be used to detect certain variants in the unsequenced region of the polynucleotide. Certain long-range sequencing techniques have been developed to sequence the region of the polynucleotide generally missed using traditional paired-end sequencing methods. However, long-range sequencing is relatively slow and prone to substantial sequencing errors.

BRIEF SUMMARY OF THE INVENTION

Described herein are methods of sequencing a polynucleotide, including methods for generating a coupled sequencing read pair, and methods of analyzing sequencing data obtained from the sequencing methods.

A method for generating a coupled sequencing read pair from a polynucleotide comprises (a) hybridizing the polynucleotide to a primer to form a hybridized template; (b) generating sequencing data associated with a sequence of a first region of the polynucleotide by extending the primer using labeled nucleotides, and detecting the presence or absence of an incorporated labeled nucleotide; (c) further extending the primer extended in step (b) through a second region using nucleotides provided in a second region flow order, wherein (i) the primer is extended through the second region without detecting the presence or absence of a label of a nucleotide incorporated into the extending primer, (ii) a mixture of at least two different types of nucleotide bases are used in at least one step of the second region flow order, or (iii) extension of the primer through the second region proceeds faster than the extension of the primer in step (b); and (d) generating sequencing data associated with a sequence of a third region of the polynucleotide by further extending the primer extended in step (c) using labeled nucleotides, and detecting the presence or absence of an incorporated labeled nucleotide. In some embodiments, extension of the primer through the second region proceeds faster than the extension of the primer in step (b). In some embodiments, the method of generating the coupled sequencing read pair comprises associating the sequencing data of the first region with the sequencing data of the third region.

In some embodiments, a method of generating a coupled sequencing read pair from a polynucleotide, comprises (a) hybridizing a primer to a first region of the polynucleotide to form a hybridized template; (b) extending the primer through a second region using nucleotides provided in a second region flow order, wherein (i) the primer is extended through the second region without detecting the presence or absence of a label of a nucleotide incorporated into the extending primer, or (ii) a mixture of at least two different types of nucleotide bases are used in at least one step of the second region flow order; and (c) generating sequencing data associated with a sequence of a third region of the polynucleotide by further extending the primer extended in step (b) using labeled nucleotides, and detecting the presence or absence of an incorporated labeled nucleotide. In some embodiments, the first region comprises a naturally occurring sequence targeted by the primer.

In some embodiments, the primer is extended through the second region without detecting the presence or absence of a label of a nucleotide incorporated into the extending primer. In some embodiments, at least a portion of the nucleotides used to extend the primer through the second region are unlabeled nucleotides. In some embodiments, the nucleotides used to extend the primer through the second region are unlabeled nucleotides.

In some embodiments, a mixture of at least two different types of nucleotide bases are used in at least one step of the second region flow order.

In some embodiments of the method of generating the coupled sequencing read pair, the second region flow order comprises five or more nucleotide flows. In some embodiments, each of the nucleotide flows comprises a single nucleotide base. In some embodiments, the second region flow order induces a signal change at more than two flow positions for 50% or more of possible SNP permutations at 5% or more of random sequencing start positions. In some embodiments, the induced signal change is a change in signal intensity, or a new substantially zero (or new zero) or a new substantially non-zero (or new non-zero) signal. In some embodiments, the induced signal change is a new substantially zero (or new zero) or a new substantially non-zero (or new non-zero) signal. In some embodiments, the second region flow order has an efficiency of 0.6 or more base incorporations per flow.

In some embodiments, the method of generating the coupled sequencing read pair comprises determining expected sequencing data for the second region using a reference sequence and the second region flow order. In some embodiments, the primer is extended through the third region using nucleotides provided in a third region flow order, and the method further comprises determining expected sequencing data for the third region using a reference sequence for the second region, the second region flow order, the third region flow order, and a reference sequence for the third region. In some embodiments, the third region flow order comprises five or more nucleotide flows. In some embodiments, each of the nucleotide flows comprises a single nucleotide base. In some embodiments, the third region flow order induces a signal change at more than two flow positions for 50% or more of possible SNP permutations at 5% or more of random sequencing start positions. In some embodiments, the induced signal change is a change in signal intensity, or a new substantially zero (or new zero) or a new substantially non-zero (or new non-zero) signal. In some embodiments, the induced signal change is a new substantially zero (or new zero) or a new substantially non-zero (or new non-zero) signal. In some embodiments, the third region flow order has an efficiency of 0.6 or more base incorporations per flow.

In some embodiments of the method of generating the coupled sequencing read pair, the primer is extended through the third region using nucleotides provided in a third region flow order, the method further comprising determining expected sequencing data for the third region using a reference sequence for the second region, the second region flow order, the third region flow order, and sequencing data associated with the sequence of the third region, wherein the sequencing data associated with the sequence of the third region is the same or different sequencing data generated for the third region. In some embodiments, the expected reference data for the second region or the third region comprises a binary or non-binary flowgram. IN some embodiments, the method further comprises determining expected test variant sequencing data for the second region using the second region flow order and a second reference sequence for the second region, wherein the second reference sequence comprises the test variant. In some embodiments, the primer is extended through the third region using nucleotides provided in a third region flow order, and the method further comprises determining expected test variant sequencing data for the third region using the second reference sequence for the second region, the second region flow order, the third region flow order, and a reference sequence for the third region. In some embodiments, the primer is extended through the third region using nucleotides provided in a third region flow order, and the method further comprises determining expected test variant sequencing data for the third region using the second reference sequence for the second region, the second region flow order, the third region flow order, and sequencing data associated with the sequence of the third region, wherein the sequencing data associated with the sequence of the third region is the same or different sequencing data generated for the third region. In some embodiments, the expected reference sequencing data for the second region or the third region comprises a binary or non-binary flowgram.

In some embodiments, the method of generating the coupled sequencing read pair comprises determining expected sequencing data for the second region using a reference sequence and the second region flow order. In some embodiments, the primer extended in step (d) is extended using nucleotides provided in a third region flow order, and the method further comprises determining expected sequencing data for the third region using a reference sequence for the second region, the second region flow order, the third region flow order, and a reference sequence for the third region. In some embodiments, the primer extended in step (d) is extended using nucleotides provided in a third region flow order, and the method further comprises determining expected sequencing data for the third region using a reference sequence for the second region, the second region flow order, the third region flow order, and sequencing data associated with the sequence of the third region, wherein the sequencing data associated with the sequence of the third region is the same or different sequencing data generated in step (d). In some embodiments, the expected reference data for the second region or the third region comprises a binary or non-binary flowgram. In some embodiments, the method comprises determining expected test variant sequencing data for the second region using the second region flow order and a second reference sequence for the second region, wherein the second reference sequence comprises the test variant. In some embodiments, the primer extended in step (d) is extended using nucleotides provided in a third region flow order, and the method further comprises determining expected test variant sequencing data for the third region using the second reference sequence for the second region, the second region flow order, the third region flow order, and a reference sequence for the third region. In some embodiments, the primer extended in step (d) is extended using nucleotides provided in a third region flow order, and the method further comprises determining expected test variant sequencing data for the third region using the second reference sequence for the second region, the second region flow order, the third region flow order, and sequencing data associated with the sequence of the third region, wherein the sequencing data associated with the sequence of the third region is the same or different sequencing data generated in step (d). In some embodiments, the expected reference sequencing data for the second region or the third region comprises a binary or non-binary flowgram.

In some embodiments, generating the coupled sequencing read pair further comprises: (e) further extending the primer extended in step (d) through a fourth region using nucleotides provided in a fourth region flow order, wherein (i) the primer is extended through the fourth region without detecting the presence or absence of a label of a nucleotide incorporated into the extending primer, (ii) a mixture of at least two different types of nucleotide bases are used in at least one step of the fourth region flow order, or (iii) extension of the primer through the fourth region proceeds faster than the extension of the primer in step (b) or step (d); and (0 generating sequencing data associated with a sequence of a fifth region of the polynucleotide by further extending the primer extended in step (e) using labeled nucleotides, and detecting the presence or absence of an incorporated labeled nucleotide. In some embodiments, the method further comprises associating the sequencing data of the fifth region with the sequencing data of the first region or the sequencing data of the third region.

Also described herein is a method of mapping a coupled sequencing read pair to a reference sequence, comprising: mapping a first region or portion thereof, or a third region or portion thereof, of a coupled sequencing read to a reference sequence; and mapping the unmapped first region or portion thereof, or the unmapped third region or portion thereof, to the reference sequence using distance information indicative of the length of the second region.

Further provided is a method of detecting a structural variant, comprising mapping a first region or portion thereof, or a third region or portion thereof, of a coupled sequencing read pair to a reference sequence; determining an expected locus within a reference sequence for the unmapped first region or portion thereof, or the unmapped third region or portion thereof, using distance information indicative of the length of the second region; determining expected sequencing data for a sequence at the expected locus based on the reference sequence; and detecting the structural variant by comparing the sequencing data of the unmapped first region or portion thereof, or the unmapped third region or portion thereof, to the expected sequencing data, wherein a difference between the sequencing data of the unmapped first region or portion thereof, or the unmapped third region or portion thereof, and the expected sequencing data indicates the structural variant.

Also provided herein is a method of detecting a structural variant, comprising mapping a first region or portion thereof or a third region or portion thereof, of a coupled sequencing read pair to a reference sequence, wherein the unmapped first region, or the unmapped third region, is unmappable within the reference sequence. In some embodiments, the method further comprises determining a locus of the structural variant within the reference sequence based on an expected distance information indicative of the length of the second region.

In some embodiments, the unmapped first region or portion thereof, or the unmapped third region or portion thereof, is within an insertion relative to the reference sequence. In some embodiments, the unmapped first region or portion thereof, or the unmapped third region or portion thereof, bridges the start or end of an insertion relative to the reference sequence.

Further provided herein is a method of detecting a structural variant, comprising mapping a first region or portion thereof and a third region or portion thereof, of a coupled sequencing read pair to a reference sequence; determining a mapped distance information between the mapped first region and the mapped third region; and detecting the structural variant by comparing the mapped distance information to an expected distance information of the second region, wherein a difference between the mapped distance information and the expected distance information indicates the structural variant. In some embodiments, the structural variant is a chromosomal fusion, an inversion, an insertion, or a deletion. In some embodiments, the variant is an insertion or deletion within the second region.

In some embodiments of the methods described herein, the distance information is determined using information associated with the second region flow order and a probability distribution of bases in the second region. In some embodiments, the information associated with the second region flow order is a number different types of nucleotide bases simultaneously used to extend the primer in step (c). In some embodiments, the probability distribution of bases in the second region is determined from the distribution of bases within the genome.

In some embodiments of the methods described herein, distance information is derived from expected sequencing data for the second region determined using a reference sequence and the second region flow order. In some embodiments, the expected sequencing data comprises a binary or non-binary flowgram.

Further described herein is a method of mapping a coupled sequencing read pair to a reference sequence, comprising: mapping a first region or portion thereof and a third region or portion thereof of a coupled sequencing read pair to a reference sequence at two or more different position pairs comprising a first position and a second position; and selecting a correct position pair using first distance information indicative of the length of the second region and second distance information indicative of the distances between the first position and the second position for the two or more position pairs. In some embodiments, the first distance information is determined using information associated with the second region flow order and a probability distribution of bases in the second region. In some embodiments, the information associated with the second region flow order is a number different types of nucleotide bases simultaneously used to extend the primer in step (c). In some embodiments, the probability distribution of bases in the second region is determined from the distribution of bases within the genome. In some embodiments, the first distance information is derived from expected sequencing data for the second region determined using a reference sequence and the second region flow order. In some embodiments, the expected reference sequencing data comprises a binary or non-binary flowgram.

Also described herein is a method of detecting a variant between two sequenced regions of a coupled sequencing read pair generated according to any above the above methods, wherein the primer extended in step (d) is extended using nucleotides provided in a third region flow order, comprising: mapping the first region or portion thereof to a reference sequence; determining expected sequencing data for the third region or portion thereof using (1) a reference sequence for the second region, the second region flow order, the third region flow order, and a reference sequence for the third region, or (2) a reference sequence for the second region, the second region flow order, the third region flow order, and generated sequencing data associated with the sequence of the third region, wherein the generated sequence data associated with the sequence of the third region is the same or different sequence data generated in step (d); and detecting the presence of a variant by comparing the expected sequencing data for the third region to the generated sequencing data associated with the sequence of the third region. In some embodiments, the variant is a structural variant. In some embodiments, the structural variant is a chromosomal fusion, an inversion, an insertion, or a deletion. In some embodiments, the variant is a single nucleotide polymorphism (SNP). In some embodiments, the method is used to detect a test variant, and the reference sequence comprises the test variant. In some embodiments, the test variant is selected by identifying the test variant within a second polynucleotide. In some embodiments, the method further comprises associating the detected test variant with an allele sequenced in the first region or the third region of the polynucleotide.

Also described herein is a method of detecting a variant between two sequenced regions of a coupled sequencing read pair generated according to any of the method described above, wherein the primer extended is extended through the third region using nucleotides provided in a third region flow order, comprising: mapping the first region or portion thereof to a reference sequence; determining expected sequencing data for the third region or portion thereof using (1) a reference sequence for the second region, the second region flow order, the third region flow order, and a reference sequence for the third region, or (2) a reference sequence for the second region, the second region flow order, the third region flow order, and generated sequencing data associated with the sequence of the third region, wherein the generated sequence data associated with the sequence of the third region is the same or different sequence data generated for the third region; and detecting the presence of a variant by comparing the expected sequencing data for the third region to the generated sequencing data associated with the sequence of the third region. In some embodiments, the variant is a structural variant. In some embodiments, the structural variant is a chromosomal fusion, an inversion, an insertion, or a deletion. In some embodiments, the variant is a single nucleotide polymorphism (SNP). In some embodiments, the method is used to detect a test variant, and the reference sequence comprises the test variant. In some embodiments, the test variant is selected by identifying the test variant within a second polynucleotide. In some embodiments, the method comprises associating the detected test variant with an allele sequenced in the first region or the third region of the polynucleotide.

Further described herein is a method of generating a coupled sequencing read pair for detecting the presence of a base transversion in an unsequenced region of a polynucleotide, comprising: (a) hybridizing the polynucleotide to a primer to form a hybridized template; (b) generating sequencing data associated with a sequence of a first region of the polynucleotide by extending the primer using labeled nucleotides, and detecting the presence or absence of an incorporated labeled nucleotide; (c) further extending the primer extended in step (b) through a second region using a flow order comprising alternating nucleotide pairs of (1) cytosine and thymine, and (2) adenine and guanine; and (d) generating sequencing data associated with a sequence of a third region of the polynucleotide by further extending the primer extended in step (c) using labeled nucleotides, and detecting the presence or absence of an incorporated labeled nucleotide. In some embodiments, the primer is extended through the second region without detecting the presence or absence of a label of a nucleotide incorporated into the extending primer.

Also described herein is a method of generating a coupled sequencing read pair from a polynucleotide, comprising: (a) hybridizing a primer to a first region of the polynucleotide to form a hybridized template; (b) extending the primer through a second region using a flow order comprising alternating nucleotide pairs of (1) cytosine and thymine, and (2) adenine and guanine; and (c) generating sequencing data associated with a sequence of a third region of the polynucleotide by further extending the primer extended in step (b) using labeled nucleotides, and detecting the presence or absence of an incorporated labeled nucleotide. In some embodiments, the first region comprises a naturally occurring sequence targeted by the primer. In some embodiments, the primer is extended through the second region without detecting the presence or absence of a label of a nucleotide incorporated into the extending primer.

In some embodiments, a method of detecting the presence of a base transversion in an unsequenced region of a polynucleotide comprises: mapping a first region or portion thereof, and a third region or a portion thereof, of a coupled sequencing read pair generated according to the methods described above, wherein the primer extended in step (d) is extended using nucleotides provided in a third region flow order, to a reference sequence; determining expected sequencing data for the third region using the second region flow order, the third region flow order, and the reference sequence; and detecting the presence of the base transversion based on the difference between expected sequencing data for the third region and the generated sequencing data for the third region. In some embodiments, the expected sequencing data for the third region is determined using the second region flow order, the third region flow order, the reference sequence for the second region, and the reference sequence for the third region. In some embodiments, the expected sequencing data for the third region is determined using the second region flow order, the third region flow order, the reference sequence for the second region, and generated sequence data associated with the sequence of the third region, wherein the generated sequence data associated with the sequence of the third region is the same or different sequence data generated in step (d). In some embodiments, the expected sequencing data for the third region comprises a binary or non-binary flowgram.

Further described herein is a method of generating one or more consensus sequences, comprising assembling a plurality of coupled sequencing read pairs. In some embodiments, the one or more consensus sequences are assembled using distance information indicative of the length of the second region of the plurality of coupled sequencing read pairs. In some embodiments, the distance information is determined using information associated with the second region flow order and a probability distribution of bases in the second region. In some embodiments, the information associated with the second region flow order is a number different types of nucleotide bases simultaneously used to extend the primer in step (c). In some embodiments, the probability distribution of bases in the second region is determined from the distribution of bases within the genome. In some embodiments, the distance information is derived from expected reference sequencing data for the second region determined using a reference sequence and the second region flow order. In some embodiments, the expected reference sequencing data comprises a binary or non-binary flowgram.

In some embodiments, the method of generating one or more consensus sequences further comprises validating a portion of a consensus sequence selected from the one or more consensus sequences using a selected coupled sequencing read associated with the portion of the selected consensus sequence, wherein the primer extended in step (d) when generating the selected coupled sequencing read is extended using nucleotides provided in a third region flow order, the validating comprising: determining expected sequencing data for the third region of the selected coupled sequencing read using the second region flow order, the third region flow order, and the portion of the selected consensus sequence; and validating the portion of the selected consensus sequence by comparing the expected sequencing data for the third region of the selected coupled sequencing read to the generated sequencing data of the third region.

Also described is a method of validating a status of a test variant, comprising: comparing a status of the variant across a plurality of overlapping coupled sequencing read pairs, the plurality of overlapping coupled sequencing read pairs comprising a locus corresponding to a locus of the test variant; validating the status of the variant of based on the comparison. In some embodiments, the first region or the third region of the selected coupled sequencing read overlaps with the second region of at least a portion of other coupled sequencing reads in the plurality of overlapping coupled sequencing reads. In some embodiments, the variant status of the selected coupled sequencing read indicates a variant in the first region or the third region of the selected coupled sequencing read. In some embodiments, the second region of the selected coupled sequencing read overlaps with the second region of at least a portion of other coupled sequencing reads in the plurality of overlapping coupled sequencing reads. In some embodiments, the variant status of the selected coupled sequencing read indicates a variant in the second region of the selected coupled sequencing read.

Further described herein is a method for detecting a short genetic variant in a test sample, comprising: generating a coupled sequencing read pair according to any of the above methods; comparing the sequencing data associated with a sequence of third region of the polynucleotide to expected sequencing data for an expected sequence of the third region of the polynucleotide; and calling the presence or absence of the short genetic variant in the second region of the polynucleotide. In some embodiments, comparing the sequencing data associated with the sequence of the third region of the polynucleotide to an expected sequencing data for the third region of the polynucleotide comprises determining a match score indicative of a likelihood that the sequencing data generated for the third region of the polynucleotide matches the expected sequencing data for the third region of the polynucleotide; and calling the calling the presence or absence of the target short genetic variant in the second region of the polynucleotide comprises using the determined match score. In some embodiments, the expected sequencing data for the third region of the polynucleotide is obtained by sequencing and expected sequence of the third region of the polynucleotide in silico. In some embodiments, the sequencing data associated with the sequence of the first region or the sequencing data associated with the sequence of the third region comprises flow signals representing a base count indicative of a number of bases incorporated at each flow position within a plurality of flow positions. In some embodiments, the flow signals comprise a statistical parameter indicative of a base count likelihood for at least one base count at each flow position. In some embodiments, the flow signals comprises a statistical parameter indicative of a base count likelihood for a plurality of base counts at each flow position. In some embodiments, the sequencing data associated with the sequence of the third region comprises flow signals representing a base count indicative of a number of bases incorporated at each flow position within a plurality of flow positions, wherein the flow signals comprise a statistical parameter indicative of a base count likelihood for a plurality of base counts; and the method further comprises selecting the statistical parameter at each flow position in the sequencing data that corresponds with a base count of the expected sequence at that flow position, and determining a match score indicative of the likelihood that the sequencing data set matches the expected sequence. In some embodiments, the match score is a combined value of the selected statistical parameters across the flow positions in the sequencing data.

In some embodiments of the above methods, the flow-cycle order comprises four separate flows repeated in the same order.

In some embodiments of the above methods, the flow-cycle order comprises five or more separate flows.

In some embodiments of the above methods, generating the coupled sequencing read pair further comprises: further extending the primer through a fourth region using nucleotides provided in a fourth region flow order, wherein (i) the primer is extended through the fourth region without detecting the presence or absence of a label of a nucleotide incorporated into the extending primer, (ii) a mixture of at least two different types of nucleotide bases are used in at least one step of the fourth region flow order, or (iii) extension of the primer through the fourth region proceeds faster than the extension of the primer through the first region or the third region; and generating sequencing data associated with a sequence of a fifth region of the polynucleotide by further extending the primer extended through the fourth using labeled nucleotides, and detecting the presence or absence of an incorporated labeled nucleotide. In some embodiments, the method further comprises associating the sequencing data of the fifth region with the sequencing data of the first region or the sequencing data of the third region.

In some embodiments of the above methods, the polynucleotide is amplified using rolling circle amplification.

Also described herein is a method of detecting a short genetic variant in a test sample, comprising: (a) amplifying a polynucleotide using rolling circle amplification (RCA) to generate a RCA-amplified polynucleotide comprising at least a first copy of the polynucleotide and a second copy of the polynucleotide; (b) hybridizing the RCA-amplified polynucleotide to a primer to form a hybridized template; (c) generating sequencing data associated with a sequence of a first region of the polynucleotide within the first copy of the polynucleotide by extending the primer using labeled nucleotides, and detecting the presence or absence of an incorporated labeled nucleotide; (d) further extending the primer through a second region of the polynucleotide within the first copy of the polynucleotide using nucleotides provided in a second region flow order, wherein (i) the primer is extended through the second region of the polynucleotide within the first copy of the polynucleotide without detecting the presence or absence of a label of a nucleotide incorporated into the extending primer, (ii) a mixture of at least two different types of nucleotide bases are used in at least one step of the second region flow order, or (iii) extension of the primer through the second region of the polynucleotide within the first copy of the polynucleotide proceeds faster than the extension of the primer through the first region; (e) generating sequencing data associated with a sequence of a third region of the polynucleotide by further extending the primer using labeled nucleotides, and detecting the presence or absence of an incorporated labeled nucleotide; (f) comparing the sequencing data generated for the third region of the polynucleotide to expected sequencing data for an expected sequence of the third region of the polynucleotide; (g) calling the presence of the short genetic variant in the second region of the polynucleotide; (h) generating sequencing data associated with a sequence of the second region of the polynucleotide within the second copy of the polynucleotide by extending the primer using labeled nucleotides, and detecting the presence or absence of an incorporated labeled nucleotide; and (i) calling the identity of the short genetic variant in the second region of the polynucleotide. In some embodiments, extension of the primer through the second region of the polynucleotide within the first copy of the polynucleotide proceeds faster than the extension of the primer through the first region of the polynucleotide within the first copy of the polynucleotide. In some embodiments, the sequencing data associated with the sequence of the second region of polynucleotide within the second copy of the polynucleotide is dynamically generated based on calling the presence of the short genetic variant in the second region of the polynucleotide. In some embodiments, the primer is extended through the second region of the polynucleotide within the first copy of the polynucleotide without detecting the presence or absence of a label of a nucleotide incorporated into the extending primer. In some embodiments, at least a portion of the nucleotides used to extend the primer through the second region of the polynucleotide within the first copy of the polynucleotide are unlabeled nucleotides. In some embodiments, the nucleotides used to extend the primer through the second region of the polynucleotide within the first copy of the polynucleotide are unlabeled nucleotides. In some embodiments, a mixture of at least two different types of nucleotide bases are used in at least one step of the second region flow order. In some embodiments, a mixture of three different types of nucleotide bases are used in at least one step of the second region flow order.

Further described herein is a method of detecting a short genetic variant in a test sample, comprising: (a) amplifying a polynucleotide using rolling circle amplification (RCA) to generate a RCA-amplified polynucleotide comprising at least a first copy of the polynucleotide and a second copy of the polynucleotide; (b) hybridizing a primer to a first region of the polynucleotide within the first copy of the polynucleotide to form a hybridized template; (c) extending the primer through a second region of the polynucleotide within the first copy of the polynucleotide using nucleotides provided in a second region flow order, wherein (i) the primer is extended through the second region of the polynucleotide within the first copy of the polynucleotide without detecting the presence or absence of a label of a nucleotide incorporated into the extending primer, or (ii) a mixture of at least two different types of nucleotide bases are used in at least one step of the second region flow order; (d) generating sequencing data associated with a sequence of a third region of the polynucleotide by further extending the primer using labeled nucleotides, and detecting the presence or absence of an incorporated labeled nucleotide; (e) comparing the sequencing data generated for the third region of the polynucleotide to expected sequencing data for an expected sequence of the third region of the polynucleotide; (f) calling the presence of the short genetic variant in the second region of the polynucleotide; (g) generating sequencing data associated with a sequence of the second region of the polynucleotide within the second copy of the polynucleotide by extending the primer using labeled nucleotides, and detecting the presence or absence of an incorporated labeled nucleotide; and (h) calling the identity of the short genetic variant in the second region of the polynucleotide. In some embodiments, the first region comprises a naturally occurring sequence targeted by the primer. In some embodiments, the sequencing data associated with the sequence of the second region of polynucleotide within the second copy of the polynucleotide is dynamically generated based on calling the presence of the short genetic variant in the second region of the polynucleotide. In some embodiments, the primer is extended through the second region of the polynucleotide within the first copy of the polynucleotide without detecting the presence or absence of a label of a nucleotide incorporated into the extending primer. In some embodiments, at least a portion of the nucleotides used to extend the primer through the second region of the polynucleotide within the first copy of the polynucleotide are unlabeled nucleotides. In some embodiments, the nucleotides used to extend the primer through the second region of the polynucleotide within the first copy of the polynucleotide are unlabeled nucleotides. In some embodiments, a mixture of at least two different types of nucleotide bases are used in at least one step of the second region flow order. In some embodiments, a mixture of three different types of nucleotide bases are used in at least one step of the second region flow order.

Also described herein is a method of synchronizing sequencing primers within a sequencing cluster, comprising: (a) hybridizing primers to polynucleotide copies within a sequencing cluster; (b) extending the primers through a first region of the polynucleotide copies using labeled nucleotides according to a first region flow cycle; (c) extending the primers through a second region of the polynucleotide copies using one or more re-phasing flows, wherein a mixture of at least two different types of nucleotide bases are used in at least one of the one or more re-phasing flows; and (d) extending the primers through a third region of the polynucleotide copies using labeled nucleotides according to a third region flow cycle. In some embodiments, a mixture of three different types of nucleotide bases are used in at least one of the one or more re-phasing flows. In some embodiments, the one or more re-phasing flows comprise four or more flow steps. In some embodiments, the one or more re-phasing flows comprises, in any order: (i) a first flow comprising a mixture comprising A, C, and G nucleotides and omitting T nucleotides; (ii) a second flow comprising a mixture comprising T, C, and G nucleotides and omitting A nucleotides; (iii) a third flow comprising a mixture comprising T, A, and G nucleotides and omitting C nucleotides; and (iv) a fourth flow comprising a mixture comprising T, A, and C nucleotides and omitting G nucleotides. In some embodiments, the method comprises generating sequencing data associated with a sequence of the first region by detecting the presence or absence of an incorporated labeled nucleotide while extending the primers through the first region. In some embodiments, the method comprises generating sequencing data associated with a sequence of the third region by detecting the presence or absence of an incorporated labeled nucleotide while extending the primers through the third region.

Also described herein is a system, comprising one or more processors; and a non-transitory storage medium comprising one or more programs executable by the one or more processors to receive information related to one or more coupled sequencing reads; and perform any one or more of the above methods.

BRIEF DESCRIPTION OF THE DRAWINGS

FIG. 14A shows sequencing data obtained by extending a primer with a sequence of 5'-TATGGTCGTCGA-3' (SEQ ID NO: 15) using a repeated flow-cycle order of T-A-C-G. The sequencing data is representative of the extended primer strand, and sequencing information for the complementary template strand can be readily determined is effectively equivalent. FIG. 14B shows the sequencing data shown in FIG. 14A with the most likely sequence, given the sequencing data, selected based on the highest likelihood at each flow position (as indicated by stars). FIG. 14C shows the sequencing data shown in FIG. 14A with traces representing two different candidate sequences (each represented by their complement): TATGGTCATCGA (SEQ ID NO: 16) (closed circles) and TATGGTCGTCGA (SEQ ID NO: 15) (open circles). The likelihood that the sequencing data matches a given sequence can be determined as the product of the likelihood that each flow position matches the candidate sequence.

FIG. 15A shows an alignment of sequencing reads R1 (SEQ ID NO: 15), R2 (SEQ ID NO: 17), and R3 (SEQ ID NO: 18) (each represented by the sequence of an extended primer) aligned with two candidate sequences H1 (SEQ ID NO: 19) and H2 (SEQ ID NO: 20) (each represented by their complement). FIG. 15B shows sequencing data corresponding to R1 with traces representing H1 (closed circles) an H2 (open circles). FIG. 15C shows sequencing data corresponding to R2 with traces representing H1 (closed circles) an H2 (open circles). FIG. 15D shows sequencing data corresponding to R3 with traces representing H1 (closed circles) an H2 (open circles).

FIG. 16 shows sequencing data from a hypothetical nucleic acid molecule sequenced using a A-T-G-C flow cycle order. Traces can be generated using potential haplotype sequences (each represented by their complement) TATGGTCG-TCGA (SEQ ID NO: 21) (H1) and TATGGTCGATCG (SEQ ID NO: 22) (H2), with H1 having a 1 base deletion relative to H2. The sequencing data has a better match to the H2 candidate sequence, and no indel is called in this sequence.

FIG. 20A-20E shows the number of primers extended against identical polynucleotide templates in an exemplary simulated sequencing protocol after 100 nucleotide flows (FIG. 20A), and re-phasing flows designed to synchronize primers within a sequencing cluster. The illustrated re-phasing flow order is a four-step order that includes nucleotide flow 101 (FIG. 20B), flow 102 (FIG. 20C), flow 103 (FIG. 20D), and flow 104 (FIG. 20E).

FIG. 22A-22E shows the number of primers extended against identical polynucleotide templates in another exemplary simulated sequencing protocol after 100 nucleotide flows (FIG. 22A), and re-phasing flows designed to synchronize primers within a sequencing cluster. The illustrated re-phasing flow cycle is a four-step order that includes nucleotide flow 101 (FIG. 22B), flow 102 (FIG. 22C), flow 103 (FIG. 22D), and flow 104 (FIG. 22E).

In FIG. 23, the x-axis indicates the fraction of the flow phases (or fragmentation start positions), and the y-axis indicates the fraction of SNP permutations having induced a signal change (i.e., a new zero or new non-zero signal) at more than two flow positions.

DETAILED DESCRIPTION OF THE INVENTION

Figure 1:
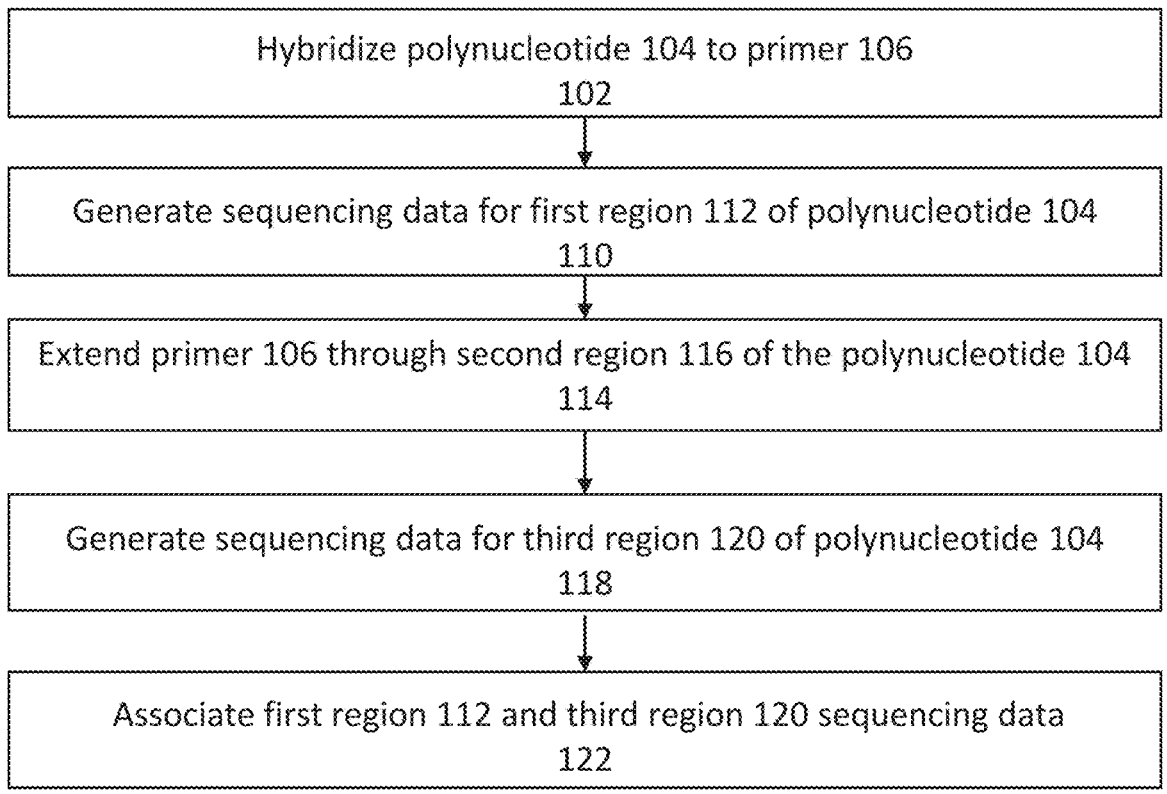
FIG. 1 illustrates a schematic of an exemplary method for generating a coupled sequencing read pair from a polynucleotide.
Figure 1:
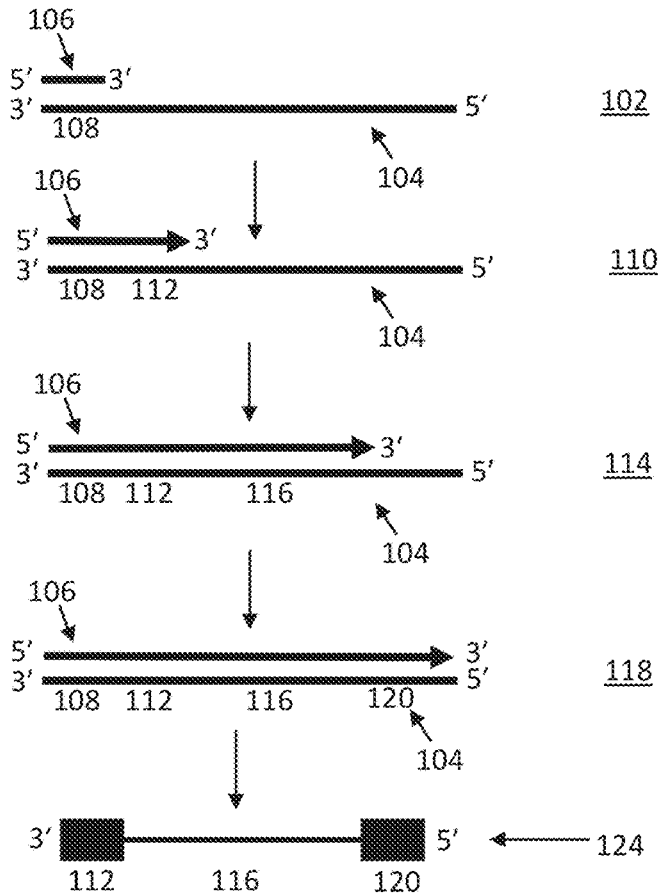

Described herein are methods of generating a coupled sequencing read pair from a polynucleotide, and methods of analyzing such a coupled sequencing read pair. The coupled sequencing read pair may be analyzed, for example, to map the coupled sequencing read pair to a reference sequence, to detect a structural variant, to detect a variant (such as a SNP) in a region between the coupled paired ends of a polynucleotide, to detect a transversion, or to determine or validate a consensus sequence.

The polynucleotide can be hybridized to a sequencing primer, which is extended through a first region (i.e., the 3' end) of the polynucleotide to sequence the first region. The primer is then extended through a second region of the polynucleotide, which may occur at a faster rate than the extension of the primer through the first region. The accelerated primer extension through the second region may be referred to as "fast forward sequencing." As further discussed herein, because the primer is extended through the second region (rather than the second region being completely skipped by the primer, as what occurs in more traditional paired-end sequencing), some information (potentially including some sequencing data) may be derived for the second region even though the second region is not sequenced in the same manner as the first region. For example, the primer may be extended through the second region using only unlabeled nucleotides. Once the sequencing primer is extended through the second region, the primer is extended into the third region (i.e., the 5' end) of the polynucleotide to sequence the third region. The sequencing data of the region and the third region can be coupled, resulting in a coupled sequencing read pair for the polynucleotide, and, as further described herein, and additional sequencing data can be derived from the second region.

In one example, a coupled sequencing read pair from a polynucleotide can be generated by (a) hybridizing the polynucleotide to a primer to form a hybridized template; (b) generating sequencing data associated with a sequence of a first region of the polynucleotide by extending the primer using labeled nucleotides, and detecting the presence or absence of an incorporated labeled nucleotide; (c) further extending the primer extended in step (b) through a second region using nucleotides provided in a second region flow order, wherein extension of the primer through the second region proceeds faster than the extension of the primer in step (b); and (d) generating sequencing data associated with a sequence of a third region of the polynucleotide by further extending the primer extended in step (c) using labeled nucleotides, and detecting the presence or absence of an incorporated labeled nucleotide. The sequencing data of the first region can be associated with the sequencing data of the third region, which indicates the coupled sequencing read pair. Nucleotides used to extend the primer through the second region may be unlabeled.

In some embodiments, a coupled sequencing read pair from a polynucleotide can be generated by (a) hybridizing the polynucleotide to a primer to form a hybridized template; (b) generating sequencing data associated with a sequence of a first region of the polynucleotide by extending the primer using labeled nucleotides, and detecting the presence or absence of an incorporated labeled nucleotide; (c) further extending the primer extended in step (b) through a second region using nucleotides provided in a second region flow order, wherein the primer is extended through the second region without detecting the presence or absence of a label of a nucleotide incorporated into the extending primer; and (d) generating sequencing data associated with a sequence of a third region of the polynucleotide by further extending the primer extended in step (c) using labeled nucleotides, and detecting the presence or absence of an incorporated labeled nucleotide. The sequencing data of the first region can be associated with the sequencing data of the third region, which indicates the coupled sequencing read pair. Nucleotides used to extend the primer through the second region may be unlabeled.

In some embodiments, a coupled sequencing read pair from a polynucleotide can be generated by (a) hybridizing the polynucleotide to a primer to form a hybridized template; (b) generating sequencing data associated with a sequence of a first region of the polynucleotide by extending the primer using labeled nucleotides, and detecting the presence or absence of an incorporated labeled nucleotide; (c) further extending the primer extended in step (b) through a second region using nucleotides provided in a second region flow order, wherein a mixture of at least two different types of nucleotide bases are used in at least one step of the flow order; and (d) generating sequencing data associated with a sequence of a third region of the polynucleotide by further extending the primer extended in step (c) using labeled nucleotides, and detecting the presence or absence of an incorporated labeled nucleotide. The sequencing data of the first region can be associated with the sequencing data of the third region, which indicates the coupled sequencing read pair. Nucleotides used to extend the primer through the second region may be unlabeled.

In some embodiments, the primer is extended through a second region to re-phase (i.e., synchronize) a plurality of sequencing reactions within a sequencing cluster. The chemical process of incorporating nucleotides into an extending prime is often imperfect, causing desynchronization among strands within a sequencing cluster. Desynchronization may result in signal degradation, and therefore reduced accuracy, when detecting the presence or absence of nucleotide incorporation into the extending primer as the read length increases. Resynchronization can result in counteracting the signal loss, which allows for a longer effective read length. To re-phase the sequencing reaction, the primer is extended through the second region using a re-phasing cycle wherein a mixture of at least two (e.g., two or three) different types of nucleotide bases are used in a plurality of steps of the second region flow order. The nucleotides incorporated during the re-phasing cycle may not be detected in some embodiments, which would result in a gap in the resulting read. However, this read gap can be managed when the sequences are aligned to a reference or other sequence.

A reference sequence can be used to extract sequencing data for the second region even though the second region may not have been sequenced directly or completely. For example, sequencing data may be obtained from the first region and/or the third region of the polynucleotide by detecting the presence or absence of a labeled nucleotide incorporated into the extending primer. However, the primer may be extended through the second region using unlabeled nucleotides or without detecting the presence or absence of an incorporated nucleotide. Using unlabeled nucleotides (or by not allowing a sequencing system time to detect an incorporated label) allows for faster primer extension through the second region, but does not allow for the direct determination of sequencing data. However, because the primer is extended through the second region using nucleotides provided in predetermined flow order, variants in the second region can affect the sequencing data determined within the third region. The reference sequence can be used to determine expected sequencing data (for example, an expected flowgram), which is compared to the generated sequencing data (such as a detected flowgram) to detect variants, including variants within the second region. The comparison between the expected sequencing information (e.g., the expected flowgram) and the generated sequencing data (e.g., the generated flowgram) can be performed in the third region (to detect variants in the second region). This methodology provide significant advantage over traditional paired-end sequencing methods, for which sequencing data for the 3' end or the 5' end of the polynucleotide are not affected by variants in the polynucleotide between the 3' end and the 5' end of the polynucleotide.

Definitions

As used herein, the singular forms "a," "an," and "the" include the plural reference unless the context clearly dictates otherwise.

Reference to "about" a value or parameter herein includes (and describes) variations that are directed to that value or parameter per se. For example, description referring to "about X" includes description of "X".

"Expected sequencing data" refers to sequencing data one would expect if the sequence of a polynucleotide used to generate a coupled sequencing read pair, or the sequence of a region of said polynucleotide, matches a reference sequence.

A "flow order" refers to the order of separate nucleotide flows used to sequence a nucleic acid molecule using non-terminating nucleotides. The flow order may be divided into cycles of repeating units, and the flow order of the repeating units is termed a "flow-cycle order." A "flow position" refers to the sequential position of a given separate nucleotide flow during the sequencing process.

The terms "individual," "patient," and "subject" are used synonymously, and refers to an animal including a human.

The term "label," as used herein, refers to a detectable moiety that is coupled to or may be coupled to another moiety, for example, a nucleotide or nucleotide analog. The label can emit a signal or alter a signal delivered to the label so that the presence or absence of the label can be detected. In some cases, coupling may be via a linker, which may be cleavable, such as photo-cleavable (e.g., cleavable under ultra-violet light), chemically-cleavable (e.g., via a reducing agent, such as dithiothreitol (DTT), tris(2-carboxyethyl) phosphine (TCEP)) or enzymatically cleavable (e.g., via an esterase, lipase, peptidase, or protease). In some embodiments, the label is a fluorophore.

A "non-terminating nucleotide" is a nucleic acid moiety that can be attached to a 3' end of a polynucleotide using a polymerase or transcriptase, and that can have another non-terminating nucleic acid attached to it using a polymerase or transcriptase without the need to remove a protecting group or reversible terminator from the nucleotide. Naturally occurring nucleic acids are a type of non-terminating nucleic acid. Non-terminating nucleic acids may be labeled or unlabeled.

A "short genetic variant" is used herein to describe a genetic polymorph (i.e., mutation) 10 consecutive bases in length or less (i.e., 10, 9, 8, 7, 6, 5, 4, 3, 2, or 1 base(s) in length). The term includes single nucleotide polymorphisms (SNPs), multi-nucleotide polymorphisms (MNPs), and indels 10 consecutive bases in length or less.

It is understood that aspects and variations of the invention described herein include "consisting" and/or "consisting essentially of" aspects and variations.

When a range of values is provided, it is to be understood that each intervening value between the upper and lower limit of that range, and any other stated or intervening value in that states range, is encompassed within the scope of the present disclosure. Where the stated range includes upper or lower limits, ranges excluding either of those included limits are also included in the present disclosure.

Some of the analytical methods described herein include mapping sequences to a reference sequence, determining sequence information, and/or analyzing sequence information. It is well understood in the art that complementary sequences can be readily determined and/or analyzed, and that the description provided herein encompasses analytical methods performed in reference to a complementary sequence.

The section headings used herein are for organization purposes only and are not to be construed as limiting the subject matter described. The description is presented to enable one of ordinary skill in the art to make and use the invention and is provided in the context of a patent application and its requirements. Various modifications to the described embodiments will be readily apparent to those persons skilled in the art and the generic principles herein may be applied to other embodiments. Thus, the present invention is not intended to be limited to the embodiment shown but is to be accorded the widest scope consistent with the principles and features described herein.

The figures illustrate processes according to various embodiments. In the exemplary processes, some blocks are, optionally, combined, the order of some blocks is, optionally, changed, and some blocks are, optionally, omitted. In some examples, additional steps may be performed in combination with the exemplary processes. Accordingly, the operations as illustrated (and described in greater detail below) are exemplary by nature and, as such, should not be viewed as limiting.

The disclosures of all publications, patents, and patent applications referred to herein are each hereby incorporated by reference in their entireties. To the extent that any reference incorporated by reference conflicts with the instant disclosure, the instant disclosure shall control.

Flow Sequencing Methods

Sequencing data can be generated using a flow sequencing method that includes extending a primer bound to a template polynucleotide molecule according to a pre-determined flow cycle where, in any given flow position, a single type of nucleotide is accessible to the extending primer. In some embodiments, at least some of the nucleotides of the particular type include a label, which upon incorporation of the labeled nucleotides into the extending primer renders a detectable signal. The resulting sequence by which such nucleotides are incorporated into the extended primer should be the reverse complement of the sequence of the template polynucleotide molecule. In some embodiments, for example, sequencing data is generated using a flow sequencing method that includes extending a primer using labeled nucleotides, and detecting the presence or absence of a labeled nucleotide incorporated into the extending primer. Flow sequencing methods may also be referred to as "natural sequencing-by-synthesis," or "non-terminated sequencing-by-synthesis" methods. Exemplary methods are described in U.S. Pat. No. 8,772,473, which is incorporated herein by reference in its entirety. While the following description is provided in reference to flow sequencing methods, it is understood that other sequencing methods may be used to sequence all or a portion of the sequenced region.

Flow sequencing includes the use of nucleotides to extend the primer hybridized to the polynucleotide. Nucleotides of a given base type (e.g., A, C, G, T, U, etc.) can be mixed with hybridized templates to extend the primer if a complementary base is present in the template strand. The nucleotides may be, for example, non-terminating nucleotides. When the nucleotides are non-terminating, more than one consecutive base can be incorporated into the extending primer strand if more than one consecutive complementary base is present in the template strand. The non-terminating nucleotides contrast with nucleotides having 3' reversible terminators, wherein a blocking group is generally removed before a successive nucleotide is attached. If no complementary base is present in the template strand, primer extension ceases until a nucleotide that is complementary to the next base in the template strand is introduced. At least a portion of the nucleotides can be labeled so that incorporation can be detected. Most commonly, only a single nucleotide type is introduced at a time (i.e., discretely added), although two or three different types of nucleotides may be simultaneously introduced in certain embodiments. This methodology can be contrasted with sequencing methods that use a reversible terminator, wherein primer extension is stopped after extension of every single base before the terminator is reversed to allow incorporation of the next succeeding base.

The nucleotides can be introduced at a determined order during the course of primer extension, which may be further divided into cycles. Nucleotides are added stepwise, which allows incorporation of the added nucleotide to the end of the sequencing primer of a complementary base in the template strand is present. The cycles may have the same order of nucleotides and number of different base types or a different order of nucleotides and/or a different number of different base types. However, no set of bases (i.e., the one or more different bases simultaneously used in a single flow step) corresponding to a given flow step is repeated in the same cycle as the term is used herein, which can provide as a marker to distinguish between different cycles. Solely by way of example, the order of a first cycle may be A-T-G-C and the order of a second cycle may be A-T-C-G. Further, one or more cycles may omit one or more nucleotides. Solely by way of example, the order of a first cycle may be A-T-G-C and the order of a second cycle may be A-T-C. Alternative orders may be readily contemplated by one skilled in the art. Between the introductions of different nucleotides, unincorporated nucleotides may be removed, for example by washing the sequencing platform with a wash fluid.

A polymerase can be used to extend a sequencing primer by incorporating one or more nucleotides at the end of the primer in a template-dependent manner. In some embodiments, the polymerase is a DNA polymerase. The polymerase may be a naturally occurring polymerase or a synthetic (e.g., mutant) polymerase. The polymerase can be added at an initial step of primer extension, although supplemental polymerase may optionally be added during sequencing, for example with the stepwise addition of nucleotides or after a number of flow cycles. Exemplary polymerases include a DNA polymerase, an RNA polymerase, a thermostable polymerase, a wild-type polymerase, a modified polymerase, Bst DNA polymerase, Bst 2.0 DNA polymerase Bst 3.0 DNA polymerase, Bsu DNA polymerase, E. coli DNA polymerase I, T7 DNA polymerase, bacteriophage T4 DNA polymerase Φ29 (phi29) DNA polymerase, Taq polymerase, Tth polymerase, Tli polymerase, Pfu polymerase, and SeqAmp DNA polymerase.

The introduced nucleotides can include labeled nucleotides when determining the sequence of the template strand, and the presence or absence of an incorporated labeled nucleic acid can be detected to determine a sequence. The label may be, for example, an optically active label (e.g., a fluorescent label) or a radioactive label, and a signal emitted by or altered by the label can be detected using a detector. The presence or absence of a labeled nucleotide incorporated into a primer hybridized to a template polynucleotide can be detected, which allows for the determination of the sequence (for example, by generating a flowgram). In some embodiments, the labeled nucleotides are labeled with a fluorescent, luminescent, or other light-emitting moiety. In some embodiments, the label is attached to the nucleotide via a linker. In some embodiments, the linker is cleavable, e.g., through a photochemical or chemical cleavage reaction. For example, the label may be cleaved after detection and before incorporation of the successive nucleotide(s). In some embodiments, the label (or linker) is attached to the nucleotide base, or to another site on the nucleotide that does not interfere with elongation of the nascent strand of DNA. In some embodiments, the linker comprises a disulfide or PEG-containing moiety.

In some embodiment, the nucleotides introduced include only unlabeled nucleotides, and in some embodiments the nucleotides include a mixture of labeled and unlabeled nucleotides. For example, in some embodiments, the portion of labeled nucleotides compared to total nucleotides is about 90% or less, about 80% or less, about 70% or less, about 60% or less, about 50% or less, about 40% or less, about 30% or less, about 20% or less, about 10% or less, about 5% or less, about 4% or less, about 3% or less, about 2.5% or less, about 2% or less, about 1.5% or less, about 1% or less, about 0.5% or less, about 0.25% or less, about 0.1% or less, about 0.05% or less, about 0.025% or less, or about 0.01% or less. In some embodiments, the portion of labeled nucleotides compared to total nucleotides is about 100% or more, about 95% or more, about 90% or more, about 80% or more about 70% or more, about 60% or more, about 50% or more, about 40% or more, about 30% or more, about 20% or more, about 10% or more, about 5% or more, about 4% or more, about 3% or more, about 2.5% or more, about 2% or more, about 1.5% or more, about 1% or more, about 0.5% or more, about 0.25% or more, about 0.1% or more, about 0.05% or more, about 0.025% or more, or about 0.01% or more. In some embodiments, the portion of labeled nucleotides compared to total nucleotides is about 0.01% to about 100%, such as about 0.01% to about 0.025%, about 0.025% to about 0.05%, about 0.05% to about 0.1%, about 0.1% to about 0.25%, about 0.25% to about 0.5%, about 0.5% to about 1%, about 1% to about 1.5%, about 1.5% to about 2%, about 2% to about 2.5%, about 2.5% to about 3%, about 3% to about 4%, about 4% to about 5%, about 5% to about 10%, about 10% to about 20%, about 20% to about 30%, about 30% to about 40%, about 40% to about 50%, about 50% to about 60%, about 60% to about 70%, about 70% to about 80%, about 80% to about 90%, about 90% to less than 100%, or about 90% to about 100%.

Sequencing data, such as a flowgram, can be generated based on the detection of an incorporated nucleotide and the order of nucleotide introduction. Take, for example, the flowing template sequences: CTG and CAG, and a repeating flow cycle of T-A-C-G (that is, sequential addition of T, A, C, and G nucleotides, which would be incorporated into the primer only if a complementary base is present in the template polynucleotide). A resulting flowgram is shown in Table 1, where 1 indicates incorporation of an introduced nucleotide and 0 indicates no incorporation of an introduced nucleotide. The flowgram can be used to determine the sequence of the template strand.

TABLE 1

| Sequence | Cycle 1 | | | | Cycle 2 | | | |
| --- | --- | --- | --- | --- | --- | --- | --- | --- |
| | T | A | C | G | T | A | C | G |
| CTG | 0 | 0 | 0 | 1 | 0 | 1 | 1 | 0 |
| CAG | 0 | 0 | 0 | 1 | 1 | 0 | 1 | 0 |
| CCG | 0 | 0 | 0 | 2 | 0 | 0 | 1 | 0 |

The flowgram may be binary or non-binary. A binary flowgram detects the presence (1) or absence (0) of an incorporated nucleotide. A non-binary flowgram can more quantitatively determine a number of incorporated nucleotide from each stepwise introduction. For example, a sequence of CCG would incorporate two G bases, and any signal emitted by the labeled base would have a greater intensity as the incorporation of a single base. This is shown in Table 1. The non-binary flowgram also indicates the presence or absence of the base, but can provide additional information including the number of bases incorporated at the given step.

Prior to generating the sequencing data, the polynucleotide is hybridized to a sequencing primer to generate a hybridized template. The polynucleotide may be ligated to an adapter during sequencing library preparation. The adapter can include a hybridization sequence that hybridizes to the sequencing primer. For example, the hybridization sequence of the adapter may be a uniform sequence across a plurality of different polynucleotides, and the sequencing primer may be a uniform sequencing primer. This allows for multiplexed sequencing of different polynucleotides in a sequencing library.

The polynucleotide may be attached to a surface (such as a solid support) for sequencing. The polynucleotides may be amplified (for example, by bridge amplification or other amplification techniques) to generate polynucleotide sequencing colonies. The amplified polynucleotides within the cluster are substantially identical or complementary (some errors may be introduced during the amplification process such that a portion of the polynucleotides may not necessarily be identical to the original polynucleotide). Colony formation allows for signal amplification so that the detector can accurately detect incorporation of labeled nucleotides for each colony. In some cases, the colony is formed on a bead using emulsion PCR and the beads are distributed over a sequencing surface. Examples for systems and methods for sequencing can be found in U.S. Pat. No. 10,344,328, which is incorporated herein by reference in its entirety.

The primer hybridized to the polynucleotide is extended through the first region, the second region, and the third region of the polynucleotide. Sequencing data associated with the sequence within the first region and/or the third region may be generated as discussed above. However, the primer is extended through the second region (which is between the first region and the third region) using an accelerated "fast forward" process. That is, extension of the primer through the second region between the first region and the third region of the polynucleotide may proceed faster that the extension of the primer through the first region and/or the third region. For example, extension of the primer through the second region may proceed by extending the primer without detecting the presence or absence of a labeled nucleotide incorporated into the extending primer. During flow sequencing, as discussed above, a labeled nucleotide is incorporated into the extending primer, the hybridized template is washed, and a detector is used to detect a signal from the label of the nucleotide, which indicates whether the nucleotide has been incorporated into the extended primer. However, the detection process takes time, and extension of the primer through the second region can be accelerated by skipping the detection process. In some embodiments, the primer is extended through the second region using unlabeled nucleotides (or using only unlabeled nucleotides), which can further accelerate the rate of primer extension.

Extension of the primer through the second region may alternatively or additionally be accelerated by using a mixture of at least two different types of nucleotides in at least one step of the flow order used during extension of the primer through the second region. For example, two different bases, such as G and C, may be used simultaneously in the same step, which extends the primer if a complementary C or G base are present. This accelerates extension of the primer by incorporating consecutive bases in to the primer even if those bases are of different base types. In some embodiments, at least one step of the flow order includes 2 different bases. In some embodiments, at least one step of the flow order includes 3 different baes. By way of example, consider a sequence of SEQ ID NO: 1 and the corresponding flow order and flowgram shown in Table 2. The flow order process for extending the sequencing primer hybridized to a polynucleotide containing SEQ ID NO: 1 includes 5 cycles, with Cycles 1, 4, and 5 being the same as each other and Cycles 2 and 3 being the same as each other (with Cycles 1, 4, and 5 being different from Cycles 2 and 3). In this example, each cycle has 4 steps, with Cycles 1, 4, and 5 include the sequential and independent addition of A-C-T-G nucleotides, with a single base type being added at each cycle step. Cycles 2 and 3 include four cycle steps, wherein Step 1 omits A nucleotides (i.e., includes C, T, and G), Step 2 omits, C nucleotides (i.e., includes A, T, and G), Step 3 omits T nucleotides (i.e., includes A, C, and G), and Step 4 omits G nucleotides (i.e., includes A, C, and T). Because Cycles 2 and 3 include multiple different nucleotide base types simultaneously during primer extension, the primer is extended faster than if only a single base type was used at any given step. The flowgram shown in Table 2 for extending the primer against the SEQ ID NO: 1 template using this flow order results in up to 6 bases being added (Cycle 3, Step 3) during the fast forward portion of primer extension. In contrast, Table 3 shows a flowgram of the same SEQ ID NO: 1 using the A-C-T-G cycles with single nucleotides used at each step (similar to Cycles 1, 4, and 5 in Table 2). The flow order used to extend the primer shown in Table 3 requires 10 four-step cycles to extend the primer through the polynucleotide, which is substantially slower than the 5 four-step cycles used to extend the primer through the polynucleotide using the flow order provided in Table 2.

TABLE 2

Flowgram for SEQ ID NO: 1: 3'-TGACTTGAATCCGATATGCCTGCAGCTGAC-5'

| | Cycle | | | | | | | | | | | |
|---|---|---|---|---|---|---|---|---|---|---|---|---|
| | 1 | | | | 2 | | | | 3 | | | 4 | 5 |
| | Cycle Step | | | | | | | | | | | |
| | 1 2 3 4 | 1 | 2 | 3 | 4 | 1 | 2 | 3 | 4 | 1 2 3 4 | 1 2 3 4 |
| Flow Bases | A C T G | C/T/G | A/T/G | A/C/G | A/C/T | C/T/G | A/T/G | A/C/G | A/C/T | A C T G | A C T G |
| Number of Bases Incorporated | 1 1 1 0 | 2 | 1 | 3 | 4 | 3 | 6 | 2 | 0 0 0 1 | 1 1 1 1 |
| Base(s) Incorporated | A C T G — | AA | C | TTA | GGCT | ATA | CGGACG | TC | — — — G | A C T G |

TABLE 3

Flowgram for SEQ ID NO: 1 3'-TGACTTGAATCCGATATGCCTGCAGCTGAC-5'

| | Cycle | | | | | | | | | | | | | | | | | | |
|---|---|---|---|---|---|---|---|---|---|---|---|---|---|---|---|---|---|---|---|
| | 1 | | | | 2 | | | | 3 | | | | 4 | | | | 5 | | |
| | Cycle Step | | | | | | | | | | | | | | | | | | |
| | 1 | 2 | 3 | 4 | 1 | 2 | 3 | 4 | 1 | 2 | 3 | 4 | 1 | 2 | 3 | 4 | 1 | 2 | 3 | 4 |
| Flow Bases | A | C | T | G | A | C | T | G | A | C | T | G | A | C | T | G | A | C | T | G |
| Number of Bases Incorporated | 1 | 1 | 1 | 1 | 2 | 1 | 2 | 0 | 1 | 0 | 0 | 2 | 0 | 1 | 1 | 0 | 1 | 0 | 1 | 0 |
| Bases Incorporated | A | C | T | G | AA | C | TT | — | A | — | — | CC | — | C | T | — | A | — | T | — |

| | Cycle | | | | | | | | | | | | | | | | | | |
|---|---|---|---|---|---|---|---|---|---|---|---|---|---|---|---|---|---|---|---|
| | 6 | | | | 7 | | | | 8 | | | | 9 | | | | 10 | | |
| | Cycle Step | | | | | | | | | | | | | | | | | | |
| | 1 | 2 | 3 | 4 | 1 | 2 | 3 | 4 | 1 | 2 | 3 | 4 | 1 | 2 | 3 | 4 | 1 | 2 | 3 | 4 |
| Flow Bases | A | C | T | G | A | c | T | G | A | c | T | G | A | c | T | G | A | c | T | G |
| Number of Bases Incorporated | 1 | 1 | 0 | 2 | 1 | 1 | 0 | 1 | 0 | 0 | 1 | 0 | 0 | 1 | 0 | 1 | 1 | 1 | 1 | 1 |
| Base(s) Incorporated | A | C | — | GG | A | C | — | G | — | — | T | — | — | C | — | G | A | C | T | G |

The fast forward method is particularly useful for accelerating primer extension through a region that is not directly sequenced. For example, in reference to Table 2, Cycles 1, 4, and 5 used labeled nucleotides in a stepwise manner to generate sequencing data associated with the first region (Cycle 1) and the third region (Cycles 4 and 5), while the primer was quickly extended through the second region (Cycles 2 and 3) between the first and third region.

Primer extension using flow sequencing allows for long-range sequencing on the order of hundreds or even thousands of bases in length. The number of flow steps or cycles can be increased or decreased to obtain the desired sequencing length. Extension of the primer in the first region or the third region can include one or more flow steps for stepwise extension of the primer using nucleotides having one or more different base types. In some embodiments, extension of the primer in the first region or extension of the primer in the third region includes between 1 and about 1000 flow steps, such as between 1 and about 10 flow steps, between about 10 and about 20 flow steps, between about 20 and about 50 flow steps, between about 50 and about 100 flow steps, between about 100 and about 250 flow steps, between about 250 and about 500 flow steps, or between about 500 and about 1000 flow steps. The flow steps may be segmented into identical or different flow cycles. The number of bases incorporated into the primer in the first region or the third region depends on the sequence of the first region or third region, respectively, and the flow order used to extend the primer in the first region or third region. In some embodiments, the first region or third region is about 1 base to about 4000 bases in length, such as about 1 base to about 10 bases in length, about 10 bases to about 20 bases in length, about 20 bases to about 50 bases in length, about 50 bases to about 100 bases in length, about 100 bases to about 250 bases in length, about 250 bases to about 500 bases in length, about 500 bases to about 1000 bases in length, about 1000 bases to about 2000 bases in length, or about 2000 bases to about 4000 bases in length.

Primer extension through the second region may proceed through any number of flow steps. In some embodiments, extension of the primer through the second region omits labeled nucleotides, which further increases the feasible extension distance of the primer without polymerase stall. In some embodiments, extension of the primer through the second region includes between 1 and about 10,000 flow steps, such as between 1 and about 10 flow steps, between about 10 and about 20 flow steps, between about 20 and about 50 flow steps, between about 50 and about 100 flow steps, between about 100 and about 250 flow steps, between about 250 and about 500 flow steps, between about 500 and about 1000 flow steps, between about 1000 flow steps and about 2500 flow steps, between about 2500 flow steps and about 5000 flow steps, or between about 5000 flow steps and about 10,000 flow steps. In some embodiments, extension of the primer through the second region includes more than about 10,000 flow steps. The number of bases incorporated into the primer in the second region depends on the sequence of the second region, and the flow order used to extend the primer in the second region. In some embodiments, the second region is about 1 base to about 50,000 bases in length, such as about 1 base to about 10 bases in length, about 10 bases to about 20 bases in length, about 20 bases to about 50 bases in length, about 50 bases to about 100 bases in length, about 100 bases to about 250 bases in length, about 250 bases to about 500 bases in length, about 500 bases to about 1000 bases in length, about 1000 bases to about 2000 bases in length, about 2000 bases to about 2500 bases in length, about 2500 to about 5000 bases in length, about 5000 to about 10,000 bases in length, about 10,000 to about 25,000 bases in length, or about 25,000 to about 50,000 bases in length. In some embodiments, the length of the second region is more than about 50,000 bases in length.

Extension of the primer can proceed through the first region, the second region, and the third region, wherein the primer is extended through the first region and the third region using labeled nucleotides. Detection of nucleotides incorporated into the extending primer can be detected to generate sequencing data. Extension of the primer through the second region can occur at a faster rate than extension of the primer through the first and/or third regions, for example without detecting the presence or absence of a label of a nucleotide incorporated into the extending primer, or by including a mixture of at least two different types of nucleotide bases to extend the primer (wherein the extension of the primer through the first and/or third relies on fewer different types of nucleotide bases). Extension of the primer may be further extended in an alternating pattern. For example, after the primer is extended through the third region, it may be further extended into a fourth region. Extension of the primer through the fourth region can occur at a faster rate than extension of the primer through the first and/or third regions, for example without detecting the presence or absence of a label of a nucleotide incorporated into the extending primer, or by including a mixture of at least two different types of nucleotide bases to extend the primer. The primer may then be extended into a fifth region using labeled nucleotides, and sequencing data can be generated for the fifth region by detecting nucleotides incorporated into the extended primer. This process may be repeated for as many altering cycles as desired. Sequencing data from any two regions may be associated to generate a coupled sequencing read pair, and coupled sequencing read pair may be analyzed as described herein (for example, by considering the region between the selected region to be the "second region" as described for the analytical methods provided herein).

FIG. 1 illustrates a schematic of an exemplary method for generating a coupled sequencing read pair from a polynucleotide (such as DNA). At 102, the polynucleotide 104 is hybridized with a primer 106 to form a hybridized template. In some embodiments, the polynucleotide includes an adapter region 108, which may be ligated to the 3' of the target polynucleotide during sequencing library preparation. The adapter region 108 can include a hybridization region, and the primer 106 can hybridize to the hybridization region of the adapter region 108. At step 110, sequencing data for the first region 112 of the polynucleotide 104 is generated by extending the primer 106 using labeled nucleotides, and detecting the presence or absence of an incorporated labeled nucleotide. The nucleotides used to extend the primer may further include unlabeled nucleotides, although labeled nucleotides are used to detect nucleotide incorporation for generating the sequencing data. In some embodiments, the nucleotides are added stepwise in one or more cycles according to a first region flow order to extend the primer 106 through the first region 112, and the hybridized template may be washed following a cycle step to remove unincorporated nucleotides prior to detecting the presence or absence of an incorporated labeled nucleotide. At step 114, the primer 106 is extended through a second region 116 of the polynucleotide 104 according to a second region flow order. The primer 106 may be extended through the second region 116 at a rate faster than extension of the primer in step 110. This accelerated primer extension may be referred to as the "fast-forward" portion of the method. Nucleotides (which, in some embodiments, are unlabeled) are added to the hybridized template stepwise in one or more cycles according to the second region flow order. In some embodiments, more than one (e.g., two or three) different base types are simultaneously used in a given cycle step, which accelerates the primer extension. In some embodiments, the nucleotides are unlabeled, which allows for faster primer extension than labeled nucleotides. In some embodiments, the primer is extended without detecting the presence or absence of a label of a nucleotide. At step 118, sequencing data for the third region 118 of the polynucleotide 104 is generated by extending the primer 106 using labeled nucleotides, and detecting the presence or absence of an incorporated labeled nucleotide. Generation of the sequencing data for the third region 118 may proceed in a similar manner as described for generating the sequencing data for the first region 112. At step 122, the sequencing data generated for the first region 112 is associate with the sequencing data generated for the third region 120, which results in the coupled sequencing read pair 124 for the polynucleotide 104. The sequencing data associated between the first and third regions may include the sequence of the first and third regions. The coupled sequencing read pair 124 includes sequencing data for the first region 112 and the third region 120, which are separated by the second region 116 for which sequencing data is not necessarily known.

Generation of sequencing data for the first region of the polynucleotide need not be generated in accordance with some of the embodiments described herein. For example, the sequencing primer can be used for targeted sequencing by hybridizing to a targeted region. In targeted sequencing, the first region of the polynucleotide is known and the primer is designed to specifically bind to the first region. The primer can then be extended through the second and third regions as described, with sequencing data for the third region being generated. In some embodiments, a method of generating a coupled sequencing read pair from a polynucleotide, includes (a) hybridizing a primer to a first region of the polynucleotide to form a hybridized template; (b) extending the primer through a second region using nucleotides provided in a second region flow order, wherein (i) the primer is extended through the second region without detecting the presence or absence of a label of a nucleotide incorporated into the extending primer, or (ii) a mixture of at least two different types of nucleotide bases are used in at least one step of the second region flow order; and (c) generating sequencing data associated with a sequence of a third region of the polynucleotide by further extending the primer extended in step (b) using labeled nucleotides, and detecting the presence or absence of an incorporated labeled nucleotide.

A reference sequence can be used to determine expected sequencing data (such as a flowgram) for the first region, the second region, and/or the third region. The sequence for the first and third regions can be determined from the generated sequencing data for those regions. For example, in reference to Table 2, Cycle 1 is associated with the first region, for which the sequence is readily determined as the complement to the bases (i.e., base flow A-C-T-G corresponds to a sequence of TGAC), and Cycles 4 and 5 are associated with the third region, for which the sequence is determined as CTGAC (i.e., the complement of G-A-C-T-G). Thus, using the generated sequencing data from the first region and/or the third region, the first region and/or the third region (or at least a portion of the first region and/or the third region) can be mapped to the reference sequence. Once mapped to reference sequence, expected sequencing data for the second region can be generated using the flow order used to extend the primer through the second region and the reference sequence.

Expected sequencing data may also be determined for the third region using the reference sequence for the second region, the flow order for the second region, the flow order for the third region, and information about the sequence of the third region. Similarly, expected sequencing data may be determined for the first region using the reference sequence for the second region, the flow order for the second region, the flow order for the first region, and information about the sequence of the first region. The information about the sequence of the third region (or first region) may be obtained from, for example, the reference sequence (or a different reference sequence) or generated sequencing data such as the sequencing data generated by extending the primer using labeled nucleotides and detecting the presence or absence of an incorporated labeled nucleotide, or sequencing data obtained by other methods (e.g., independently sequencing the third region of the third region of the polynucleotide).

By way of example, the expected sequencing data for the third region may be determined using a reference sequence for the second region, the second region flow order, the third region flow order, and a reference sequence for the third region. The first region (or a portion thereof) may be mapped to a reference sequence, and the reference sequence corresponding to the second region and the second region flow order may be used to determine expected reference sequencing data for the second region. Similarly, the reference sequence for the third region may be used, along with the third region flow order, to determine an expected reference sequencing data for the third region. The expected sequencing data for the first region may be determined using a similar method. For example, the expected sequencing data for the first region may be determined using a reference sequence for the second region, the second region flow order, the first region flow order, and a reference sequence for the first region. The third region (or a portion thereof) may be mapped to a reference sequence, and the reference sequence corresponding to the second region and the second region flow order may be used to determine expected reference sequencing data for the second region. Similarly, the reference sequence for the first region may be used, along with the first region flow order, to determine an expected reference sequencing data for the first region.

In another example, the expected sequencing data for the third region may be determined using a reference sequence for the second region, the second region flow order, the third region flow order, and sequencing data associated with the sequenced of the third region, which may be the same or different from the sequencing data generated as previously described. The first region (or a portion thereof) may be mapped to a reference sequence, and the reference sequence corresponding to the second region and the second region flow order may be used to determine expected reference sequencing data for the second region. The sequencing data for the third region may be used to determine the sequence of the third region. Further the sequence of the third region may be used, along with the third region flow order, to determine expected sequencing data for the third region.

Figure 2:
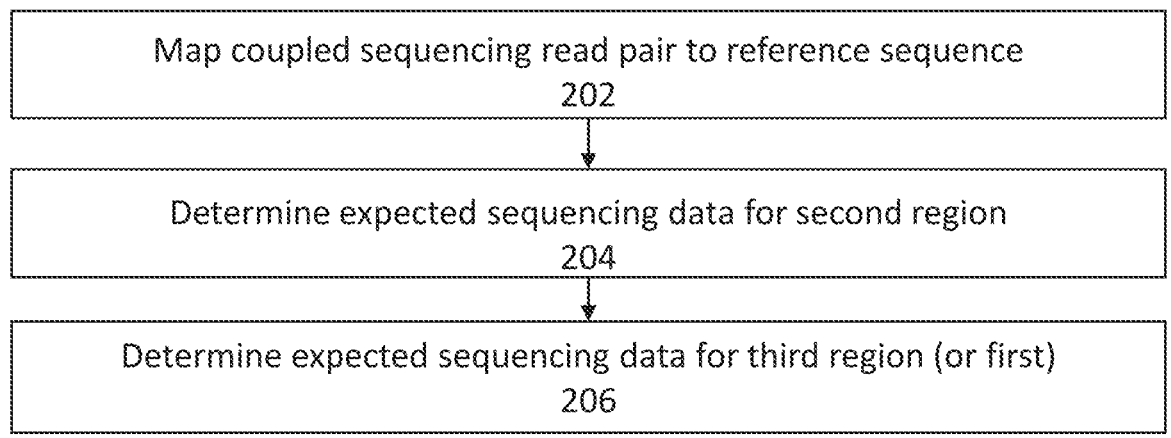
FIG. 2 illustrates a schematic of an exemplary method for generating expected sequencing data using a reference sequence.

FIG. 2 illustrates a schematic of an exemplary method for generating expected sequencing data. At step 202, the coupled sequencing read pair is mapped to a reference sequence. Mapping the coupled sequencing read pair may include mapping the first region (or portion thereof) of the coupled sequencing read pair (or portion thereof) to the reference sequence, mapping the third region (or portion thereof) of the coupled sequencing read pair to the reference sequence, or both the first region (or portion thereof) and the third region (or portion thereof) to the reference sequence. At step 204, the expected sequencing data (such as an expected flowgram) for the second region is determined using the second region flow order and the reference sequence. With the flow order and reference sequencing known, determining the expected sequencing data (that is, the sequencing data that would be expected if the second region of the polynucleotide matches the reference sequence) is readily obtainable. Further, the expected sequencing data for the second region can be used to determine the expected 5' end of the second region. The 5' end of the second region may vary depending on the flow order for that region and the sequence of the second region. Thus, the 3' end of the third region can also vary based on the second region flow order and sequence of the second region because the 3' end of the third region is adjacent to the 5' end of the second region. Once the 3' end of the third region is established (for example, as determined using the expected sequencing data for the second region), the expected sequencing data for the third region can be determined, as shown in step 206. As further described herein, the expected sequencing data for the third region may be used to determine variants, such as a variant within the second region of the polynucleotide.

If the polynucleotide includes a variant within the second region, the generated sequencing data (e.g., the flowgram) associated with the third region may differ (depending on the sequence context and the size of the variant) from the expected sequencing data associated with the third region. Thus, in some embodiments, variants are detected based on the difference between the expected sequencing data and the generated sequencing data.

The reference sequence may be any suitable sequence of the same species as the polynucleotide, and there may be some differences between the reference sequence and the sequence of the polynucleotide. In some embodiments of the methods described herein, these differences, or variants, can be detected. In some embodiments, a test variant (i.e., a variant of interest) is included in the reference sequence, and in other embodiments, the test variant is omitted from the reference sequence. In some embodiments, the analysis may be performed with two different reference sequences, with one reference sequence including the test variant and the other reference sequence omitting the test variant. In some embodiments, the only difference between the two reference sequences is the presence or absence of the test variant.

The sensitivity of the variant detection methods described herein may depend on the context of the variant and/or the flow order used to extend the primer in the first, second and/or third region. A missed variant with a given flow order may be detectable using a different flow order in the first, second and/or third region. Accordingly, in some embodiments of the method described herein, the more than one coupled sequencing read pair is generated using different flow orders for extending the primer through one or more of the first, second, and/or third region of the polynucleotide.

The polynucleotides used in the methods described herein may be obtained from any suitable biological source, for example a tissue sample, a blood sample, a plasma sample, a saliva sample, a fecal sample, or a urine sample. The polynucleotides may be DNA or RNA polynucleotides. In some embodiments, RNA polynucleotides are reverse transcribed into DNA polynucleotides prior to hybridizing the polynucleotide to the sequencing primer. In some embodiments, the polynucleotide is a cell-free DNA (cfDNA), such as a circulating tumor DNA (ctDNA) or a fetal cell-free DNA.

Libraries of the polynucleotides may be prepared through known methods. In some embodiments, the polynucleotides may be ligated to an adapter sequence. The adapter sequence may include a hybridization sequence that hybridized to the primer extended during the generated of the coupled sequencing read pair.

In some embodiments, the sequencing data is obtained without amplifying the nucleic acid molecules prior to establishing sequencing colonies (also referred to as sequencing clusters). Methods for generating sequencing colonies include bridge amplification or emulsion PCR. Methods that rely on shotgun sequencing and calling a consensus sequence generally label nucleic acid molecules using unique molecular identifiers (UMIs) and amplify the nucleic acid molecules to generate numerous copies of the same nucleic acid molecules that are independently sequenced. The amplified nucleic acid molecules can then be attached to a surface and bridge amplified to generate sequencing clusters that are independently sequenced. The UMIs can then be used to associate the independently sequenced nucleic acid molecules. However, the amplification process can introduce errors into the nucleic acid molecules, for example due to the limited fidelity of the DNA polymerase. In some embodiments, the nucleic acid molecules are not amplified prior to amplification to generate colonies for obtaining sequencing data. In some embodiments, the nucleic acid sequencing data is obtained without the use of unique molecular identifiers (UMIs).

In some embodiments, the flow sequencing methods are used with rolling circle amplification (RCA) sequencing. RCA allows for formation of multiple copies of a nucleic acid molecule covalently attached in a linear sequence. See, for example, Dean et al., Rapid Amplification of Plasmid and Phage DNA Using Phi29 DNA Polymerase and Multiply-Primed Rolling Circle Amplification, Genome Research, vol. 11, pp. 1095-1099 (20001); and U.S. Pat No. 5,714,320, the contents of each of which are incorporated herein by reference. Because multiple copies of the nucleic acid molecule can be linearly sequenced, a given region may be alternatively sequenced in a "dark" or mode or a "light" mode as the sequencing progresses. In some embodiments, sequencing mode switching may be dynamically (and, optionally, automatically) determined. For example, a variant may be detected within a "dark" region, but the limited information that is generated prevents a specific variant being called. Therefore, the sequencing flows can be dynamically adjusted to sequencing the region of the nucleic acid molecule containing the variant in a light mode. For example, a method of detecting a short genetic variant in a test sample may include (a) amplifying a polynucleotide using rolling circle amplification (RCA) to generate a RCA-amplified polynucleotide comprising at least a first copy of the polynucleotide and a second copy of the polynucleotide; (b) hybridizing the RCA-amplified polynucleotide to a primer to form a hybridized template; (c) generating sequencing data associated with a sequence of a first region of the polynucleotide within the first copy of the polynucleotide by extending the primer using labeled nucleotides, and detecting the presence or absence of an incorporated labeled nucleotide; (d) further extending the primer through a second region of the polynucleotide within the first copy of the polynucleotide using nucleotides provided in a second region flow order, wherein (i) the primer is extended through the second region of the polynucleotide within the first copy of the polynucleotide without detecting the presence or absence of a label of a nucleotide incorporated into the extending primer, (ii) a mixture of at least two different types of nucleotide bases are used in at least one step of the second region flow order, or (iii) extension of the primer through the second region of the polynucleotide within the first copy of the polynucleotide proceeds faster than the extension of the primer through the first region; (e) generating sequencing data associated with a sequence of a third region of the polynucleotide by further extending the primer using labeled nucleotides, and detecting the presence or absence of an incorporated labeled nucleotide; (f) comparing the sequencing data generated for the third region of the polynucleotide to expected sequencing data for an expected sequence of the third region of the polynucleotide; (g) calling the presence of the short genetic variant in the second region of the polynucleotide; (h) generating sequencing data associated with a sequence of the second region of the polynucleotide within the second copy of the polynucleotide by extending the primer using labeled nucleotides, and detecting the presence or absence of an incorporated labeled nucleotide; and (i) calling the identity of the short genetic variant in the second region of the polynucleotide. In some embodiments, the sequencing data associated with the sequence of the second region of polynucleotide within the second copy of the polynucleotide is dynamically generated based on calling the presence of the short genetic variant in the second region of the polynucleotide.

Extended Flow Cycles

Flow cycle orders need not be limited to four base flow cycles (e.g., one each of A, G, C, and T, in any repeated order), and may be an extended flow cycle with more than four base types in a cycle. The extended cycle order may be repeated for the desired number of cycles to extend the sequencing primer. By way of example, in some embodiments, the extended flow order includes 5, 6, 7, 8, 9, 10, 11, 12, 13, 14, 15, 16, 17, 18, 19, 20, or more separate nucleotide flows in the flow cycle order. The cycles can include at least one each of A, G, C, and T, but repeat one or more base types within the cycle before the cycle is repeated. The extended flow cycles may be used, for example, to extend the primer through the second region according to the methods described herein.

The extended flow cycle orders can be useful for detecting a greater proportion of small genomic variants (e.g., SNPs) than a flow cycle order with four repeated bases. For example, there are 192 valid configurations of substitution SNPs in the form XYZ→XQZ where Q≠Y (and Q, X, Y, and Z are each any one of A, C, G, and T). Of these, 168 can produce a new signal (i.e., a new non-zero signal or a new zero signal) in the sequencing data set (e.g., a flowgram). A new zero or non-zero signal combined with a sensitive flow order can produce a signal that is propagated for multiple flow positions (e.g., a flow shift, which may extend more than the length of the cycle), given identical trailing sequences in the variant relative to the reference. It is noted that insertion or deletion of a homopolymer, rather than a homopolymer length change, can result in a signal difference propagation. The remaining 24 variants causes a homopolymer length change at the affected flow position, but such a change does not cause a propagated signal change. Thus, a theoretical maximum of 87.5% of SNPs can result in a new signal that differs from a reference (or candidate) sequence for more than two flow positions. As discussed above, the propagated signal difference increases the likelihood difference between a test sequencing data set and an incorrectly matched candidate sequence. Further, the propagated signal change depends on the flow order spanning the variant.

Sequencing nucleic acid molecules in a test sample that have been randomly fragmented results in a random shift in the flow order context of the variant when the sequencing primer is extended using the flow order. That is, the flow position of the variant may change depending on the start position of the sequenced nucleic acid molecule. Not all flow cycle combinations are able to detect signal changes at more than two flow positions for all 87.5% of SNPs, even if all sequencing start positions in a nucleic acid molecule sequence are utilized. For example, the four-base flow cycle order T-A-C-G can result in a test sequencing data set that differs from a reference sequencing data set at more than two flow positions for 41.7% of SNPs. As further discussed herein, extended flow cycle orders have been designed so that all of the theoretical maximum of SNPs (i.e., 87.5% of possible SNPs, or all SNPs other than those resulting in a homopolymer length change) can give rise to a difference at more than two flow position between the test sequencing data set and the reference sequencing data set, given a high enough sequencing depth (i.e., sampling a sufficiently large number of start positions).

Extended sequencing flow orders may have different efficiencies (i.e., the average number of incorporations per flow when used to sequence a human reference genome). In some embodiments, the flow order has an efficiency of about 0.6 or greater (such as about 0.62 or greater, about 0.64 or greater, about 0.65 or greater, about 0.66 or greater, or about 0.67 or greater). In some embodiments, the flow order has an efficiency of about 0.6 to about 0.7. Examples of flow cycle orders and corresponding estimated efficiencies are shown in Table 4.

In some embodiments, the extended sequencing flow order is selected to generate signal differences at more than two flow positions between two sequencing data sets (e.g., a test or target sequencing data set and a candidate or reference sequencing data set) associated with nucleic acid molecules differing by a SNP for about 50% to 87.5% of SNP permutations for at least 5% of random sequencing start positions. In some embodiments, the extended sequencing flow order is selected to generate signal differences at more than two flow positions between two sequencing data sets (e.g., a test or target sequencing data set and a candidate or reference sequencing data set) associated with nucleic acid molecules differing by a SNP for about 60% to 87.5% of SNP permutations for at least 5% of random sequencing start positions (i.e., "flow phases"). In some embodiments, the extended sequencing flow order is selected to generate signal differences at more than two flow positions between two sequencing data sets (e.g., a test or target sequencing data set and a candidate or reference sequencing data set) associated with nucleic acid molecules differing by a SNP for about 70% to 87.5% of SNP permutations for at least 5% of random sequencing start positions. In some embodiments, the extended sequencing flow order is selected to generate signal differences at more than two flow positions between two sequencing data sets (e.g., a test or target sequencing data set and a candidate or reference sequencing data set) associated with nucleic acid molecules differing by a SNP for about 80% to 87.5% of SNP permutations for at least 5% of random sequencing start positions.

In some embodiments, the extended sequencing flow order is selected to generate signal differences at more than two flow positions between two sequencing data sets (e.g., a test or target sequencing data set and a candidate or reference sequencing data set) associated with nucleic acid molecules differing by a SNP for about 50% to 87.5% of SNP permutations for at least 10% of random sequencing start positions. In some embodiments, the extended sequencing flow order is selected to generate signal differences at more than two flow positions between two sequencing data sets (e.g., a test or target sequencing data set and a candidate or reference sequencing data set) associated with nucleic acid molecules differing by a SNP for about 60% to 87.5% of SNP permutations for at least 10% of random sequencing start positions. In some embodiments, the extended sequencing flow order is selected to generate signal differences at more than two flow positions between two sequencing data sets (e.g., a test or target sequencing data set and a candidate or reference sequencing data set) associated with nucleic acid molecules differing by a SNP for about 70% to 87.5% of SNP permutations for at least 10% of random sequencing start positions. In some embodiments, the extended sequencing flow order is selected to generate signal differences at more than two flow positions between two sequencing data sets (e.g., a test or target sequencing data set and a candidate or reference sequencing data set) associated with nucleic acid molecules differing by a SNP for about 80% to 87.5% of SNP permutations for at least 10% of random sequencing start positions.

In some embodiments, the extended sequencing flow order is selected to generate signal differences at more than two flow positions between two sequencing data sets (e.g., a test or target sequencing data set and a candidate or reference sequencing data set) associated with nucleic acid molecules differing by a SNP for about 50% to 87.5% of SNP permutations for at least 20% of random sequencing start positions. In some embodiments, the extended sequencing flow order is selected to generate signal differences at more than two flow positions between two sequencing data sets (e.g., a test or target sequencing data set and a candidate or reference sequencing data set) associated with nucleic acid molecules differing by a SNP for about 60% to 87.5% of SNP permutations for at least 20% of random sequencing start positions. In some embodiments, the extended sequencing flow order is selected to generate signal differences at more than two flow positions between two sequencing data sets (e.g., a test or target sequencing data set and a candidate or reference sequencing data set) associated with nucleic acid molecules differing by a SNP for about 70% to 87.5% of SNP permutations for at least 20% of random sequencing start positions. In some embodiments, the extended sequencing flow order is selected to generate signal differences at more than two flow positions between two sequencing data sets (e.g., a test or target sequencing data set and a candidate or reference sequencing data set) associated with nucleic acid molecules differing by a SNP for about 80% to 87.5% of SNP permutations for at least 20% of random sequencing start positions.

In some embodiments, the extended sequencing flow order is selected to generate signal differences at more than two flow positions between two sequencing data sets (e.g., a test or target sequencing data set and a candidate or reference sequencing data set) associated with nucleic acid molecules differing by a SNP for about 50% to 87.5% (or about 50% to about 80%) of SNP permutations for at least 30% of random sequencing start positions. In some embodiments, the extended sequencing flow order is selected to generate signal differences at more than two flow positions between two sequencing data sets (e.g., a test or target sequencing data set and a candidate or reference sequencing data set) associated with nucleic acid molecules differing by a SNP for about 60% to 87.5% (or about 60% to about 80%) of SNP permutations for at least 30% of random sequencing start positions. In some embodiments, the extended sequencing flow order is selected to generate signal differences at more than two flow positions between two sequencing data sets (e.g., a test or target sequencing data set and a candidate or reference sequencing data set) associated with nucleic acid molecules differing by a SNP for about 70% to 87.5% (or about 70% to about 80%) of SNP permutations for at least 30% of random sequencing start positions.

In some embodiments, the extended sequencing flow order is any one of the extended sequencing flow orders in Table 4. "Shift sensitivity" refers to the maximum sensitivity to generate signal differences at more than two flow positions between two sequencing data sets (e.g., a test or target sequencing data set and a candidate or reference sequencing data set) over all possible SNP permutations. "Maximum shift sensitivity" refers to refers to the maximum sensitivity to generate signal differences at more than two flow positions between two sequencing data sets (e.g., a test or target sequencing data set and a candidate or reference sequencing data set) over all possible SNP permutations at the highest fraction of flow phases at which that sensitivity is maintained.

TABLE 4

| Flow Cycle Order | Estimated Efficiency | Maximum Shift Sensitivity | Shift Sensitivity @ 5% of Flow Phases | Shift Sensitivity @ 10% of Flow Phases | Shift Sensitivity @ 20% of Flow Phases | Shift Sensitivity @ 30% of Flow Phases |
|---|---|---|---|---|---|---|
| T-C-A-G-A-T-G-C-A-T-G-C-T-A-C-G | 67.5% | 82.3% @ 19% | 82.3% | 82.3% | 75.0% | 66.7% |
| T-C-A-C-G-A-T-G-C-A-T-G-C-T-A-G | 67.5% | 83.3% @ 12% | 83.3% | 83.3% | 72.9% | 62.5% |
| T-C-A-T-G-C-A-T-G-C-T-A-C-G-A-G | 67.3% | 82.3% @ 12% | 82.3% | 82.3% | 72.9% | 67.7% |
| T-C-A-G-T-A-C-G-A-T-G-C-A-T-G-C | 67.3% | 82.3% @ 12% | 82.3% | 82.3% | 75.0% | 63.5% |
| T-C-A-G-T-C-G-A-T-G-A-C-T-A-G-C | 67.2% | 81.3% @ 12% | 81.3% | 81.3% | 74.0% | 69.8% |
| T-C-A-T-C-G-A-C-T-G-A-G-C-T-A-G | 67.2% | 81.3% @ 12% | 81.3% | 81.3% | 74.0% | 69.8% |
| T-C-G-T-A-G-C-T-G-A-C-A-T-G-C-A | 67.2% | 83.3% @ 12% | 83.3% | 83.3% | 75.0% | 67.7% |
| T-C-G-T-A-G-C-A-T-G-C-T-A-C-G-A | 67.0% | 79.2% @ 25% | 79.2% | 79.2% | 79.2% | 75.0% |
| T-C-A-T-G-C-A-G-T-C-G-A-C-T-A-G | 66.9% | 83.3% @ 19% | 83.3% | 83.3% | 75.0% | 68.8% |
| T-C-A-T-G-C-A-T-C-G-T-A-C-G-A-G-C-T-G-C-A-T-G-A-C-T-A-G | 66.7% | 86.5% @ 7% | 86.5% | 85.4% | 85.4% | 69.8% |
| T-C-G-A-C-T-G-T-A-G-C-T-A-G-C-A | 66.7% | 82.3% @ 19% | 82.3% | 82.3% | 75.0% | 66.7% |
| T-C-A-C-G-A-T-G-C-T-A-G-C-T-A-G | 66.5% | 82.3% @ 12% | 82.3% | 82.3% | 75.0% | 67.7% |
| T-C-A-G-T-A-C-G-A-T-G-C-T-A-C-G | 66.4% | 83.3% @ 19% | 83.3% | 83.3% | 75.0% | 68.8% |
| T-C-G-A-C-T-A-G-C-A-T-G-C-A-T-G | 66.0% | 81.3% @ 12% | 81.3% | 81.3% | 70.8% | 62.5% |
| T-A-C-G | 66.0% | 41.7% @ 100% | 41.7% | 41.7% | 41.7% | 41.7% |
| T-C-A-G-C-T-G-A-C-T-A-G-T-C-A-T-G-A-C-T-A-G-C-G-A-T-C-G | 65.7% | 87.5% @ 11% | 87.5% | 87.5% | 82.3% | 75.0% |
| T-C-T-A-G-C-A-T-G-A-C-T-G-A-C-G | 65.7% | 83.3% @ 12% | 83.3% | 83.3% | 71.9% | 63.5% |
| T-C-G-A-C-T-A-T-G-C-A-T-G-C-A-G | 65.5% | 81.3% @ 19% | 81.3% | 81.3% | 71.9% | 63.5% |
| T-C-G-A-C-T-G-C-A-T-C-G-A-T-G-C-A-G-T-A-C-T-A-G | 65.4% | 87.5% @ 12% | 87.5% | 87.5% | 82.3% | 74.0% |
| T-C-A-C-T-G-A-C-G-T-A-G-C-T-A-T-G-C-A-T-C-G-A-G | 65.3% | 84.4% @ 17% | 84.4% | 84.4% | 83.3% | 76.0% |

TABLE 4-continued

| Flow Cycle Order | Estimated Efficiency | Maximum Shift Sensitivity | Shift Sensitivity @ 5% of Flow Phases | Shift Sensitivity @ 10% of Flow Phases | Shift Sensitivity @ 20% of Flow Phases | Shift Sensitivity @ 30% of Flow Phases |
|---|---|---|---|---|---|---|
| T-C-A-T-G-C-T-A-G-C-T-A-G-T-A-C-G-A-C-T-G-A-G-C-A-T-C-G | 65.2% | 86.5% @ 11% | 86.5% | 86.5% | 82.3% | 78.1% |
| T-C-G-A-T-G-C-A-T-C-G-T-A-C-T-A-G-C-A-G-T-G-A-C | 65.2% | 87.5% @ 8% | 87.5% | 86.5% | 84.4% | 71.9% |
| T-C-A-T-G-A-G-C-T-A-G-C-A-T-C-G-T-A-C-T-G-A-C-G | 65.2% | 87.5% @ 8% | 87.5% | 86.5% | 81.3% | 70.8% |
| T-C-A-G-C-A-T-G-T-A-C-T-G-A-T-G-C-A-T-C-G-A-G-C-T-A-C-G | 65.0% | 87.5% @ 11% | 87.5% | 87.5% | 82.3% | 77.1% |
| T-C-A-G-T-A-C-T-A-G-C-A-T-G-C-G-A-T-C-G-T-A-G-C-T-G-A-C | 65.0% | 86.5% @ 11% | 86.5% | 86.5% | 78.1% | 74.0% |
| T-C-A-C-G-T-A-G-C-T-A-T-G-C-T-G-A-C-T-G-A-C-A-T-G-A-C-T-A-G-C-G | 64.6% | 85.4% @ 9% | 85.4% | 84.4% | 76.0% | 61.5% |
| T-C-A-G-C-T-A-T-G-A-C-T-G-A-G-C-A-T-C-G-T-A-C-G | 64.5% | 85.4% @ 12% | 85.4% | 85.4% | 77.1% | 74.0% |
| T-C-A-G-C-T-A-C-T-G-C-A-T-G-A-C-G-T-A-C-G-T-A-G-T-C-G-A | 64.5% | 87.5% @ 14% | 87.5% | 87.5% | 83.3% | 70.8% |
| T-C-A-G-A-C-T-A-G-C-G-A-T-G-C-A-T-G-T-C-T-A-G-T-C-A-C-G | 64.5% | 86.5% @ 11% | 86.5% | 86.5% | 83.3% | 62.5% |
| T-C-A-T-C-G-A-C-T-G-C-G-A-T-G-C-T-A-G-T-A-C-A-G | 64.4% | 85.4% @ 17% | 85.4% | 85.4% | 83.3% | 72.9% |
| T-C-A-C-G-T-A-C-T-G-A-C-A-T-G-C-A-T-G-C-T-A-G-T-A-G-C-G-A-T-C-G | 64.4% | 85.4% @ 9% | 85.4% | 84.4% | 83.3% | 72.9% |
| T-C-A-G-T-G-C-T-A-C-G-T-C-A-C-G-A-T-C-A-G-A-T-G-C-T-A-G | 64.4% | 86.5% @ 11% | 86.5% | 86.5% | 71.9% | 67.7% |
| T-C-A-G-C-G-A-T-G-A-C-T-A-G-C-T-A-C-G-T-C-A-T-G | 64.4% | 85.4% @ 17% | 85.4% | 85.4% | 84.4% | 66.7% |
| T-C-A-T-G-C-T-A-C-G-A-G | 64.4% | 81.3% @ 17% | 81.3% | 81.3% | 80.2% | 66.7% |
| T-C-A-T-G-A-C-G-T-A-C-G-A-C-T-C-A-T-G-C-A-G-T-G-C-T-A-G | 64.3% | 85.4% @ 11% | 85.4% | 85.4% | 82.3% | 75.0% |
| T-C-A-G-T-C-G-A-T-G-C-T-A-C-T-G-C-A-T-A-C-G-T-C-G-A-T-G-A-C-A-G | 64.3% | 87.5% @ 9% | 87.5% | 86.5% | 83.3% | 74.0% |
| T-C-G-A-T-G-C-T-A-C-A-G | 64.3% | 81.3% @ 17% | 81.3% | 81.3% | 80.2% | 66.7% |
| T-C-A-G-T-C-G-A-C-A-T-G-C-A-T-C-G-A-T-A-C-G-T-G-C-T-A-G-C-T-A-G | 64.2% | 87.5% @ 9% | 87.5% | 86.5% | 79.2% | 70.8% |

In some embodiments, the flow-cycle order induces a signal change at more than two flow positions for 50% or more of possible SNP permutations at 5% of random sequencing start positions. In some embodiments, the induced signal change is a change in signal intensity, or a new substantially zero (or new zero) or a new substantially non-zero (or new non-zero) signal. In some embodiments, the induced signal change is a new substantially zero (or new zero) or a new substantially non-zero (or new non-zero) signal. In some embodiments, the flow-cycle order has an efficiency of 0.6 or more base incorporations per flow. In some embodiments, the flow-cycle is any one of the flow-cycle orders listed in Table 4.

Re-Phasing Flows

One or more re-phasing flows may be used as or within the second region to re-phase (i.e., synchronize) parallel sequencing reactions within a sequencing cluster. A sequencing cluster includes a plurality of polynucleotide copies closely attached on a common surface (e.g., a bead or a flowcell). The cluster may be formed, for example, by attaching a polynucleotide to the surface and amplifying the attached polynucleotide (for example, by bridge amplification). Sequencing data can be collected from the sequencing cluster as a whole, as a primer hybridized to each of the polynucleotides is extended simultaneously by incorporating nucleotides based on an identical template. However, the chemical process of incorporating nucleotides into an extending prime is often imperfect, causing desynchronization among strands within a sequencing cluster. That is, certain primers may lag relative to other extended primers within the cluster. Desynchronization may result in signal degradation, and therefore reduced accuracy, when detecting the presence or absence of nucleotide incorporation into the extending primer as the read length increases. Resynchronization can result in counteracting the signal loss, which allows for a longer effective read length. To re-phase the sequencing reaction, the primer is extended through the second region using one or more re-phasing flows wherein a mixture of at least two (e.g., two or three) different types of nucleotide bases are used in a plurality of steps of the second region flow order. The nucleotides incorporated during the re-phasing flow(s) may not be detected in some embodiments, which would result in a gap in the resulting read. However, this read gap can be managed when the sequences are aligned to a reference or other sequence. By including such "catch up flows," the lagging primers can catch up to the other extended primers within the cluster.

A method of resynchronizing a sequencing cluster comprising a plurality of polynucleotide copies (for example, within a sequencing cluster) can include extending a primer hybridized to the polynucleotide copies using a re-phasing flow order, wherein a mixture of at least two different types of nucleotide bases are used in at least one step of the re-phasing flow order. In some embodiments, a method of synchronizing sequencing primers within a sequencing cluster, comprises (a) hybridizing primers to polynucleotide copies within a sequencing cluster; (b) extending the primers through a first region of the polynucleotide copies using labeled nucleotides according to a first region flow cycle; (c) extending the primers through a second region of the polynucleotide copies using one or more re-phasing flows, wherein a mixture of at least two different types of nucleotide bases are used in each of the one or more re-phasing flows; and (d) extending the primers through a third region of the polynucleotide copies using labeled nucleotides according to a third region flow cycle.

A method of generating a sequencing read from a plurality of polynucleotide copies (for examples, within a sequencing cluster) can include the resynchronization method. For example, a method of generating a sequencing read from a plurality of polynucleotide copies may include (a) hybridizing the polynucleotide copies to a primer to form a hybridization template; (b) generating sequencing data associated with a sequence of a first region of the polynucleotide copies by extending the primer using labeled nucleotides, an detecting the presence or absence of an incorporated labeled nucleotide; (c) further extending the primer extended in step (b) through a second region using nucleotides provided in one or more re-phasing flows, wherein a mixture of at least two different types of nucleotide bases are used in each of the one or more re-phasing flows; and (d) generating sequencing data associated with a sequence of a third region of the polynucleotide by further extending the primer extended in step (c) using labeled nucleotides, and detecting the presence or absence of an incorporated labeled nucleotide.

The re-phasing flow order (or re-phasing flow cycle) includes one or more steps that allow the lagging primer to catch up to the leading primer in the sequencing cluster. At least one of the steps (e.g., 1, 2, 3, 4, or more) in the re-phasing flow order includes a mixture of two or more (e.g., three) different types of nucleotide bases. In some embodiments, the re-phasing flow order comprises 1, 2, 3, 4, 5, or more flows, each comprising two or three different types of nucleotide bases.

The re-phasing flow order is configured to increase the portion of synchronized extending primers after the re-phasing flow order. In some embodiments, the re-phasing flow order comprises, in any order, (i) a flow step comprising a mixture comprising A, C, and G nucleotides and omitting T (and/or U) nucleotides (also referred to as a "not T" (and/or "not U") step); (ii) a flow step comprising a mixture comprising T (and/or U), C, and G nucleotides and omitting A nucleotides (also referred to a "not A" step); (iii) a flow step comprising a mixture comprising T (and/or U), A, and G nucleotides and omitting C nucleotides (also referred to as a "not C" step); and (iv) a flow step comprising a mixture comprising T (and/or U), A, and C nucleotides and omitting G nucleotides (also referred to as a "not G" step).

Other re-phasing flows can be determined. By way of example, in some embodiments, the re-phasing flows (in a re-phasing flow order) comprises, one or more of, in any order, (i) a flow step comprising a mixture comprising A and C nucleotides and omitting G and T (and/or U) nucleotides; (ii) a flow step comprising a mixture comprising T (and/or U) and G nucleotides, and omitting A and C nucleotides; (iii) a flow step comprising a mixture comprising A and G nucleotides and omitting T (and/or U) and C nucleotides; (iv) a flow step comprising a mixture comprising T (and/or U) and C nucleotides and omitting A and G nucleotides; (v) a flow step comprising a mixture comprising A and T (and/or U) nucleotides and omitting G and C nucleotides; (vi) a flow step comprising a mixture comprising C and G nucleotides and omitting A and T (and/or U) nucleotides; (vii) a flow step comprising a mixture comprising A, G, and C nucleotides and omitting T nucleotides; (viii) a flow step comprising a mixture comprising T (and/or U), A, and G nucleotides and omitting C nucleotides; (ix) a flow step comprising a mixture comprising C, T (and/or U), and A nucleotides and omitting G nucleotides; and/or (x) a flow step comprising a mixture of G, C, and T (and/or U) nucleotides and omitting A nucleotides.

Including a mixture of all four types of non-terminating nucleotides (i.e., a mixture comprising A, C, G, and T (and/or U)) can result in uncontrolled primer extension. However, a mixture of all four types of nucleotides, wherein three base types are non-terminating nucleotides and one base type includes a reversible terminator, can be used in a re-phasing flow order. For example, in some embodiments, the re-phasing flow order comprises (i) a flow step comprising a mixture comprising (or consisting of) non-terminating A nucleotides, non-terminating C nucleotides, non-terminating G nucleotides, and T (and/or U) nucleotides comprising a reversible terminator; or (ii) a flow step comprising a mixture comprising (or consisting of) non-terminating T (and/or U) nucleotides, non-terminating A nucleotides, non-terminating C nucleotides, and G nucleotides comprising a reversible terminator; or (iii) a flow step comprising a mixture comprising (or consisting of) non-terminating G nucleotides, non-terminating T (and/or U) nucleotides, non-terminating A nucleotides, and C nucleotides comprising a reversible terminator; or (iv) a flow step comprising a mixture comprising (or consisting of) non-terminating C nucleotides, non-terminating G nucleotides, non-terminating T (and/or) nucleotides, and A nucleotides comprising a reversible terminator. The primer is extended by incorporating nucleotides based on the template strand until a nucleotides comprising a reversible terminator is incorporated, which synchronizes extending primers within the sequencing cluster at the base with the reversible terminator. The reversible terminator can then be removed, and the sequencing process can then proceed with the synchronized primers.

In some embodiments, a re-phasing flow order comprises (i) in any order, a first re-phasing flow comprising a mixture of C, G, and T (and/or U) bases (omitting A bases), and a second re-phasing flow order comprising a mixture of A, C, and G bases (omitting T and/or U bases).

The methods described herein for synchronizing extending primers within a sequencing cluster can be used in sequencing-by-synthesis methods that use non-terminating nucleotides to extend the primer. In some embodiments, the method is used in combination with other methods described herein, such as the fast-forward sequencing methods described herein (e.g., sequencing methods that generate a "dark" region).

Mapping a Coupled Sequencing Read Pair to a Reference Sequence

A coupled sequencing read pair can be mapped to a reference sequence, which may or may not include a test variant of interest. The sequencing data for the first region or the third region can be used to derive the sequence of the first region or the third region, respectively. The first region or a portion of the first region, or the third region or a portion of the third region, can be mapped to the reference sequence. The distance between the first region and the third region (i.e., the length of the second region) can be determined or estimated, providing an approximate locus for the unmapped third or first region. Using the approximate locus, the unmapped first or third region can then be readily mapped to the reference sequence.

A mapped sequence refers to an alignment of one sequence (such as the sequence of a region or a portion thereof) to another sequence (such as a reference sequence). A mappable sequence is a sequence (such as a sequence of a region or portion thereof) that may be mapped another sequence (such as a reference sequence) in accordance with a selected mapping threshold (i.e., a mapping score). An unmappable sequence, therefore, is a sequence that is not mappable to the other sequence in accordance with the selected mapping threshold (mapping score). The score may be predetermined (i.e., selected prior to mapping) based on an error risk tolerance. The Smith-Waterman algorithm may be used when mapping one sequence to another, for example, and the mapping threshold can be selected to distinguish a "mappable" sequence from an "unmappable" sequence. Bay way of example, the mapping score threshold may be +5 or higher, +6 or higher, +8 or higher, +10 or higher, +12 or higher, +14 or higher, +16 or higher, +18 or higher, or +20 or higher with a matching score of +1, a mismatch score of −1, a gap opening score of −2, and a gap extension score of −2. Other scores or penalty scores may be selected by one skilled in the art.

A sequence, such as one or more regions of a coupled sequencing read pair, can be mapped with any suitable mapping software, such as GATK, Bowtie, Bowtie2, BWA, BWA-MEM, Novoalign, SOAP2, SOAP3, and others including other Burrows-Wheeler transform (BWT)-based aligners. See for example, Miller et al., *Assembly algorithms for next-generation sequencing data*, Genomics, vol. 95, pp. 315-327 (2010); Chaisson et al., *De novo fragment assembly with short mate-paired reads: Does the read length matter?* Genome Research, vol. 19, pp. 336-346 (2009); Mielczarek et al., *Review of alignment and SNP calling algorithms for next-generation sequencing data*, J. Appl. Genetics, vol. 57, pp. 71-79 (2016); Nielsen et al., *Genotype and SNP calling from next-generation sequencing data*, Nature Reviews Genetics, vol. 2, pp. 443-451 (2011); and Hwang et al., *Systematic comparison of variant calling pipelines using gold standard personal exome variants, Sci Rep., vol.* 5, 17875 (2015); each of which is incorporated herein by reference for all purposes.

The use of distance information to approximate the locus of a region of the polynucleotide to the reference sequence is useful for detecting structural variants (such as insertions or deletions) within the second region of the polynucleotide, or to resolve multiple mappable loci within the genome (for example, when the first region or the third region includes a repeat region or other non-unique sequence). Distance information, as discussed herein, relates to the amount of space between two points (e.g., the start and end of a region), and can be considered in different frames of reference. For example, distance information in physical space can refer to a number of bases or a physical distance (e.g., a number of micrometers in one-dimensional space if the polynucleotide was linearly position). Distance information in a sequencing data space (e.g., a flowgram space) can refer to a number of flow steps used to extend the primer within the space with a given flow order. The distance information in physical space and the distance information in a sequencing data space are analytically interchangeable if the sequence (or reference sequence) and the flow order are known.

The distance information is indicative of the length of the second region, although need not be the precise length of the second region because the unmapped region is ultimately mapped within a location approximated by the distance information. In one example, the distance information is determined using the second region flow order (or information associated with the second region flow order) and a probability distribution of bases in the second region. The probability distribution of bases in the second region may be, for example, an assumed distribution of bases throughout the genome, or may be a more localized probability based on the mapped locus of the first region or third region. The information associated with the second region flow order, may be, for example, a number different types of nucleotide bases simultaneously used to extend the primer through the second region. By way of example, using three-base flow steps in repeating cycles to extend the primer within the second region (for example, using cycle steps of (not A)-(not C)-(not T)-(not G), with each cycle step including the three other bases) and assuming a distribution of bases in the second region approximately the same as the genome as a whole, the primer is expected to be extended by approximately 4.7 bases for each step in the cycle. Thus, the length of the second region can be approximated as 4.7 times the number of steps in the second region flow order.

In some embodiments, the distance information is derived from expected reference sequencing data for the second region. As discussed herein, the expected reference sequencing data for the second region can be determined using the reference sequence and the second region flow order. Once the first or third region of the polynucleotide is mapped to the reference sequence, the expected sequence information, including the expected sequence length is determined, which provides the length between the first region and the third region of the polynucleotide.

The distance information can be used to map the coupled sequencing read pair to a reference sequence when more than one mappable positions are available within the reference sequence. For example, in some embodiments, the first region can be mapped to the reference sequence with a high confidence, but the third region may map to a plurality of different locations within the reference sequence. In some embodiments, the third region can be mapped to the reference sequence with a high confidence, but the first region may map to a plurality of different locations within the reference sequence. In some embodiments, both the first region and the third region can be mapped to a plurality of different locations within the reference sequence. The correct position pair for the first region and the second region mapped to the reference sequence can be selected using the distance information for the second region. For example, a method of mapping a coupled sequencing read pair to a reference sequence can include mapping a first region (or portion thereof) and a third region (or portion thereof) of a coupled sequencing read pair to a reference sequence at two or more different position pairs comprising a first position and a second position. Distance information indicative of the length of the second region of the polynucleotide can then be compared to distance information indicative of the length between the first position and the second position. If the compared distance information approximate each other or match, the correct position pair can then be selected. If, however, the length of the second region is significantly different from the distance between the first position and the second position, that position pair can be rejected.

Figure 3:
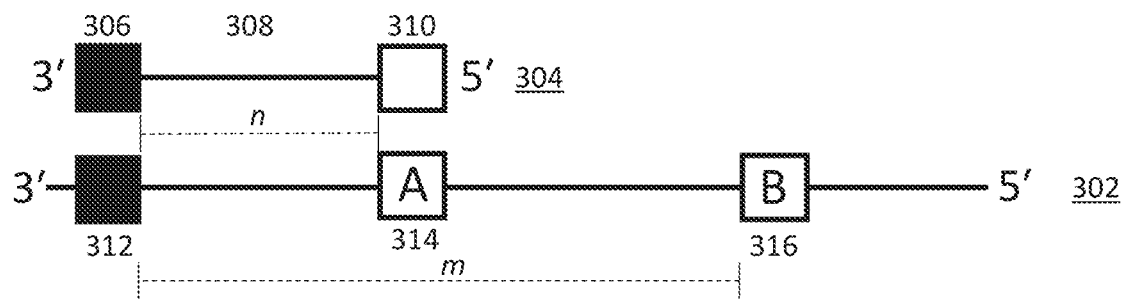
FIG. 3 illustrates how a coupled sequencing read pair is mapped to a reference sequence using distance information indicative of the length of the second region of the coupled sequencing read pair when the third region of the coupled sequencing read pair maps to two different loci.

FIG. 3 illustrates how a coupled sequencing read pair is mapped to a reference sequence using distance information indicative of the length of the second region of the coupled sequencing read pair. The coupled sequencing read pair 304 includes first region 306, a second region 308 and a third region 310. The first region 306 can map to the reference first region 312 of a reference sequence 302, but the third region 310 can map to both reference third region, option A, 314, and the reference third region, option B, 316. The distance between the end of the reference first region 312 and the start of the reference third region, option A, 314 is n bases in length (based on the reference sequence), and the distance between the end of the reference first region 312 and the start of the reference third region, option B, 316 is m bases in length (based on the reference sequence). The distance information for the second region indicates that the length of the second region is approximately n bases in length. Therefore, it can be concluded that the third region 310 properly maps to reference third region, option A, 314. A similar analysis may be performed even if there are multiple mappable loci for the first region and/or multiple mappable loci for the third region.

Figure 4:
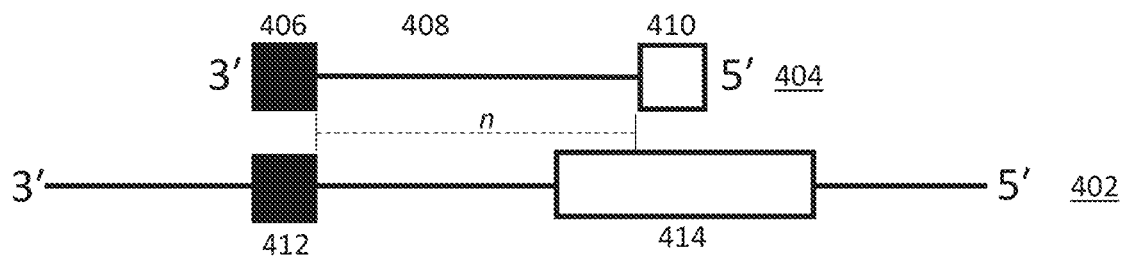
FIG. 4 illustrates how a coupled sequencing read pair is mapped to a reference sequence using distance information indicative of the length of the second region of the coupled sequencing read pair when the third region of the coupled sequencing read pair maps to a repeat region.

Furthermore, the distance information can be used to map the coupled sequencing read pair to a reference sequence when the first region or the third region cannot be definitively mapped to an exact location because of a repeat region at the locus of the first region or the third region. FIG. 4 illustrates how a coupled sequencing read pair is mapped to a reference sequence using distance information indicative of the length of the second region of the coupled sequencing read pair when the third region of the coupled sequencing read pair maps to a repeat region. FIG. 4 shows a reference sequence 402 and a coupled sequencing read pair 404. The coupled sequencing read pair includes first region 406, a second region 408 and a third region 410. The first region 406 can map to a specific locus within the reference first region 412, but the third region 410 can map anywhere within a repeat region 414. By knowing the length of the second region 408, the third region 410 can be more accurately mapped within the repeat region 414. For example, if the length of the second region 408 is approximately n bases in length, this distance information can be used to position the third region 410 once the first region 406 has been mapped. Similarly, this method can be used when the third region can be precisely mapped but the first region maps within a repeat region.

Detection of a Structural Variant

The coupled sequencing read pairs generated from a polynucleotide derived from genome can be used to detect a variant, such as a structural variant within the genome. Structural variants can include insertion, deletion, inversion, and chromosomal fusion variants, which may located within the first, second, or third region of the polynucleotides, or may be located at a position bridging the first, second or third region of the polynucleotide.

An insertion in a genome may be of any size, such as between 1 base in length to hundreds or thousands of kilobases or more in length. Further, the insertion may be and endogenous insertion (that is, a sequence inserted into a locus originating from elsewhere in the subject's genome), or may be an exogenous insertion (such as a sequence inserted into a locus originating from a source other than the subject's genome, such as a viral genome inserted into the subjects genome). Exogenous insertions result in nucleic acid sequences that are not present within the reference sequence, posing an additional challenge for detecting or locating exogenous insertion variants within the subject's genome. The methods described herein can be used to detect and/or locate an exogenous insertion, among other structural variants.

Figure 5:
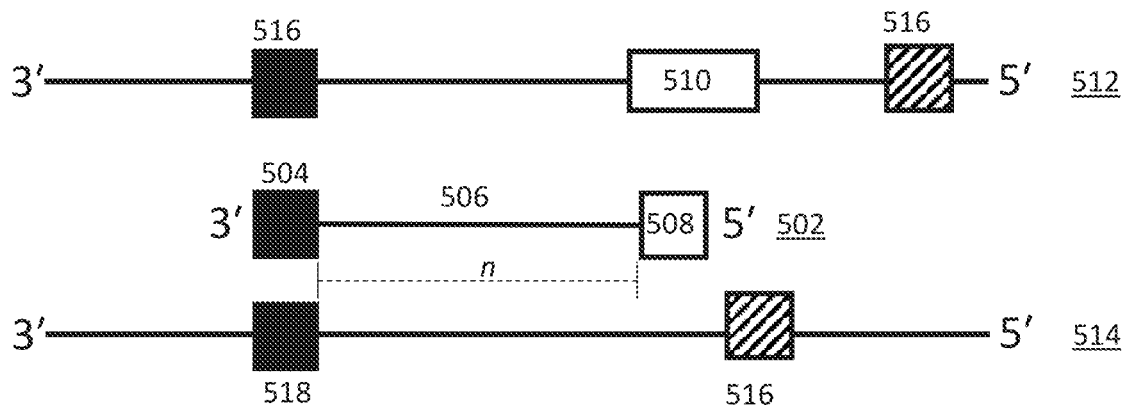
FIG. 5 illustrates a schematic for how a coupled sequencing read pair can be used to detect an insertion in a subject's genome.

In one example, a method of detecting a structural variant (such as an exogenous insertion) within a genome using a coupled sequencing read pair includes mapping the first region (or portion thereof) of the coupled sequencing read pair to a reference sequence, and attempting to map the third region (or portion thereof) to the reference sequence. If the third region (or portion thereof) is unmappable, then the presence of an exogenous insertion can be identified. This is because the reference sequence does not include a sequence corresponding to the third region. Similarly, a method of detecting an exogenous insertion within a genome using a coupled sequencing read pair can include mapping the third region (or portion thereof) of the coupled sequencing read pair to a reference sequence, and attempting to map the first region (or portion thereof) to the reference sequence. If the first region (or portion thereof) is unmappable, then the presence of an exogenous insertion can be identified. This is because the reference sequence does not include a sequence corresponding to the first region. Further (and in either example), the locus of the exogenous insertion within the reference sequence can be determined based on expected distance information indicative of the length of the second region. FIG. 5 illustrates a schematic for an exemplary method of detecting an exogenous insertion. The coupled sequencing read pair 502 includes a first region 504, a second region 506, and a third region 508, with the second region 506 between the first region 504 and the third region 508. The third region 508 includes an exogenous insertion element 510 present in the subject's genome 512, although not present in the reference sequence 514. Reference element 516 is present in both the subject's genome 512 and the reference sequence 514, although is spaced differently from the reference first region 518. The first region 504 maps to reference first region 518 within the reference sequence. However, the third region 508 does not have a corresponding region on which to map (i.e., it is unmappable) within the reference sequence 514. This indicates that the sequence of the third region 508 is the result of an exogenous insertion within the subject's genome. Distance information for the second region 506 can also be used to determine the locus of the exogenous genome relative to the reference first region 518. That is, if the second region 506 is approximately n bases in length, the exogenous insert is positioned approximately n bases from the end of the first region 504.

In another example, the coupled sequencing read pair can be used to detect a structural variant (such as an insertion, deletion, inversion, or chromosomal fusion) using expected sequencing data, and comparing the generated sequencing data to expected sequencing data. For example, one of the first region (or a portion thereof) or the third region (or portion thereof) of a coupled sequencing read pair can be mapped to a reference sequence. A locus within the reference sequence for the unmapped first region (or portion thereof) or the unmapped third region (or portion thereof) can be determined using distance information indicative of the length of the second region. The distance information can be determined, for example, as described herein. Once the locus for the unmapped first region (or portion thereof) or unmapped third region (or portion thereof) is determined, expected sequencing data reference sequence at the locus can be determined. For example, the expected sequence data may be determined based on the sequence of the second region, the second region flow order, information related to the sequence of the unmapped region, and the unmapped region flow order. The expected sequencing data can then be compared to the generated sequencing data of the unmapped region. A difference between the sequencing data of the unmapped region and the expected sequencing data indicates a structural variant at the locus.

Figure 6:
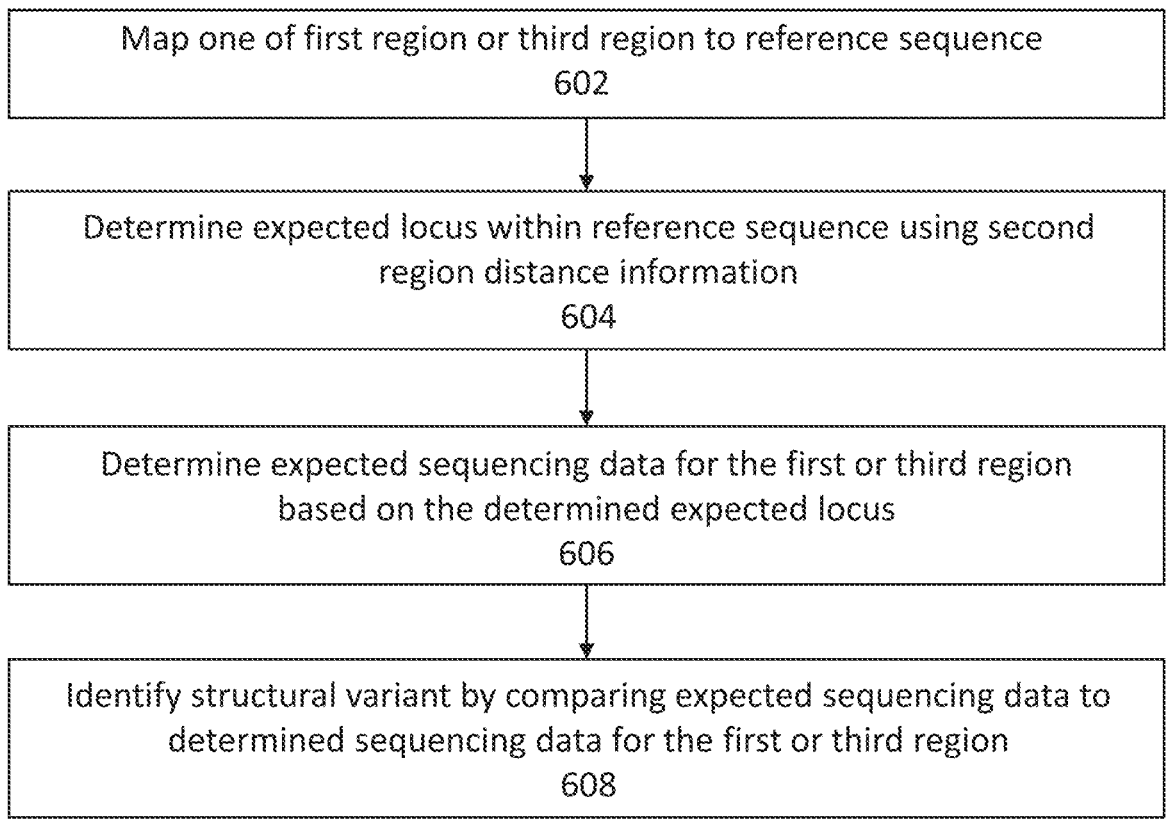
FIG. 6 illustrates an exemplary method for detecting a structural variant using a coupled sequencing read pair.

FIG. 6 illustrates an exemplary method for detecting a structural variant using a coupled sequencing read pair. At step 602, one of the first region or portion thereof (or the third region or portion thereof) is mapped to a reference sequence. At step 604, an expected locus within a reference sequenced is determined for the third region or portion thereof (or first region or portion thereof). This is, if the first region or portion thereof is mapped during step 602, the expected locus for the third region or portion thereof is determined at step 604, and if the third region or portion thereof is mapped during step 602, the expected locus for the first region or portion thereof is determined at step 604. At step 606, an expected sequencing data at the determined expected locus for the third region or portion thereof (or the first region or portion thereof) is determined. At step 608, the expected sequencing data for the third region or portion thereof (or the first region or portion thereof) is compared to determined sequencing data for the third region or portion thereof (or the first region or portion thereof), wherein a difference between the determined sequencing data and the expected sequencing data indicates a structural variant.

Figure 7:
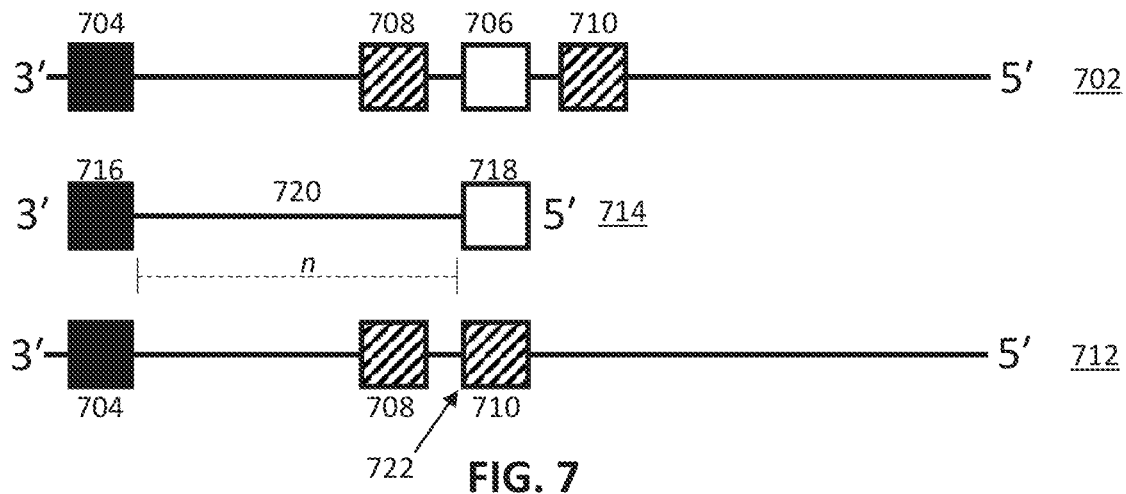
FIG. 7 illustrates a schematic for using a coupled sequencing read pair for detecting a structural variant in the subject's genome, wherein the structural variant is an insertion.

FIG. 7 illustrates a schematic for using a coupled sequencing read pair for detecting a structural variant in the subject's genome, wherein the structural variant is an insertion. The subject's genome 702 includes a first region 704 and an insertion 706 between a first reference region 708 and a second reference region 710. The reference sequence 712 includes the first region 704, the first reference region 708, and the second reference region 710, but does not include the insertion 706 between the first reference region 708 and the second reference region 710 (the insertion may correspond to a region found in another portion of the reference region, or may be an entirely exogenous sequence). The coupled sequencing read pair 714 includes a first region 716 (corresponding to first region 704) and a third region 718 (corresponding to the insertion 706), which separate a second region 720. The first region 716 of the coupled sequencing read pair 714 maps to the first region 704 of the reference sequence 712. Distance information indicates the length of the second region 720 of the coupled sequencing read pair 714 as approximately n bases in length. Therefore, the start of the expected locus 722 for the third region 718 is determined to start approximately n bases from the end of the first region 704. Expected sequencing data can then be determined for the expected locus as described herein. For example, expected sequencing data may be determined for the expected locus using the reference sequence 712 (for example, the reference sequence between the first region 704 to and/or including the expected locus), the flow order for the second region, and the flow order for the third region. In the example illustrated in FIG. 7, the expected sequencing data corresponds to sequencing data that would have been obtained if the third region 718 was the second reference region 710, as the second reference region 710 is at the expected locus. If the expected sequencing data for the expected locus differs from the generated sequencing data for the third region 718 of the coupled sequencing read pair 714 (which is the circumstance of the example illustrated in FIG. 7), then the structural variant is detected.

Figure 8:
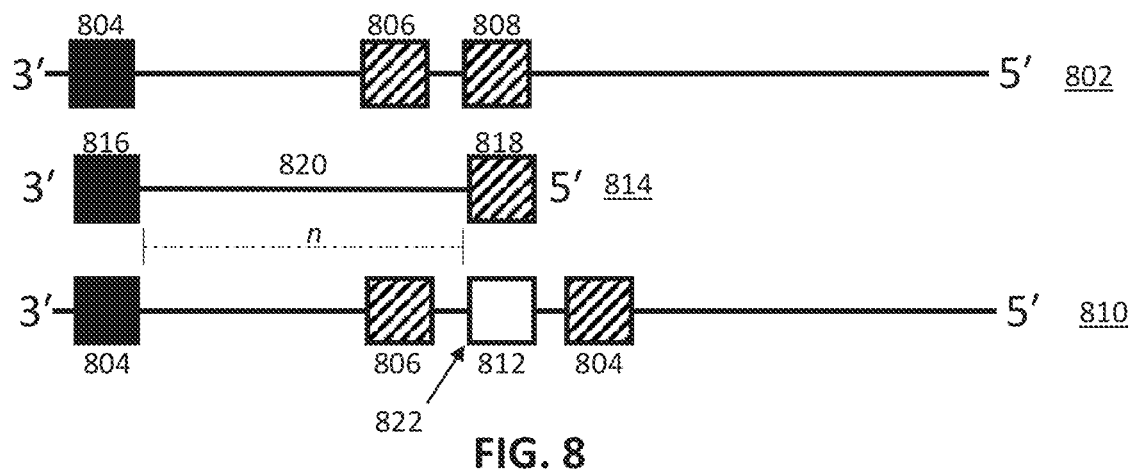
FIG. 8 illustrates a schematic for using a coupled sequencing read pair for detecting a structural variant in the subject's genome, wherein the structural variant is a deletion.

FIG. 8 illustrates a schematic for using a coupled sequencing read pair for detecting a structural variant in the subject's genome, wherein the structural variant is a deletion. The subject's genome 802 includes a first region 804, first reference region 806, and a second reference region 808. The reference sequence 810 includes the first region 804, the first reference region 806, and the second reference region 808, along with an additional region 812 positioned between the first reference region 806 and the second reference region 808. Although the additional region 812 is present in the reference sequence 810, the additional region 812 has been deleted from the subject's genome 802. The coupled sequencing read pair 814 includes a first region 816 (corresponding to first region 804) and a third region 818 (corresponding to the second reference region 808), which separate a second region 820. The first region 816 of the coupled sequencing read pair 814 maps to the first region 804 of the reference sequence 810. Distance information indicates the length of the second region 820 of the coupled sequencing read pair 814 as approximately n bases in length. Therefore, the start of the expected locus 822 for the third region 818 is determined to start approximately n bases from the end of the first region 804. Expected sequencing data can then be determined for the expected locus as described herein. For example, expected sequencing data may be determined for the expected locus using the reference sequence 812 (for example, the reference sequence between the first region 804 to and/or including the expected locus), the flow order for the second region, and the flow order for the third region. In the example illustrated in FIG. 8, the expected sequencing data corresponds to sequencing data that would have been obtained if the third region 818 was the additional region 812 (deleted in the subject's genome), as the additional region 812 is at the expected locus. If the expected sequencing data for the expected locus differs from the generated sequencing data for the third region 818 of the coupled sequencing read pair 814 (which is the circumstance of the example illustrated in FIG. 8), then the structural variant is detected.

Figure 9:
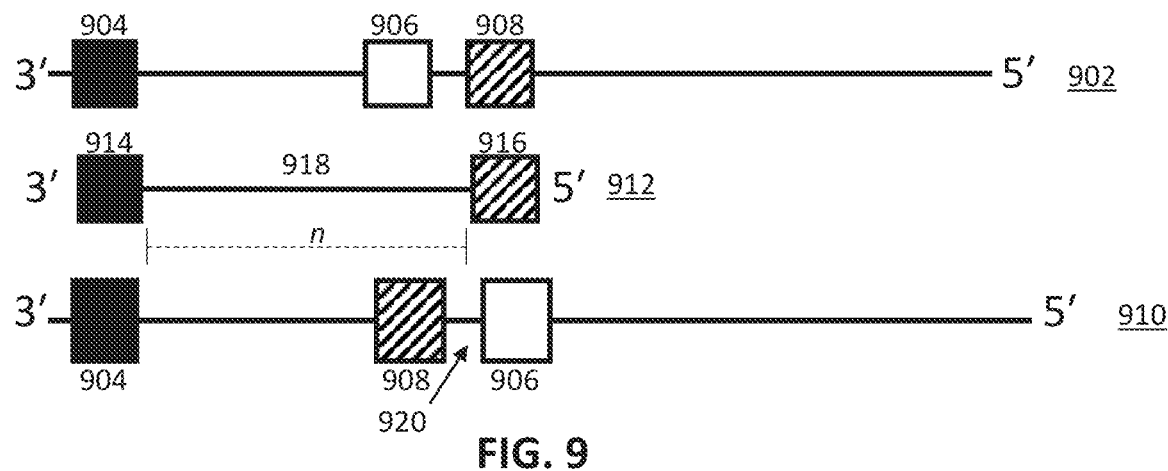
FIG. 9 illustrates a schematic of using a coupled sequencing read pair for detecting a structural variant in the subject's genome, wherein the structural variant is an inversion.

FIG. 9 illustrates a schematic of using a coupled sequencing read pair for detecting a structural variant in the subject's genome, wherein the structural variant is an inversion. The subject's genome 902 includes a first segment 904, a second segment 906, and a third segment 908. The reference sequence 910 also includes the first segment 904, the second segment 906, and the third segment 908. However, in the reference sequence 910, the second segment 906 is proximal to the 5' end relative to the third segment 908, whereas in the subject's genome 902, the second segment 906 is proximal to the 3' end relative to the third segment 908. Thus, the second segment 906 and the third segment 908 in the subject's genome 902 are inverted relative to the reference sequence 910. The coupled sequencing read pair 912 includes a first region 914 (corresponding to first segment 904) and a third region 916 (corresponding to the third segment 908), which separate a second region 918. The first region 914 of the coupled sequencing read pair 912 maps to the first segment 904 of the reference sequence 910. Distance information indicates the length of the second region 918 of the coupled sequencing read pair 912 as approximately n bases in length. Therefore, the start of the expected locus 920 for the third segment 908 is determined to start approximately n bases from the end of the first segment 904. Expected sequencing data can then be determined for the expected locus as described herein. For example, expected sequencing data may be determined for the expected locus using the reference sequence 910 (for example, the reference sequence between the first segment 904 to and/or including the expected locus), the flow order for the second region, and the flow order for the third region. In the example illustrated in FIG. 9, the expected sequencing data corresponds to sequencing data that would have been obtained if the third region 916 corresponded with the second segment 906, as the second segment 906 (and not the third segment 908) is at the expected locus in the reference sequence 910. If the expected sequencing data for the expected locus differs from the generated sequencing data for the third region 916 of the coupled sequencing read pair 912 (which is the circumstance of the example illustrated in FIG. 9), then the structural variant is detected.

Figure 10:
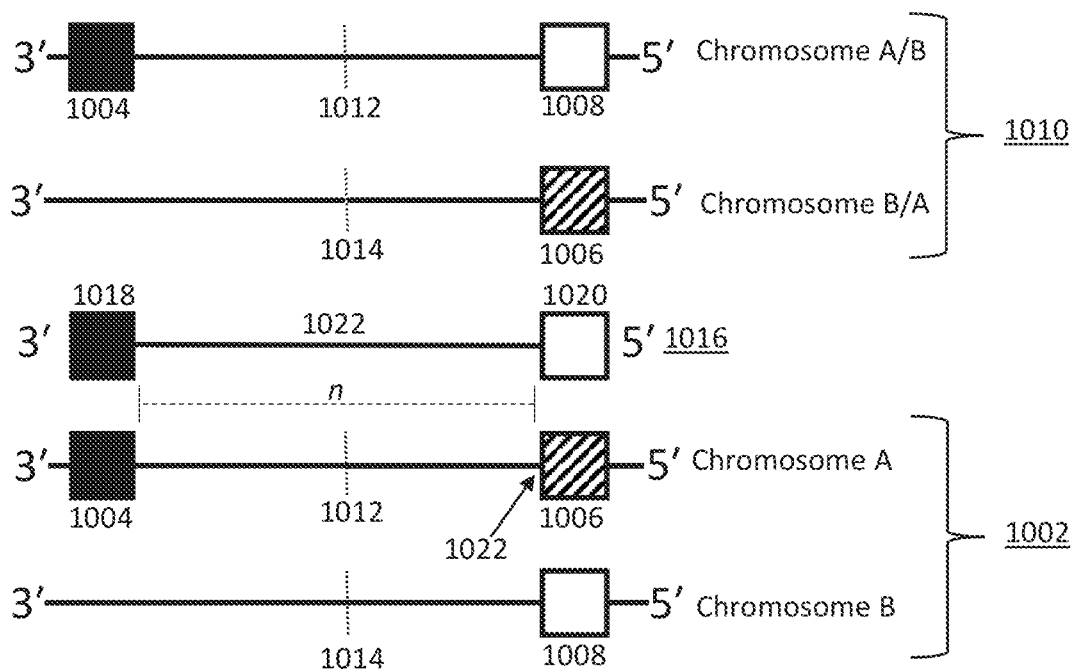
FIG. 10 illustrates a schematic for using a coupled sequencing read pair for detecting a structural variant in the subject's genome, wherein the structural variant is a chromosomal fusion.

FIG. 10 illustrates a schematic for using a coupled sequencing read pair for detecting a structural variant in the subject's genome, wherein the structural variant is a chromosomal fusion. A chromosomal fusion results from a chromosomal rearrangement event, wherein a portion of a chromosome fuses to another portion of a chromosome (either the same chromosome or a different chromosome). The reference sequence 1002 includes Chromosome A, which includes first segment 1004 and second segment 1006, and Chromosome B, which includes third segment 1008. The subject's genome 1010 includes a chromosomal fusion of Chromosome A and Chromosome B at points 1012 and 1014 of the reference genome 1002. This results in Chromosome A/B, which includes the 3' end of Chromosome A and the 5' end of Chromosome B, and Chromosome B/A, which includes the 3' end of Chromosome B and the 5' end of Chromosome A. Thus, Chromosome A/B includes first segment 1004 and third segment 1008, and Chromosome B/A includes second segment 1006. A coupled sequencing read pair 1016 is derived from Chromosome A/B of the subject's genome 1010, and includes a first region 1018 (corresponding to first segment 1004) and a third region 1020 (corresponding to the third segment 1008), which separate a second region 1022. The first region 1018 of the coupled sequencing read pair 1016 maps to the first segment 1004 of the reference sequence 1002. Distance information indicates the length of the second region 1022 of the coupled sequencing read pair 1016 as approximately n bases in length. Therefore, the start of the expected locus 1024 for the third segment 1020 is determined to start approximately n bases from the end of the first segment 1004. Expected sequencing data can then be determined for the expected locus as described herein. For example, expected sequencing data may be determined for the expected locus using Chromosome A of the reference sequence 1002 (for example, the reference sequence between the first segment 1004 to and/or including the expected locus, second segment 1006), the flow order for the second region 1022, and the flow order for the third region 1020. In the example illustrated in FIG. 10, the expected sequencing data corresponds to sequencing data that would have been obtained if the third region 1020 corresponded with the second segment 1006, as the second segment 1006 (and not the third segment 1008) is at the expected locus in the reference sequence 1002. If the expected sequencing data for the expected locus differs from the generated sequencing data for the third region 1020 of the coupled sequencing read pair 1016 (which is the circumstance of the example illustrated in FIG. 10), then the structural variant is detected.

The junction of the structural variant (e.g., the insertion, deletion, chromosomal fusion, or inversion) relative to the reference sequence need not span the entirety of the first region or the third region of the coupled sequencing read pair. In some embodiments, at least a portion of the structural variant terminates within the first region or the third region of the coupled sequencing read pair. The expected sequencing data will still differ from the determined sequencing data for the first or third region.

Detection of a Variant within the Second Region

In some embodiments, the coupled sequencing read pair is used to detect a variant within the second region, even though the incorporation of nucleotides into the primer extended through the second region need not be detected. Detectable variants include structural variants (such as an insertion, deletion, inversion, or chromosomal fusion) or a single nucleotide polymorphism (SNP).

A method of detecting a structural variant (e.g., chromosomal fusion, inversion, insertion, or deletion) can include mapping both a first region (or portion thereof) and a third region (or portion thereof) of a coupled sequencing read pair to a reference sequence. Distance information for an inversion occurring completely within the second region is generally considered in reference to the second region flow order (e.g., in flowgram space), whereas distance information for a chromosomal fusion, insertion, or deletion not occurring completely in the second region (e.g., at least partially in the first region or third region) can be considered in reference to a physical space or the second region flow order. Distance information between the first region mapped to the reference sequence and the third region mapped to the reference sequence (i.e., mapped distance information) can be determined. The mapped distance information is indicative of the distance between the mapped position of first region mapped to the reference sequence and the mapped position of the third region mapped to the reference sequence, for example a number of bases between the first and third mapped regions. Expected distance information can also be determined which is indicative of the length of the second region of the coupled sequencing read pair (for example using the flow order for the second region and the reference sequence, or as otherwise described herein). A comparison between the expected distance information and the mapped distance information can be used to detect the structural variant. For example, if the expected distance is shorter than the mapped distance, then a structural variant such as an insertion or a chromosomal fusion variant within the subject's genome is indicated. If the expected distance is longer than the mapped distance, then a deletion variant within the subject's genome is indicated.

Figure 11:
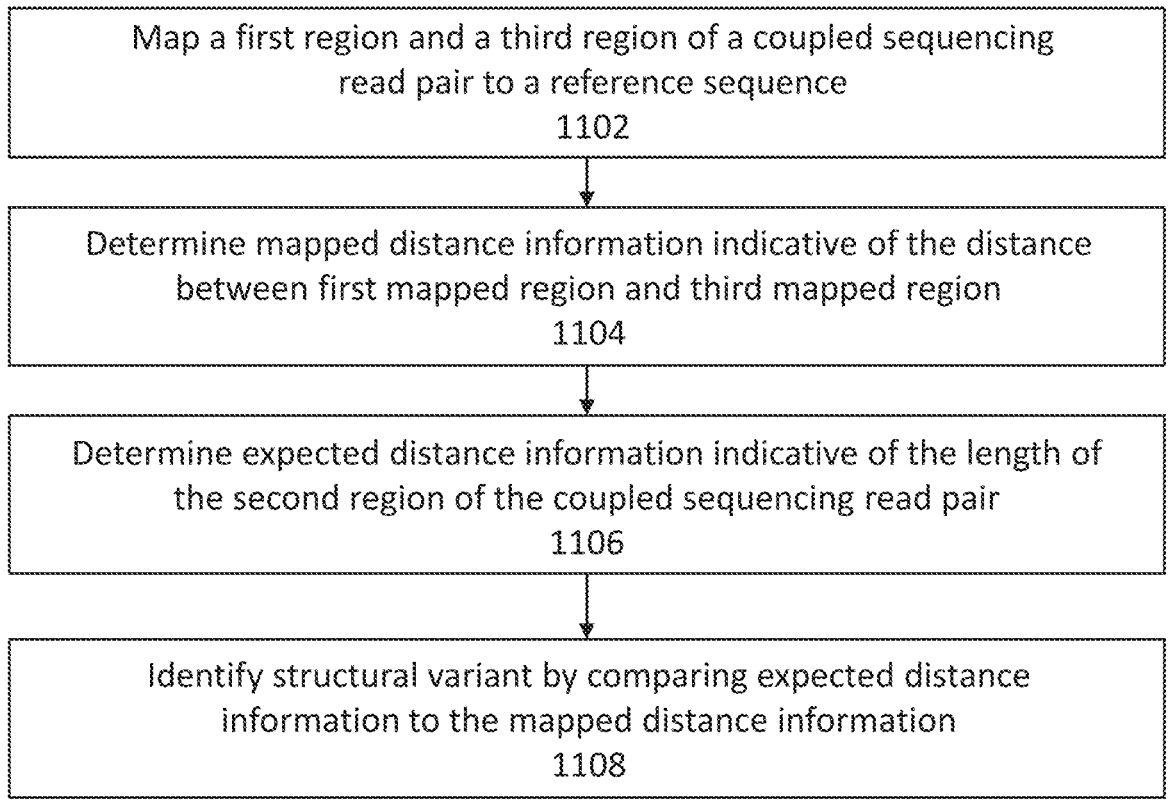
FIG. 11 illustrates an exemplary method of detecting a structural variant using a coupled sequencing read pair.

FIG. 11 illustrates an exemplary method of detecting a structural variant that includes, at step 1102, mapping a first region (or a portion thereof) and a third region (or portion thereof) of a coupled sequencing read pair to a reference sequence. A step 1104, a mapped sequence distance information is determined indicative of the distance between the first region mapped to the reference sequence and the third region mapped to the reference sequence. At step 1106, an expected distance information for the second region is determined based on the sequence region flow order and information about the sequence of the second region (for example, the sequence of the second region from the reference sequence). At step 1108, a structural variant is identified by comparing the expected distance information to the mapped distance information, wherein a difference between the mapped distance information and the expected distance information indicates the structural variant.

Figure 12:
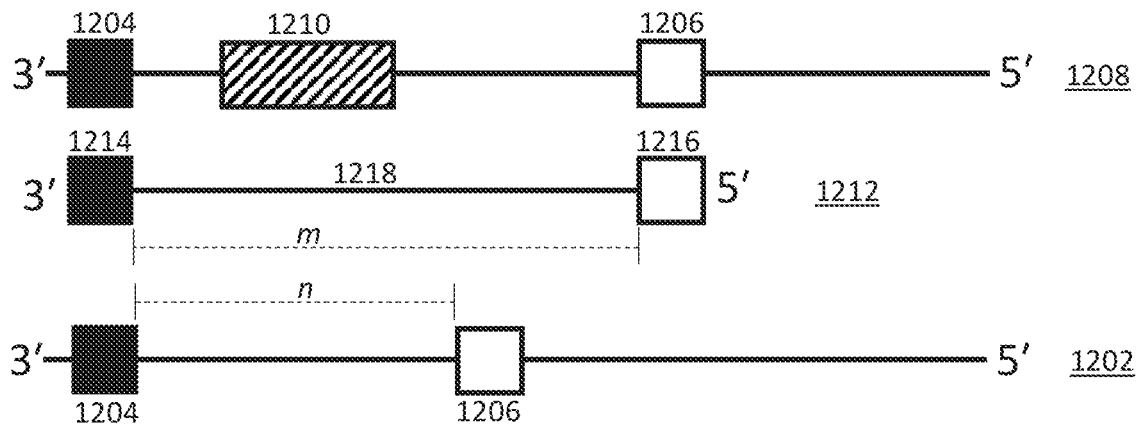
FIG. 12 illustrates a schematic demonstrating one example of how a coupled sequencing read pair can be used to detect a structural variant using distance information indicative of the length of the second region of the coupled sequencing read pair.

FIG. 12 illustrates a schematic demonstrating one example of how a coupled sequencing read pair can be used to detect a structural variant. The illustrated example shows an insertion in the subject's genome, but the methodology is similarly applied to other structural variants (e.g., deletions or chromosomal fusions). The reference sequence 1202 includes a first segment 1204 and a second segment 1206. The subject's genome 1208 also includes the first segment 1204 and the second segment 1206, but further includes an insert 1210 between the first segment 1204 and the second segment 1206. A coupled sequencing read pair 1212 generated from the subject's genome 1208 includes a first region 1214 corresponding to the first segment 1204 and a third region 1216 corresponding to the second segment 1206. A second region 1218 separates the first region 1214 and the third region 1216. The sequence of the first region 1214 and the third region 1216 can be mapped to the reference sequence 1202 at the first segment 1204 and the second segment 1206, respectively. Once mapped, the mapped distance information indicative of the distance between the first region 1214 and the third region 1216 mapped to the reference sequence 1202 (i.e., the distance between the first segment 1204 and the second segment 1206 of the reference sequence 1202) is determined as a distance of n. Expected distance information for the length of the second region 1218 can also be determined as m. The structural variant can then be determined by comparing the mapped distance information n to the expected distance information m.

In another method of detecting a variant (such as a structural variant or a SNP) within the second region, expected sequencing data is compared to determined sequencing data. For example, in some embodiments, a method of detecting a variant between two sequenced regions of a coupled sequencing read pair (with the primer having been extended through the first region using nucleotides provided in a first region flow order and/or the primer having been extended through the third region using nucleotides provided in a third region flow order) includes mapping the first region (or a portion thereof) and/or the third region (or portion thereof) to a reference sequence. Expected reference sequencing data for the other region or portion thereof (i.e., if the first region or portion is mapped, the other region refers to the third region or portion thereof and if the third region or portion thereof is mapped, the other region refers to the first region or portion thereof) is then determined. The expected sequencing data can be determined, for example, using a reference sequence for the second region, the second region flow order, the reference sequence for the other region or portion thereof (i.e., the third region or portion thereof if the first region or portion thereof is the region that is mapped, and the first region or portion thereof if the third region or portion thereof is the region that is mapped), and the flow order for the other region or portion thereof. In another example, the expected sequencing data is determined using a reference sequence for the second region, the second region flow order, a flow order for the other region, and sequencing data associated with the sequence of the other region (which may be the same sequencing data generated when generating the coupled sequencing read pair, or sequencing data generated by other means). The determined expected sequencing data for the other region can be compared to generated sequencing data for the other region. A difference between the expected and generated sequencing data indicates the presence of a variant.

In some embodiments a method of detecting a variant (such as a structural variant (e.g., a chromosomal fusion, an inversion, an insertion, or a deletion) or a SNP) between two sequenced regions of a coupled sequencing read pair, wherein the primer is extended using nucleotides provided in a third region flow order, includes mapping the first region or portion thereof to a reference sequence; determining expected sequencing data for the third region or portion thereof using (1) a reference sequence for the second region, the second region flow order, the third region flow order, and a reference sequence for the third region, or (2) a reference sequence for the second region, the second region flow order, the third region flow order, and generated sequencing data associated with the sequence of the third region; and detecting the presence of a variant by comparing the expected sequencing data for the third region to the generated sequencing data associated with the sequence of the third region. In some embodiments, a method of detecting a variant (such as a structural variant (e.g., a chromosomal fusion, an inversion, an insertion, or a deletion) or a SNP) between two sequenced regions of a coupled sequencing read pair, wherein the primer is extended using nucleotides provided in a first region flow order, includes mapping the third region or portion thereof to a reference sequence; determining expected sequencing data for the first region or portion thereof using (1) a reference sequence for the second region, the second region flow order, the first region flow order, and a reference sequence for the first region, or (2) a reference sequence for the second region, the second region flow order, the first region flow order, and generated sequencing data associated with the sequence of the first region; and detecting the presence of a variant by comparing the expected sequencing data for the first region to the generated sequencing data associated with the sequence of the first region.

Figure 13:
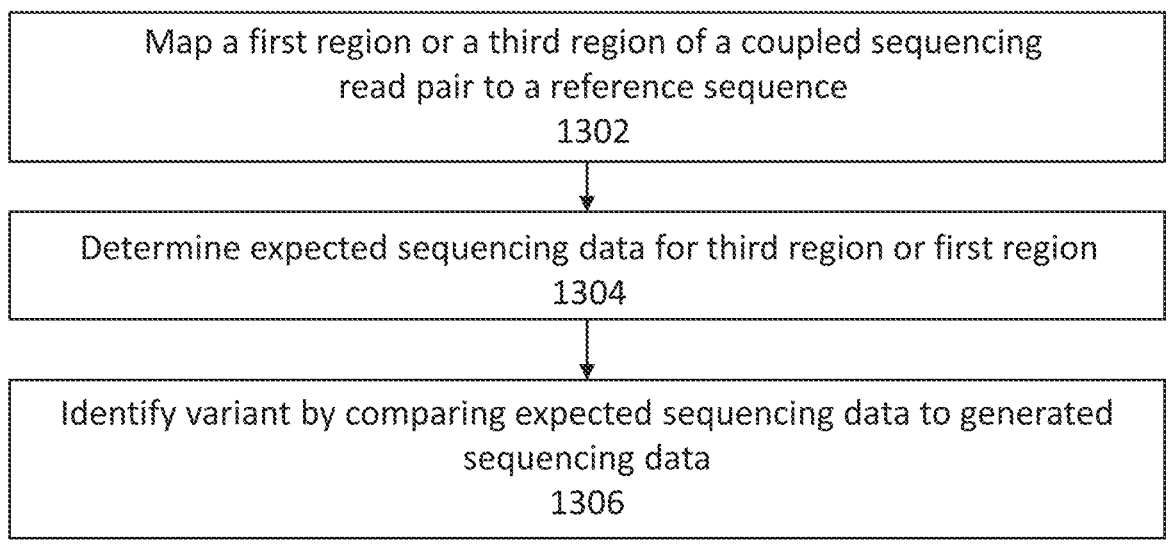
FIG. 13 illustrates an exemplary method of detecting a variant between two sequenced regions of a coupled sequencing read pair.

FIG. 13 illustrates an exemplary method of detecting a variant between two sequenced regions of a coupled sequencing read pair. At step 1302, a first region or portion thereof, or a third region or portion thereof, of a coupled sequencing read pair is mapped to a reference sequence. At step 1304, expected sequencing data for the third region or portion thereof, or the first region or portion thereof, is determined. At step 1306, the presence of a variant is detected by comparing the expected sequencing data for the first region or third region to generated sequencing data associated with the sequence of the first region or the third region. Exemplary variant detection methods are provided in the Examples.

The method of detecting a variant can use a reference sequence, which may or may not include a test variant. The test variant may be selected, for example, identifying the test variant within a second polynucleotide or from a biomarker panel. By way of example, the test variant may be used to determine a haplotype of polynucleotide. An allele or variant may be identified in a polynucleotide, and the method described herein can be used to determine whether the polynucleotide that gave rise to the coupled sequencing read pair is of the same haplotype or a different haplotype as the polynucleotide having the identified allele or variant. The detected test variant in the coupled sequencing read pair can be associated with an allele sequenced in the first region or the third region of the polynucleotide.

When detecting the presence of a test variant, the reference sequence can include a test variant, and the presence of the test variant within the subject's genome can be detected by comparing the expected test variant sequencing data for the third region or portion thereof to determined sequencing data for the third region or portion thereof. If the expected test variant sequencing data matches the determined sequencing data, then the test variant is detected within the reference sequence. For example, in some embodiments, a method of detecting a test variant between two sequenced regions of a coupled sequencing read pair (with the primer having been extended through the first region using nucleotides provided in a first region flow order and/or the primer having been extended through the third region using nucleotides provided in a third region flow order) includes mapping the first region or a portion thereof to a reference sequence that includes the test variant. Test variant expected reference sequencing data for the other region or portion thereof (i.e., if the first region or portion is mapped, the other region refers to the third region or portion thereof) is then determined. The test variant expected sequencing data can be determined, for example, using a reference sequence that includes the test variant for the second region, the second region flow order, the reference sequence for the other region or portion thereof, and the flow order for the other region or portion thereof. In another example, the expected sequencing data is determined using a reference sequence having the test variant for the second region, the second region flow order, a flow order for the other region, and sequencing data associated with the sequence of the other region (which may be the same sequencing data generated when generating the coupled sequencing read pair, or sequencing data generated by other means). The determined test variant expected sequencing data for the other region can be compared to generated sequencing data for the other region. A match between the expected and generated sequencing data indicates the presence of the test variant.

Detection of a Short Genetic Variant

The methods described herein may be used to detect a short genetic variant (e.g., a SNP or a short indel (less than 10 consecutive bases in length) within the second region (for example, when the primer is extended through the second region without detecting the presence or absence of a label of a nucleotide incorporated into the extending primer, or by including a mixture of at least two different types of nucleotide bases to extend the primer). A short genetic variant within the second region may be detected by analyzing the signal obtained when detecting the incorporation of nucleotides in a downstream (e.g., third) region. The short genetic variant can be, for example, a variant or mutation found within a subpopulation of individuals or a variant or mutation unique to a single or specific individual. The short genetic variants may be germline variants or somatic variants.

Sequencing data can be generated based on the detection of an incorporated nucleotide and the order of nucleotide introduction. Take, for example, the flowing extended sequences (i.e., each reverse complement of a corresponding template sequence): CTG, CAG, CCG, CGT, and CAT (assuming no preceding sequence or subsequent sequence subjected to the sequencing method), and a repeating flow cycle of T-A-C-G (that is, sequential addition of T, A, C, and G nucleotides in repeating cycles). A particular type of nucleotides at a given flow position would be incorporated into the primer only if a complementary base is present in the template polynucleotide). An exemplary resulting flowgram is shown in Table 5, where 1 indicates incorporation of an introduced nucleotide and 0 indicates no incorporation of an introduced nucleotide. The flowgram can be used to derive the sequence of the template strand. For example, the sequencing data (e.g., flowgram) discussed represents the sequence of the extended primer strand, and the reverse complement of which can readily be determined to represent the sequence of the template strand. An asterisk (*) in Table 5 indicates that a signal may be present in the sequencing data if additional nucleotides are incorporated in the extended sequencing strand (e.g., a longer template strand).

TABLE 5

| | Cycle 1 | | | | Cycle 2 | | | | Cycle 3 | | | |
|---|---|---|---|---|---|---|---|---|---|---|---|---|
| | Flow Position | | | | | | | | | | | |
| | 1 | 2 | 3 | 4 | 5 | 6 | 7 | 8 | 9 | 10 | 11 | 12 |
| Base in Flow | T | A | C | G | T | A | C | G | T | A | C | G |
| Extended sequence: CTG | 0 | 0 | 1 | 0 | 1 | 0 | 0 | 1 | * | * | * | * |
| Extended sequence: CAG | 0 | 0 | 1 | 0 | 0 | 1 | 0 | 1 | * | * | * | * |
| Extended sequence: CCG | 0 | 0 | 2 | 1 | * | * | * | * | * | * | * | * |
| Extended sequence: CGT | 0 | 0 | 1 | 1 | 1 | * | * | * | * | * | * | * |

TABLE 5-continued

| | Cycle 1 | | | Cycle 2 | | | Cycle 3 | | | | |
|---|---|---|---|---|---|---|---|---|---|---|---|
| | \multicolumn{12}{c}{Flow Position} |
| | 1 | 2 | 3 | 4 | 5 | 6 | 7 | 8 | 9 | 10 | 11 | 12 |
| Extended sequence: CAT | 0 | 0 | 1 | 0 | 0 | 1 | 0 | 0 | 1 | * | * | * |

The flowgram may be binary or non-binary. A binary flowgram detects the presence (1) or absence (0) of an incorporated nucleotide. A non-binary flowgram can more quantitatively determine a number of incorporated nucleotides from each stepwise introduction. For example, an extended sequence of CCG would include incorporation of two C bases in the extending primer within the same C flow (e.g., at flow position 3), and signals emitted by the labeled base would have an intensity greater than an intensity level corresponding to a single base incorporation. This is shown in Table 5. The non-binary flowgram also indicates the presence or absence of the base, and can provide additional information including the number of likely bases incorporated into each extending at the given flow position. The values do not need to be integers. In some cases, the values can be reflective of uncertainty and/or probabilities of a number of bases being incorporated at a given flow position.

In some embodiments, the sequencing data set includes flow signals representing a base count indicative of the number of bases in the sequenced nucleic acid molecule that are incorporated at each flow position. For example, as shown in Table 5, the primer extended with a CTG sequence using a T-A-C-G flow cycle order has a value of 1 at position 3, indicating a base count of 1 at that position (the 1 base being C, which is complementary to a G in the sequenced template strand). Also in Table 5, the primer extended with a CCG sequence using the T-A-C-G flow cycle order has a value of 2 at position 3, indicating a base count of 2 at that position for the extending primer during this flow position. Here, the 2 bases refer to the C-C sequence at the start of the CCG sequence in the extending primer sequence, and which is complementary to a G-G sequence in the template strand.

Figures 14A, 14B:
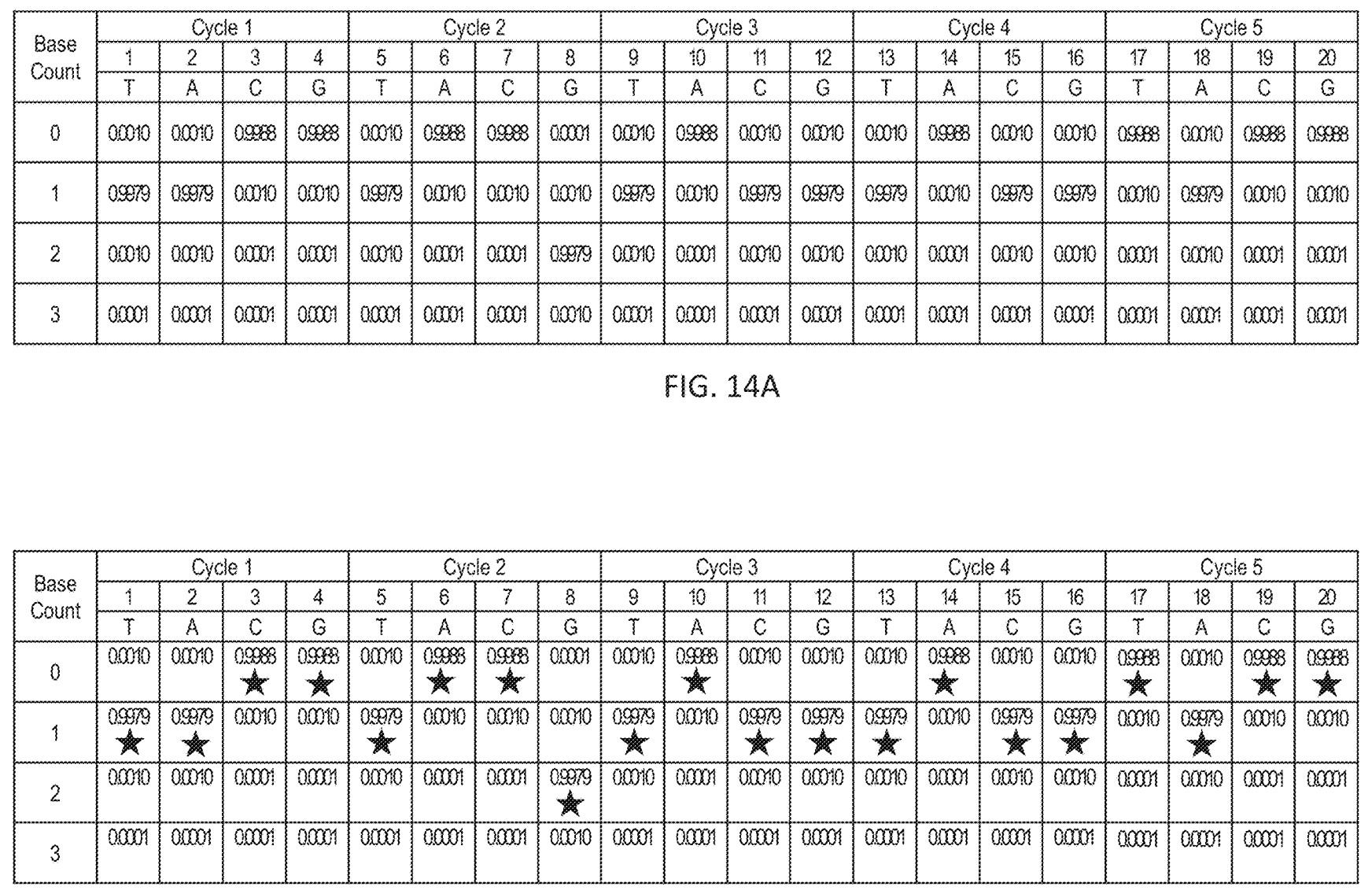

The flow signals in the sequencing data set may include one or more statistical parameters indicative of a likelihood or confidence interval for one or more base counts at each flow position. In some embodiments, the flow signal is determined from an analog signal that is detected during the sequencing process, such as a fluorescent signal of the one or more bases incorporated into the sequencing primer during sequencing. In some cases, the analog signal can be processed to generate the statistical parameter. For example, a machine-learning algorithm can be used to correct for context effects of the analog sequencing signal as described in published International patent application WO 2019084158 A1, which is incorporated by reference herein in its entirety. Although an integer number of zero or more bases are incorporated at any given flow position, a given analog signal many not perfectly match with the analog signal. Therefore, given the detected signal, a statistical parameter indicative of the likelihood of a number of bases incorporated at the flow position can be determined. Solely by way of example, for the CCG sequence in Table 5, the likelihood that the flow signal indicates 2 bases incorporated at flow position 3 may be 0.999, and the likelihood that the flow signal indicates 1 base incorporated at flow position 3 may be 0.001. The sequencing data set may be formatted as a sparse matrix, with a flow signal including a statistical parameter indicative of a likelihood for a plurality of base counts at each flow position. Solely by way of example, a primer extended with a sequence of TATGGTCGTCGA (SEQ ID NO: 15) using a repeating flow-cycle order of T-A-C-G may result in a sequencing data set shown in FIG. 14A. The statistical parameter or likelihood values may vary, for example, based on the noise or other artifacts present during detection of the analog signal during sequencing. In some embodiments, if the statistical parameter or likelihood is below a predetermined threshold, the parameter may be set to a predetermined non-zero value that is substantially zero (i.e., some very small value or negligible value) to aid the statistical analysis further discussed herein, wherein a true zero value may give rise to a computational error or insufficiently differentiate between levels of unlikelihood, e.g. very unlikely (0.0001) and inconceivable (0).

A value indicative of the likelihood of the sequencing data set for a given sequence can be determined from the sequencing data set without a sequence alignment. For example the most likely sequence, given the data, can be determined by selecting the base count with the highest likelihood at each flow position, as shown by the stars in FIG. 14B (using the same data shown in FIG. 14A). Thus, the sequence of the primer extension can be determined according to the most likely base count at each flow position: TATGGTCGTCGA (SEQ ID NO: 15). From this, the reverse complement (i.e., the template strand) can be readily determined. Further, the likelihood of this sequencing data set, given the TATGGTCGTCGA (SEQ ID NO: 15) sequence (or the reverse complement), can be determined as the product of the selected likelihood at each flow position.

The sequencing data set associated with a nucleic acid molecule can be compared to one or more (e.g., 2, 3, 4, 5, 6 or more) possible candidate sequences. A close match (based on match score, as discussed below) between the sequencing data set and a candidate sequence indicates that it is likely the sequencing data set arose from a nucleic acid molecule having the same sequence as the closely matched candidate sequence. In some embodiments, the sequence of the sequenced nucleic acid molecule may be mapped to a reference sequence (for example using a Burrows-Wheeler Alignment (BWA) algorithm or other suitable alignment algorithm) to determine a locus (or one or more loci) for the sequence. As discussed above, the sequencing data set in flowspace can be readily converted to basespace (or vice versa, if the flow order is known), and the mapping may be done in flowspace or basespace. The locus (or loci) corresponding with the mapped sequence can be associated with one or more variant sequences, which can operate as the candidate sequences (or haplotype sequences) for the analytical methods described herein. One advantage of the methods described herein is that the sequence of the sequenced nucleic acid molecule does not need to be aligned with each candidate sequence using an alignment algorithm in some cases, which is generally computationally expensive. Instead, a match score can be determined for each of the candidate sequences using the sequencing data in flowspace, a more computationally efficient operation.

Figure 14C:
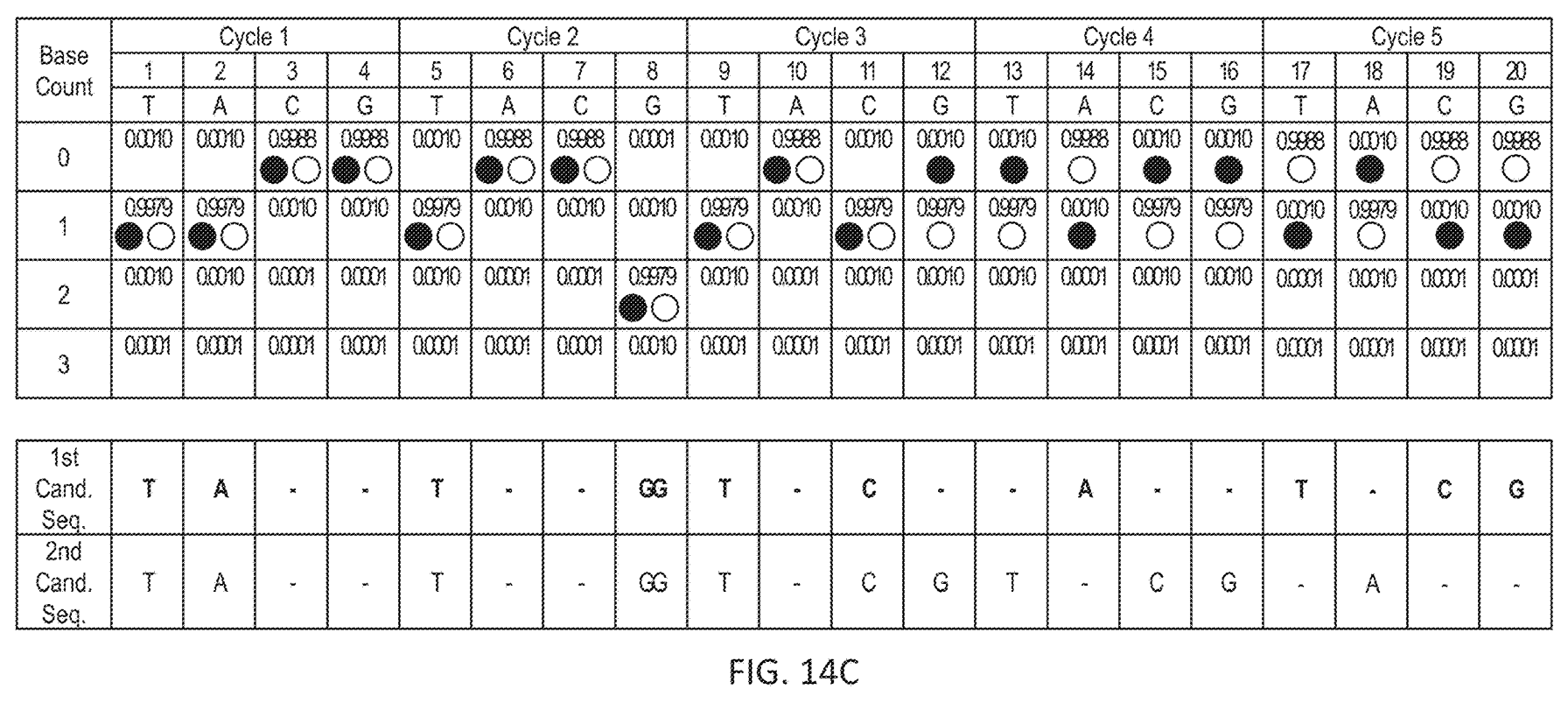

A match score indicates how well the sequencing data set supports a candidate sequence. For example, a match score indicative of a likelihood that the sequencing data set matches a candidate sequence can be determined by selecting a statistical parameter (e.g., likelihood) at each flow position that corresponds with the base count that flow position, given the expected sequencing data for the candidate sequence. The product of the selected statistical parameter can provide the match score. For example, assume the sequencing data set shown in FIG. 14A for an extended primer, and a candidate primer extension sequence of TATGGTCATCGA (SEQ ID NO: 16). FIG. 14C (showing the same sequencing data set in FIG. 14A) shows a trace for the candidate sequence (solid circles). As a comparison, the trace for the TATGGTCGTCGA (SEQ ID NO: 15) sequence (see FIG. 14B) is shown in FIG. 14C using open circles. The match score indicative of the likelihood that the sequencing data matches a first candidate sequence TATGGTCATCGA (SEQ ID NO: 16) is substantially different from the match score indicative of the likelihood that the sequencing data matches a second candidate sequence TATGGTCGTCGA (SEQ ID NO: 15), even though the sequences vary only by a single base variation. As seen in FIG. 14C, the differences between the traces is observed at flow position 12, and propagates for at least 9 flow positions (and potentially longer, if the sequencing data extended across additional flow positions). This continued propagation across one or more flow cycles may be referred to as a "flow shift" or a "cycle shift," and is generally a very unlikely event if the sequencing data set matches the candidate sequence.

A match score between each sequencing data set and candidate sequences (or each candidate sequence) can then be determined. For example, a likelihood that a sequencing data set matches a give candidate sequence $L(R_j|H_i)$ can be determined using (for example, product of) the likelihood of the selected base count at each flow position for the given candidate sequence.

The match score can be used to classify the test sequencing data and/or the nucleic acid molecule associated with the test sequencing data. The classifier can indicate that the nucleic acid molecule includes the variant (e.g., the variant included in the candidate sequence), that the nucleic acid molecule does not include the variant, or can indicate a null call. A null call neither indicates the presence or absence of the variant in the nucleic acid molecule associated with the test sequencing data, but instead indicates that the match score cannot be used to make a call with the desired statistical confidence. The test sequencing data or nucleic acid molecule may be classified as having the variant, for example, if the match score is above a desired confidence threshold. Conversely, the test sequencing data or nucleic acid molecule may be classified as not having the variant, for example, if the match score is below a desired confidence threshold.

The above analysis may be applied to select a candidate sequence from two or more different candidate sequences. The match score indicative of a likelihood that the sequencing data set matches each candidate sequence can be determined. For example, the statistical parameter at each flow position in the sequencing data set that corresponds with a base count of the candidate sequence at that flow position can be selected for each candidate sequence. In some embodiments, this analysis includes generating expected sequencing data for the candidate sequencing assuming the candidate sequence is sequenced using the same flow order used to generate the sequencing data set for the sequenced test nucleic acid molecule. This may be generated by sequencing a nucleic acid molecule with the candidate sequence, or by generating the candidate sequencing data set in silico based on the candidate sequence and the flow order. Exemplary candidate sequencing data sets are shown below the test data sequencing data set in FIG. 14C, with the first candidate sequence (TATGGTCATCGA (SEQ ID NO: 16)) corresponding to the solid circles trace and the second candidate sequence (TATGGTCGTCGA (SEQ ID NO: 15)) corresponding to the open circle trace. In some embodiments, for example, if a match score is determined for two or more different candidate sequences, the test sequencing data or the nucleic acid molecule may be classified as having the variant of one of the two or more candidate sequences, not having the variant of one of the two or more candidate sequence, or a null call may be made between the two or more candidate sequences (for example, if a call cannot be made for any of the candidate sequences or if the match score indicates two or more different variants at the same locus).

Once the match score for the sequencing data set is determined for the candidate sequences, the candidate sequence having the short genetic variant can be selected based on the match score (for example, the candidate sequence that results in a match score with the highest likelihood match from among the two or more candidate sequences). The sequencing data arising from the sequence nucleic acid molecule having the short genetic variant will match the candidate sequence having the short genetic variant, and that candidate sequence can be selected, while the rejected (or non-selected) candidate sequence(s) do not include the short genetic variant as indicated by the less likelihood match (based on the determined match scores for those candidate sequences). The non-selected candidate sequence may differ from the selected candidate sequence (which best matches the sequenced nucleic acid molecule sequencing data set) at two or more flow positions, which may be two or more consecutive flow positions or two or more non-consecutive flow positions. In some embodiments, the non-selected candidate sequence differs from the selected candidate sequence at 3 or more, 4 or more, 5 or more, 6 or more, 7 or more, 8 or more, 9 or more, or 10 or more flow positions. In some embodiments, non-selected candidate sequence differs from the selected candidate sequence across 1 or more, 2 or more, 3 or more, 4 or more, or 5 or more flow cycles. In some embodiments, the non-selected candidate sequence differs from the selected candidate sequence at X base positions, wherein the sequencing data set associated with the sequence nucleic acid molecule differs from the non-selected candidate sequence at (X+2) or more flow positions. An increase in the number of different flow positions between the selected and the non-selected candidate sequence, wherein the sequenced nucleic acid molecule sequencing data set best matches the selected candidate sequence, lowers the likelihood that the sequenced nucleic acid molecule sequencing data set resulted from sequencing a nucleic acid molecule with the non-selected candidate sequence.

The likelihood that the sequencing data set for a sequenced nucleic acid molecule matches a non-selected candidate sequence is preferably low, such as less than 0.05, less than 0.04, less than 0.03, less than 0.02, less than 0.01, less than 0.005, less than 0.001, less than 0.0005, or less than 0.0001. The likelihood that the sequencing data set for a sequenced nucleic acid molecule matches a selected candidate sequence is preferably high, such as greater than 0.95, greater than 0.96, greater than 0.97, greater than 0.98, greater than 0.99, greater than 0.995, or greater than 0.999.

Figures 15C, 15D:
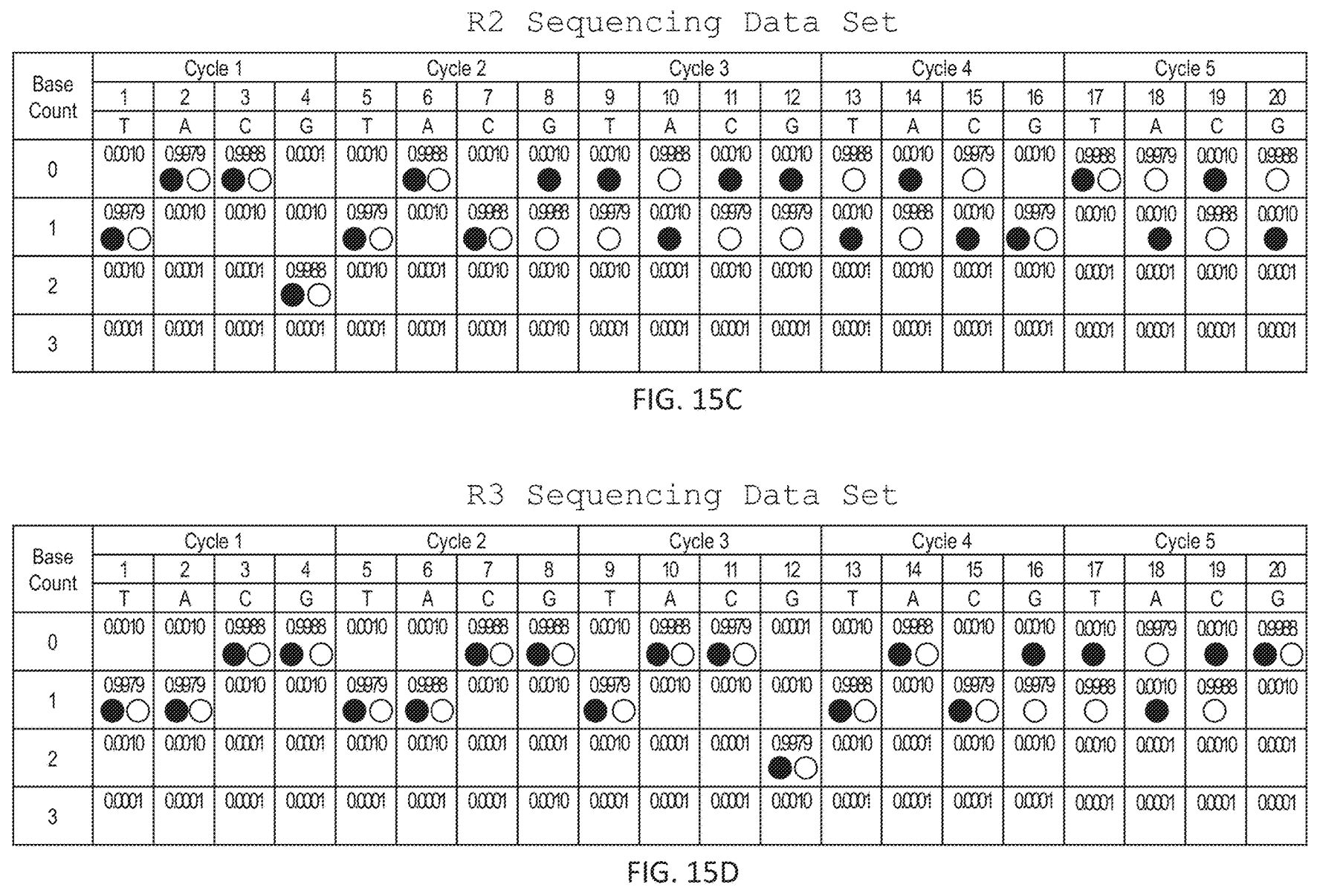

The method for detecting a short genetic variant in a test sample may, in some embodiments, include analyzing a plurality of test sequencing data sets, with each test sequencing data set being associated with a separate test nucleic acid molecule in the test sample. The nucleic acid molecules at least partially overlap at a locus, for example if the sequences of the nucleic acid molecules were aligned to a reference sequence. At least a portion of the nucleic acid molecules may have different sequencing start positions (with respect to a locus), which results in different flow positions for a given base within the sequence and/or a different flow order context. In this manner, the same candidate sequences can be used to analyze the test sequencing data sets in the plurality. For each candidate sequence, a match score indicative of a likelihood that the plurality of test sequencing data sets matches the candidate sequence can be determined, and the candidate sequence having the highest likelihood match (and thus, including the short genetic variant) can be selected. An exemplary analysis for detecting a short genetic variant using a plurality of test sequencing data sets is shown in FIGS. 15A-15D. In FIG. 15A, the sequence corresponding to three sequenced test nucleic acid molecules (R1, R2, and R3, each represented by the sequence of the extended primer) are aligned to a reference sequence at an overlapping locus associated with two candidate sequences (H1 and H2). FIG. 15B, FIG. 15C, and FIG. 15D show exemplary sequencing data sets for R1, R2, and R3, respectively, along with the selected statistical parameter at each flow position in the sequencing data set that corresponds with a base of H1 (closed circle) or H2 (open circle).

The presence (or identity) or absence of a short genetic variant can be called for the test sample using one or more determined match scores. In some embodiments, for example, a single nucleic acid molecule (or associated test sequencing data set) classified as having the variant may be sufficient to call the presence, identity, or absence of the variant, for example if the match score indicates a match with the candidate sequence with a desired or pre-set confidence. In some embodiments, an predetermined number (e.g., 1 or more, 2 or more, 3 or more, 4 or more, 5 or more, etc.) of nucleic acid molecules (or test sequencing data sets associated with nucleic acid molecules) are classified as having the variant before the variant is called for the test sample. In some embodiments, the number of nucleic acid molecules (or test sequencing data sets associated with nucleic acid molecules) is dynamically selected depending on the match scores; for example, a single nucleic acid molecule classified as having the variant with a high confidence match score may be used to call the variant, or two or more nucleic acid molecules classified as having the variant with lower confidence match scores may be used to call the variant.

Optionally, the separate match scores for sequencing data sets are collectively analyzed to determine a match score for the plurality of test sequencing data sets. For example, once the match score for each test sequencing data set for each candidate sequence is determined using the methods described herein, the match score indicative of a likelihood that the plurality of test sequencing data sets matches the candidate sequences can be determined using known Bayesian methods, for example using the HaplotypeCaller algorithm included in the Genome Analysis Toolkit (GATK), and the candidate sequence with the highest likelihood match can be selected. See, e.g., DePristo et al., *A framework for variation discovery and genotyping using next-generation DNA sequencing data*, Nature Genetics 43, 491-498 (2011); and Poplin et al., *Scaling accurate genetic variant discovery to tens of thousands of samples*, bioRxiv, www.biorxiv.org/content/10.1101/201178v3 (Jul. 24, 2018); Hwang et al., *Systematic comparison of variant calling pipelines using gold standard personal exome variants*, Scientific Reports, vol. 5, no. 17875 (2015); the contents of each of which are incorporated herein.

Hypothetical Example 1—SNP detection. A hypothetical nucleic acid molecule is sequenced using non-terminating nucleotides provided in separate nucleotide flows according to a flow-cycle order A-T-G-C, resulting in the test sequencing data set shown in FIG. 14A. Each value of in the sequencing data set indicates the likelihood that the indicated base count at each flow position is correct. Based on the sequencing data set, a preliminary sequence is determined as TATGGTCGTCGA (SEQ ID NO: 15), which is mapped to a locus of reference genome. The locus of the reference genome is associated with potential haplotype sequences TATGGTCGTCGA (SEQ ID NO: 15) (H1) and TATGGTCATCGA (SEQ ID NO: 16) (H2). A likelihood value associated with the base count of the haplotype sequence for each flow position is selected, for each haplotype. The likelihood of the sequencing data set given each haplotype is determined by multiplying the likelihood value associated with the base count of the haplotype sequence for each flow position. The log likelihood of the sequencing data set if H1 is the correct sequence is −0.015, and the log likelihood of the sequencing data set if H2 is the correct sequence is −27.008. Thus, the sequence of H1 is selected for this nucleic acid molecule.

Hypothetical Example 2—Indel detection. A hypothetical nucleic acid molecule is sequenced using non-terminating nucleotides provided in separate nucleotide flows according to a flow-cycle order A-T-G-C, resulting in the test sequencing data set shown in FIG. 16. Each value of in the sequencing data set indicates the likelihood that the indicated base count at each flow position is correct. Based on the sequencing data set (i.e., by selecting the most likely base count at each flow position), a preliminary sequence is determined as TATGGTCGATCG (SEQ ID NO: 22), which is mapped to a locus of reference genome. The locus of the reference genome is associated with potential haplotype sequences TATGGTCG-TCGA (SEQ ID NO: 21) (H1) and TATGGTCGATCG (SEQ ID NO: 22) (H2). A likelihood value associated with the base count of the haplotype sequence for each flow position is selected, for each haplotype. The likelihood of the sequencing data set given each haplotype is determined by multiplying the likelihood value associated with the base count of the haplotype sequence for each flow position. The log likelihood of the sequencing data set if H1 is the correct sequence is −24.009, and the log likelihood of the sequencing data set if H2 is the correct sequence is −0.015. Thus, the sequence of H2 is selected for this nucleic acid molecule.

When the signal difference due to a variant in the second (i.e., "dark") region propagates into the third region (i.e., a region where incorporation of nucleotides is detected), the flow shift that results from the variant in the second region can be detected in the third region. In the hypothetical examples discussed above, for example, Cycle 3 could be considered the "dark" or second region (which may be any number of cycles), and Cycle 4 and Cycle 5 could be the third region (which may also be any number of cycles).

Detection of a Transversion

A transversion is a SNP that swaps a purine for a pyrimidine or vice versa. The method described herein can be implemented to be particularly sensitive for the detection of transversions within the second region of the coupled sequencing read pair. For example, primer extension through the second region using a second region flow order comprising alternating nucleotide pairs of pyrimidines (C+T) with the purines (A+G) would be highly sensitive to transversions.

For example, a coupled sequencing read pair for detecting the presence of a base transversion in a polynucleotide can be generated by (a) hybridizing the polynucleotide to a primer to form a hybridized template; (b) generating sequencing data associated with a sequence of a first region of the polynucleotide by extending the primer using labeled nucleotides, and detecting the presence or absence of an incorporated labeled nucleotide; (c) further extending the primer extended in step (b) through a second region using a flow order comprising alternating nucleotide pairs of (1) cytosine and thymine, and (2) adenine and guanine; and (d) generating sequencing data associated with a sequence of a third region of the polynucleotide by further extending the primer extended in step (c) using labeled nucleotides, and detecting the presence or absence of an incorporated labeled nucleotide. Transversion can be detected in the second region even without detecting the presence or absence of a label of a nucleotide incorporated into the primer extended through the second region.

The coupled sequencing read pair generated for transversion detection can be used to detect the transversion by mapping a first region or portion thereof (or a third region or a portion thereof) of the coupled sequencing read pair; determining expected sequencing data for the third region or portion thereof (or the first region or portion thereof) using the second region flow order, the third region flow order, and the reference sequence; and detecting the presence of the base transversion based on the difference between expected reference sequencing data for the third region and the generated sequencing data for the third region.

The expected reference sequencing data for the third region or portion thereof (or first region or portion thereof) may be determined by, for example, using the second region flow order, the third region flow order, the reference sequence for the second region, and the reference sequence for the third region. In some embodiments, the expected reference sequencing data for the third region is determined using the second region flow order, the third region flow order, the reference sequence for the second region, and generated sequence data associated with the sequence of the third region, wherein the generated sequence data associated with the sequence of the third region is the same or different sequence data generated when generated the coupled sequencing read pair.

Variant Validation

A plurality of at least partially overlapping coupled sequencing reads can be used to validate a variant status. As sequencing errors may occasionally occur during the normal course of nucleotide incorporation into an extending primer (for example, due to polymerase error or read error), variant validation can be helpful to minimize reporting false positive or false negatives. Additionally, the sensitivity of the method described herein may vary depending on the context of the variant and flow order used when extending the primer through the second region. Therefore, to minimize false positive or false negative errors, coupled sequencing read pairs that overlap or at least partially overlap can be compared to validate the variant. The plurality of coupled sequencing read pairs that are used to validate the variant can include different start points (e.g., different first region start points, different second region start points, and/or different third region start point) or may be generated using different second region flow orders.

A test variant of interest can be selected, and a plurality of overlapping coupled sequencing read pairs are analyzed to determine the status of the test variant (e.g., whether the variant is present or absent) within the coupled sequencing read pairs. The overlapping coupled sequencing read pairs include a locus corresponding to a locus of the test variant. In some embodiments, the test variant is within the first region of at least a portion of the coupled sequencing read pairs. In some embodiments, the test variant is within the second region of at least a portion of the coupled sequencing read pairs. In some embodiments, the test variant is within the third region of at least a portion of the coupled sequencing read pairs.

A tolerance threshold can be selected to make the call as to whether the test variant is present or absent at the locus. If more couple sequencing read pairs in the plurality positively identify the test variant than a predetermined threshold identify the test variant, for example, the test variant is positively called. The threshold may be set as desired by a risk tolerance. For example, the tolerance threshold may be 60% or more, 70% or more, 80% or more, 90% or more, or 95% or more of the coupled sequencing read pairs identifying the test variant.

Figure 17:
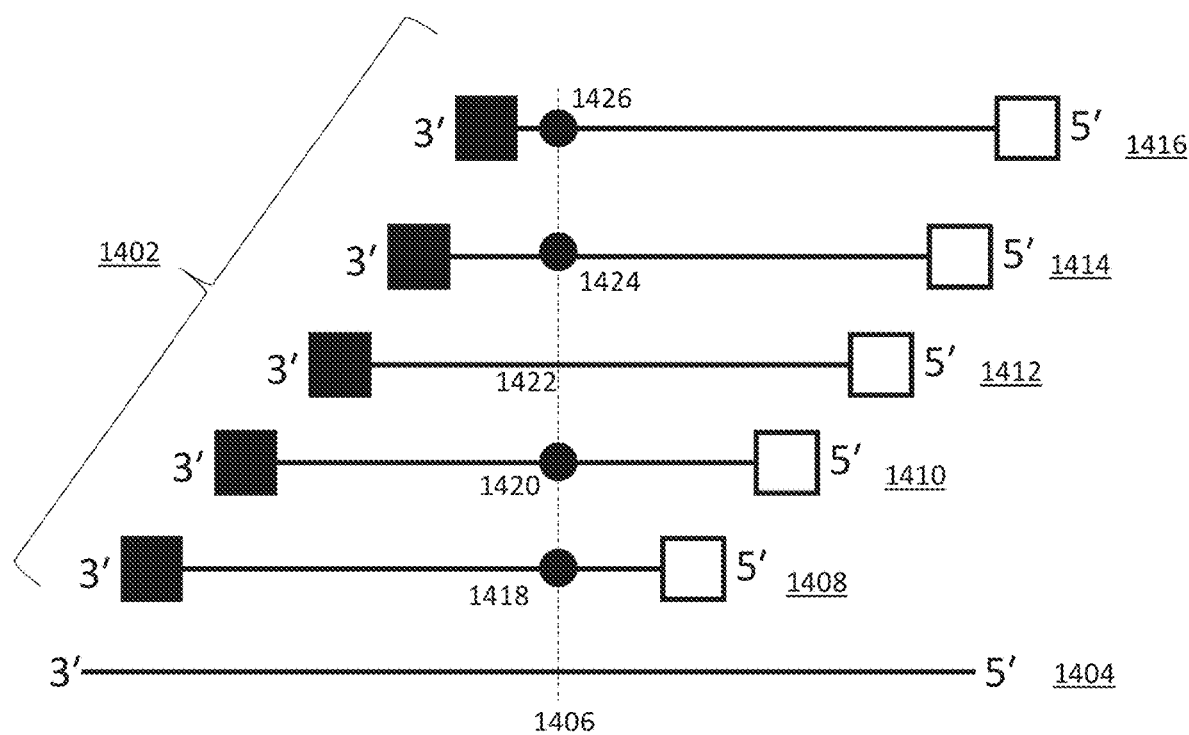
FIG. 17 illustrates an exemplary schematic for comparing coupled sequencing read pairs to determine the status of a test variant.

FIG. 17 illustrates an exemplary schematic for comparing coupled sequencing read pairs to determine the status of a test variant. A plurality of overlapping coupled sequencing read pairs 1402 are aligned to reference sequence 1404. At locus 1406, four of the five overlapping coupled sequencing read pairs allowed for the identification of the variant, which was not identified in one of the coupled sequencing read pairs. Specifically, coupled sequencing read pairs 1408, 1410, 1414, and 1416 include the identified variant at loci 1418, 1420, 1424, and 1426, respectively. The locus of the variant at each coupled sequencing read pair aligns with the reference sequence 1404 at locus 1406. Coupled sequencing read pair 1412 did not identify the variant at locus 1422 (for example, due to a sequencing read error or because of the context of the variant with the second region and the flow order used to generate coupled sequencing read pair 1412.

Construction or Validation of a Consensus Sequence

Coupled sequencing read pairs generated according to the methods described herein may be used to generate one or more consensus sequences by assembling the couple sequencing read pairs. Paired-end sequencing has been previously used to assemble a consensus sequence, but the limited information available for the region between the sequenced ends of the polynucleotides results in a lower quality consensus sequence with frequent mis-aligned sequences. See, for example, and Zerbino et al., *Velvet: Algorithms for de novo short read assembly using de Bruinn graphs*, Genome Research, vol. 18, pp. 821-820 (2008), incorporated herein by reference for all purposes. The methods described herein allow for substantially more information to be extracted from the unsequenced second region between the sequenced first and third regions. This additional information allows for a more robust and accurate consensus sequence.

In one example, the one or more consensus sequences are assembled using distance information indicative of the length of the second region of the coupled sequencing read pairs. The distance information can be determined as described herein. In one example, the distance information is determined using the second region flow order (or information associated with the second region flow order) and a probability distribution of bases in the second region. The probability distribution of bases in the second region may be, for example, an assumed distribution of bases throughout the genome, or may be a more localized probability based on the mapped locus of the first region or third region. The information associated with the second region flow order, may be, for example, a number different types of nucleotide bases simultaneously used to extend the primer through the second region. By way of example, using three-base flow steps in repeating cycles to extend the primer within the second region (for example, using cycle steps of (not A)-(not C)-(not T)-(not G), with each cycle step including the three other bases) and assuming a distribution of bases in the second region approximately the same as the genome as a whole, the primer is expected to be extended by approximately 4.7 bases for each step in the cycle. Thus, the length of the second region can be approximated as 4.7 times the number of steps in the second region flow order.

In some embodiments, the distance information is derived from expected reference sequencing data for the second region. As discussed herein, the expected reference sequencing data for the second region can be determined using the reference sequence and the second region flow order. Once the first or third region of the polynucleotide is mapped to the reference sequence, the expected sequence information, including the expected sequence length is determined, which provides the length between the first region and the third region of the polynucleotide.

The coupled sequencing read pairs can be used to validate one or more consensus sequences or a portion of one or more consensus sequences. Consensus sequence assembly may result in multiple possible sequence assemblies given the available data, and it can be challenging to select which of these possible sequences is the correct consensus sequence using traditional paired-end sequencing data. Because additional information can be extracted from the second region of the coupled sequencing read pairs, consensus sequence validation is more robust using the methods described herein. To validate the consensus sequence, the first region or a portion thereof (or the third region or portion thereof) can be mapped to a selected consensus sequence. Expected sequencing data for the other region or portion thereof (i.e., the third region or portion thereof if the first region or portion thereof is mapped, or the first region or portion thereof if the third region or portion thereof is mapped). The expected sequencing data may be determined, for example, as described herein. In one example, the expected sequencing data is determined using the second region flow order, the selected consensus sequence, and the first region flow order (if the expected sequencing data is for the first region or portion thereof) or the third region flow order (if the expected sequencing data is for the third region or portion thereof). The expected sequencing data can then be compared to the generated sequencing data for the coupled sequencing read pair at the corresponding region to validate the consensus sequence portion. Expected sequencing data matching the generated sequencing data indicates that the consensus sequence portion is correctly assembled. Expected sequencing data not matching the generated sequencing data indicates that the consensus sequence portion is incorrectly assembled.

In some embodiments, more than one consensus sequence is constructed or validated. For example, certain organisms are polyploidal (healthy humans, for example, are diploid organisms and have two copies of each chromosome (except the sex chromosomes in male humans). A consensus sequences can be assembled corresponding to one or more chromosome copies (e.g., a consensus sequence may be assembled for each chromosome pair in a human sequence). The process of assigning a coupled sequencing read pair to the corresponding chromosome of a polyploidal organism may be referred to as haplotyping. The methods described herein can be used to improve the accuracy or efficiency of haplotyping. For example, the test variant can be associated with a first chromosome or a second chromosome (or other additional chromosome from the poyploidal organism) using information from the second region of the coupled sequencing read pairs described herein.

Systems, Devices, and Reports

The operations described above, including those described with reference to FIGS. 1-17, are optionally implemented by components depicted in FIG. 18. It would be clear to a person of ordinary skill in the art how other processes, for example, combinations or sub-combinations of all or part of the operations described above, may be implemented based on the components depicted in FIG. 18. It would also be clear to a person having ordinary skill in the art how the methods, techniques, systems, and devices described herein may be combined with one another, in whole or in part, whether or not those methods, techniques, systems, and/or devices are implemented by and/or provided by the components depicted in FIG. 18.

Figure 18:
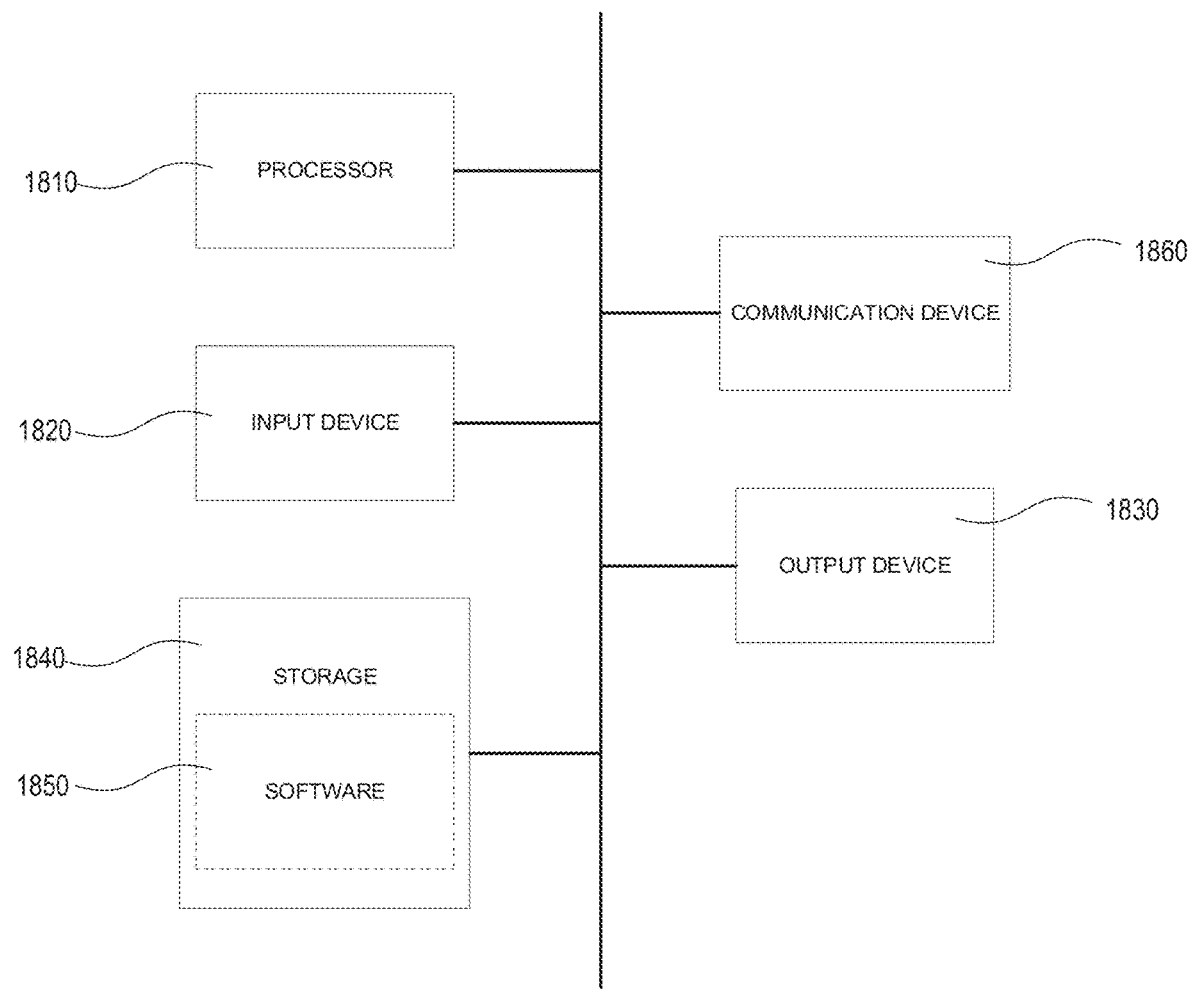
FIG. 18 illustrates an example of a computing device in accordance with one embodiment, which may be used to implement a method as described herein.

FIG. 18 illustrates an example of a computing device in accordance with one embodiment. Device 1800 can be a host computer connected to a network. Device 1800 can be a client computer or a server. As shown in FIG. 18, device 1800 can be any suitable type of microprocessor-based device, such as a personal computer, workstation, server, or handheld computing device (portable electronic device) such as a phone or tablet. The device can include, for example, one or more of processor 1810, input device 1820, output device 1830, storage 1840, and communication device 1860. Input device 1820 and output device 1830 can generally correspond to those described above, and can either be connectable or integrated with the computer.

Input device 1820 can be any suitable device that provides input, such as a touch screen, keyboard or keypad, mouse, or voice-recognition device. Output device 1830 can be any suitable device that provides output, such as a touch screen, haptics device, or speaker.

Storage 1840 can be any suitable device that provides storage, such as an electrical, magnetic or optical memory including a RAM, cache, hard drive, or removable storage disk. Communication device 1860 can include any suitable device capable of transmitting and receiving signals over a network, such as a network interface chip or device. The components of the computer can be connected in any suitable manner, such as via a physical bus or wirelessly.

Software 1850, which can be stored in storage 1840 and executed by processor 1810, can include, for example, the programming that embodies the functionality of the present disclosure (e.g., as embodied in the devices as described above).

Software 1850 can also be stored and/or transported within any non-transitory computer-readable storage medium for use by or in connection with an instruction execution system, apparatus, or device, such as those described above, that can fetch instructions associated with the software from the instruction execution system, apparatus, or device and execute the instructions. In the context of this disclosure, a computer-readable storage medium can be any medium, such as storage 1840, that can contain or store programming for use by or in connection with an instruction execution system, apparatus, or device.

Software 1850 can also be propagated within any transport medium for use by or in connection with an instruction execution system, apparatus, or device, such as those described above, that can fetch instructions associated with the software from the instruction execution system, apparatus, or device and execute the instructions. In the context of this disclosure, a transport medium can be any medium that can communicate, propagate or transport programming for use by or in connection with an instruction execution system, apparatus, or device. The transport readable medium can include, but is not limited to, an electronic, magnetic, optical, electromagnetic or infrared wired or wireless propagation medium.

Device 1800 may be connected to a network, which can be any suitable type of interconnected communication system. The network can implement any suitable communications protocol and can be secured by any suitable security protocol. The network can comprise network links of any suitable arrangement that can implement the transmission and reception of network signals, such as wireless network connections, T1 or T3 lines, cable networks, DSL, or telephone lines.

Device 1800 can implement any operating system suitable for operating on the network. Software 1850 can be written in any suitable programming language, such as C, C++, Java or Python. In various embodiments, application software embodying the functionality of the present disclosure can be deployed in different configurations, such as in a client/server arrangement or through a Web browser as a Web-based application or Web service, for example.

The methods described herein optionally further include reporting information determined using the analytical methods and/or generating a report containing the information determined suing the analytical methods. For example, in some embodiments, the method further includes reporting or generating a report containing related to the identification of a variant in a polynucleotide derived from a subject (e.g., within a subject's genome). Reported information or information within the report may be associated with, for example, a locus of a coupled sequencing read pair mapped to a reference sequence, a detected variant (such as a detected structural variant or detected SNP), one or more assembled consensus sequences and/or the a validation statistic for the one or more assembled consensus sequences. The report may be distributed to or the information may be reported to a recipient, for example a clinician, the subject, or a researcher.

Exemplary Embodiments

The following embodiments are exemplary and are not intended to limit the scope of the claimed invention.

Embodiment 1. A method of generating a coupled sequencing read pair from a polynucleotide, comprising:
(a) hybridizing the polynucleotide to a primer to form a hybridized template;
(b) generating sequencing data associated with a sequence of a first region of the polynucleotide by extending the primer using labeled nucleotides, and detecting the presence or absence of an incorporated labeled nucleotide;
(c) further extending the primer extended in step (b) through a second region using nucleotides provided in a second region flow order, wherein (i) the primer is extended through the second region without detecting the presence or absence of a label of a nucleotide incorporated into the extending primer, (ii) a mixture of at least two different types of nucleotide bases are used in at least one step of the second region flow order, or (iii) extension of the primer through the second region proceeds faster than the extension of the primer in step (b); and
(d) generating sequencing data associated with a sequence of a third region of the polynucleotide by further extending the primer extended in step (c) using labeled nucleotides, and detecting the presence or absence of an incorporated labeled nucleotide.

Embodiment 2. The method of embodiment 1, wherein extension of the primer through the second region proceeds faster than the extension of the primer through the first region.

Embodiment 3. The method of embodiment 1 or 2, further comprising associating the sequencing data of the first region with the sequencing data of the third region.

Embodiment 4. A method of generating a coupled sequencing read pair from a polynucleotide, comprising:
(a) hybridizing a primer to a first region of the polynucleotide to form a hybridized template;
(b) extending the primer through a second region using nucleotides provided in a second region flow order, wherein (i) the primer is extended through the second region without detecting the presence or absence of a label of a nucleotide incorporated into the extending primer, or (ii) a mixture of at least two different types of nucleotide bases are used in at least one step of the second region flow order; and
(c) generating sequencing data associated with a sequence of a third region of the polynucleotide by further extending the primer extended in step (b) using labeled nucleotides, and detecting the presence or absence of an incorporated labeled nucleotide.

Embodiment 5. The method of embodiment 4, wherein the first region comprises a naturally occurring sequence targeted by the primer.

Embodiment 6. The method of any one of embodiments 1-5, wherein the primer is extended through the second region without detecting the presence or absence of a label of a nucleotide incorporated into the extending primer.

Embodiment 7. The method of any one of embodiments 1-6, wherein at least a portion of the nucleotides used to extend the primer through the second region are unlabeled nucleotides.

Embodiment 8. The method of any one of embodiments 1-6, wherein the nucleotides used to extend the primer through the second region are unlabeled nucleotides.

Embodiment 9. The method of any one of embodiments 1-8, wherein a mixture of at least two different types of nucleotide bases are used in at least one step of the second region flow order.

Embodiment 10. The method of any one of embodiments 1-9, wherein the second region flow order comprises five or more nucleotide flows.

Embodiment 11. The method of embodiment 10, wherein each of the nucleotide flows comprises a single nucleotide base.

Embodiment 12. The method of embodiment 10 or 11, wherein the second region flow order induces a signal change at more than two flow positions for 50% or more of possible SNP permutations at 5% or more of random sequencing start positions.

Embodiment 13. The method of any one of embodiments 10-12, wherein the second region flow order has an efficiency of 0.6 or more base incorporations per flow.

Embodiment 14. The method of anyone of embodiments 1-13, further comprising determining expected sequencing data for the second region using a reference sequence and the second region flow order.

Embodiment 15. The method of any one of embodiments 1-14, wherein the primer is extended through the third region using nucleotides provided in a third region flow order, the method further comprising determining expected sequencing data for the third region using a reference sequence for the second region, the second region flow order, the third region flow order, and a reference sequence for the third region.

Embodiment 16. The method of embodiment 15, wherein the third region flow order comprises five or more nucleotide flows.

Embodiment 17. The method of embodiment 16, wherein each of the nucleotide flows comprises a single nucleotide base.

Embodiment 18. The method of embodiment 16 or 17, wherein the third region flow order induces a signal change at more than two flow positions for 50% or more of possible SNP permutations at 5% or more of random sequencing start positions.

Embodiment 19. The method of any one of embodiments 16-18, wherein the third region flow order has an efficiency of 0.6 or more base incorporations per flow.

Embodiment 20. The method of any one of embodiments 1-19, wherein the primer is extended through the third region using nucleotides provided in a third region flow order, the method further comprising determining expected sequencing data for the third region using a reference sequence for the second region, the second region flow order, the third region flow order, and sequencing data associated with the sequence of the third region, wherein the sequencing data associated with the sequence of the third region is the same or different sequencing data generated for the third region.

Embodiment 21. The method of any one of embodiments 14-20, wherein the expected reference data for the second region or the third region comprises a binary or non-binary flowgram.

Embodiment 22. The method of any one of embodiments 14-21, further comprising determining expected test variant sequencing data for the second region using the second region flow order and a second reference sequence for the second region, wherein the second reference sequence comprises the test variant.

Embodiment 23. The method of embodiment 22, wherein the primer is extended through the third region using nucleotides provided in a third region flow order, the method further comprising determining expected test variant sequencing data for the third region using the second reference sequence for the second region, the second region flow order, the third region flow order, and a reference sequence for the third region.

Embodiment 24. The method of embodiment 22, wherein the primer is extended through the third region using nucleotides provided in a third region flow order, the method further comprising determining expected test variant sequencing data for the third region using the second reference sequence for the second region, the second region flow order, the third region flow order, and sequencing data associated with the sequence of the third region, wherein the sequencing data associated with the sequence of the third region is the same or different sequencing data generated for the third region.

Embodiment 25. The method of any one of embodiments 22-24 wherein the expected reference sequencing data for the second region or the third region comprises a binary or non-binary flowgram.

Embodiment 26. A method of mapping a coupled sequencing read pair to a reference sequence, comprising:
mapping a first region or portion thereof, or a third region or portion thereof, of a coupled sequencing read pair generated according to the method of any one of embodiments 1-25, to a reference sequence; and
mapping the unmapped first region or portion thereof, or the unmapped third region or portion thereof, to the reference sequence using distance information indicative of the length of the second region.

Embodiment 27. A method of detecting a structural variant, comprising:
mapping a first region or portion thereof, or a third region or portion thereof, of a coupled sequencing read pair generated according to the method of any one of embodiments 1-25, to a reference sequence;
determining an expected locus within a reference sequence for the unmapped first region or portion thereof, or the unmapped third region or portion thereof, using distance information indicative of the length of the second region;
determining expected sequencing data for a sequence at the expected locus based on the reference sequence; and
detecting the structural variant by comparing the sequencing data of the unmapped first region or portion thereof, or the unmapped third region or portion thereof, to the expected sequencing data, wherein a difference between the sequencing data of the unmapped first region or portion thereof, or the unmapped third region or portion thereof, and the expected sequencing data indicates the structural variant.

Embodiment 28. A method of detecting a structural variant, comprising:
mapping a first region or portion thereof or a third region or portion thereof, of a coupled sequencing read pair generated according to the method of any one of embodiments 1-25, to a reference sequence, wherein the unmapped first region, or the unmapped third region, is unmappable within the reference sequence.

Embodiment 29. The method of embodiment 28, further comprising determining a locus of the structural variant within the reference sequence based on an expected distance information indicative of the length of the second region.

Embodiment 30. The method of any one of embodiments 27-29, wherein the unmapped first region or portion thereof, or the unmapped third region or portion thereof, is within an insertion relative to the reference sequence.

Embodiment 31. The method of any one of embodiments 27-29, wherein the unmapped first region or portion thereof, or the unmapped third region or portion thereof, bridges the start or end of an insertion relative to the reference sequence.

Embodiment 32. A method of detecting a structural variant, comprising:
mapping a first region or portion thereof and a third region or portion thereof, of a coupled sequencing read pair generated according to the method of any one of embodiments 1-25, to a reference sequence;
determining a mapped distance information between the mapped first region and the mapped third region; and
detecting the structural variant by comparing the mapped distance information to an expected distance information of the second region, wherein a difference between the mapped distance information and the expected distance information indicates the structural variant.

Embodiment 33. The method of any one of embodiments 27-32, wherein the structural variant is a chromosomal fusion, an inversion, an insertion, or a deletion.

Embodiment 34. The method of any one of embodiments 27-32, wherein the variant is an insertion or deletion within the second region.

Embodiment 35. The method of any one of embodiments 26-32, wherein the distance information is determined using information associated with the second region flow order and a probability distribution of bases in the second region.

Embodiment 36. The method of embodiment 35, wherein the information associated with the second region flow order is a number of different types of nucleotide bases simultaneously used to extend the primer through the second region.

Embodiment 37. The method of embodiment 35 or 36, wherein the probability distribution of bases in the second region is determined from the distribution of bases within the genome.

Embodiment 38. The method of any one of embodiments 26-35, wherein the distance information is derived from expected sequencing data for the second region determined using a reference sequence and the second region flow order.

Embodiment 39. The method of embodiment 38, wherein the expected sequencing data comprises a binary or non-binary flowgram.

Embodiment 40. A method of mapping a coupled sequencing read pair to a reference sequence, comprising:
  mapping a first region or portion thereof and a third region or portion thereof of a coupled sequencing read pair generated according to the method of any one of embodiments 1-25 to a reference sequence at two or more different position pairs comprising a first position and a second position; and
  selecting a correct position pair using first distance information indicative of the length of the second region and second distance information indicative of the distances between the first position and the second position for the two or more position pairs.

Embodiment 41. The method of embodiment 40 wherein the first distance information is determined using information associated with the second region flow order and a probability distribution of bases in the second region.

Embodiment 42. The method of embodiment 41, wherein the information associated with the second region flow order is a number different types of nucleotide bases simultaneously used to extend the primer through the second region.

Embodiment 43. The method of embodiment 41 or 42, wherein the probability distribution of bases in the second region is determined from the distribution of bases within the genome.

Embodiment 44. The method of embodiment 40 wherein the first distance information is derived from expected sequencing data for the second region determined using a reference sequence and the second region flow order.

Embodiment 45. The method of embodiment 44, wherein the expected reference sequencing data comprises a binary or non-binary flowgram.

Embodiment 46. A method of detecting a variant between two sequenced regions of a coupled sequencing read pair generated according to any one of embodiments 1-25, wherein the primer extended is extended through the third region using nucleotides provided in a third region flow order, comprising:
  mapping the first region or portion thereof to a reference sequence;
  determining expected sequencing data for the third region or portion thereof using (1) a reference sequence for the second region, the second region flow order, the third region flow order, and a reference sequence for the third region, or (2) a reference sequence for the second region, the second region flow order, the third region flow order, and generated sequencing data associated with the sequence of the third region, wherein the generated sequence data associated with the sequence of the third region is the same or different sequence data generated for the third region; and
  detecting the presence of a variant by comparing the expected sequencing data for the third region to the generated sequencing data associated with the sequence of the third region.

Embodiment 47. The method of embodiment 46, wherein the variant is a structural variant.

Embodiment 48. The method of embodiment 47, wherein the structural variant is a chromosomal fusion, an inversion, an insertion, or a deletion.

Embodiment 49. The method of embodiment 46, wherein the variant is a single nucleotide polymorphism (SNP).

Embodiment 50. The method of any one of embodiments 46-49, wherein the method is used to detect a test variant, and the reference sequence comprises the test variant.

Embodiment 51. The method of embodiment 50, wherein the test variant is selected by identifying the test variant within a second polynucleotide.

Embodiment 52. The method of embodiment 50 or 51, comprising associating the detected test variant with an allele sequenced in the first region or the third region of the polynucleotide.

Embodiment 53. A method of generating a coupled sequencing read pair for detecting the presence of a base transversion in an unsequenced region of a polynucleotide, comprising:
  (a) hybridizing the polynucleotide to a primer to form a hybridized template;
  (b) generating sequencing data associated with a sequence of a first region of the polynucleotide by extending the primer using labeled nucleotides, and detecting the presence or absence of an incorporated labeled nucleotide;
  (c) further extending the primer extended in step (b) through a second region using a flow order comprising alternating nucleotide pairs of (1) cytosine and thymine, and (2) adenine and guanine; and
  (d) generating sequencing data associated with a sequence of a third region of the polynucleotide by further extending the primer extended in step (c) using labeled nucleotides, and detecting the presence or absence of an incorporated labeled nucleotide.

Embodiment 54. A method of generating a coupled sequencing read pair from a polynucleotide, comprising:
  (a) hybridizing a primer to a first region of the polynucleotide to form a hybridized template;
  (b) extending the primer through a second region using a flow order comprising alternating nucleotide pairs of (1) cytosine and thymine, and (2) adenine and guanine; and
  (c) generating sequencing data associated with a sequence of a third region of the polynucleotide by further extending the primer extended in step (b) using labeled nucleotides, and detecting the presence or absence of an incorporated labeled nucleotide.

Embodiment 55. The method of embodiment 54, wherein the first region comprises a naturally occurring sequence targeted by the primer.

Embodiment 56. The method of embodiment 54 or 55, wherein the primer is extended through the second region without detecting the presence or absence of a label of a nucleotide incorporated into the extending primer.

Embodiment 57. A method of detecting the presence of a base transversion in an unsequenced region of a polynucleotide, comprising:

mapping a first region or portion thereof, and a third region or a portion thereof, of a coupled sequencing read pair generated according to any one of embodiments 54-56, wherein the primer is extended through the third region using nucleotides provided in a third region flow order, to a reference sequence;

determining expected sequencing data for the third region using the second region flow order, the third region flow order, and the reference sequence; and detecting the presence of the base transversion based on the difference between expected sequencing data for the third region and the generated sequencing data for the third region.

Embodiment 58. The method of embodiment 57, wherein the expected sequencing data for the third region is determined using the second region flow order, the third region flow order, the reference sequence for the second region, and the reference sequence for the third region.

Embodiment 59. The method of embodiment 57, wherein the expected sequencing data for the third region is determined using the second region flow order, the third region flow order, the reference sequence for the second region, and generated sequence data associated with the sequence of the third region, wherein the generated sequence data associated with the sequence of the third region is the same or different sequence data generated for the third region.

Embodiment 60. The method of any one of embodiments 57-59, wherein the expected sequencing data for the third region comprises a binary or non-binary flowgram.

Embodiment 61. A method of generating one or more consensus sequences, comprising assembling a plurality of coupled sequencing read pairs generated according to any one of embodiments 1-25.

Embodiment 62. The method of embodiment 61, wherein the one or more consensus sequences are assembled using distance information indicative of the length of the second region of the plurality of coupled sequencing read pairs.

Embodiment 63. The method of embodiment 61, wherein the distance information is determined using information associated with the second region flow order and a probability distribution of bases in the second region.

Embodiment 64. The method of embodiment 63, wherein the information associated with the second region flow order is a number different types of nucleotide bases simultaneously used to extend the primer through the third region.

Embodiment 65. The method of embodiment 63 or 64, wherein the probability distribution of bases in the second region is determined from the distribution of bases within the genome.

Embodiment 66. The method of embodiment 62, wherein the distance information is derived from expected reference sequencing data for the second region determined using a reference sequence and the second region flow order.

Embodiment 67. The method of embodiment 66, wherein the expected reference sequencing data comprises a binary or non-binary flowgram.

Embodiment 68. The method of any one of embodiments 61-67, further comprising validating a portion of a consensus sequence selected from the one or more consensus sequences using a selected coupled sequencing read associated with the portion of the selected consensus sequence, wherein the primer extended through the third region when generating the selected coupled sequencing read is extended using nucleotides provided in a third region flow order, the validating comprising:

determining expected sequencing data for the third region of the selected coupled sequencing read using the second region flow order, the third region flow order, and the portion of the selected consensus sequence; and validating the portion of the selected consensus sequence by comparing the expected sequencing data for the third region of the selected coupled sequencing read to the generated sequencing data of the third region.

Embodiment 69. A method of validating a status of a test variant, comprising:

comparing a status of the variant across a plurality of overlapping coupled sequencing read pairs generated according to any one of embodiments 1-25, the plurality of overlapping coupled sequencing read pairs comprising a locus corresponding to a locus of the test variant;

validating the status of the variant of based on the comparison.

Embodiment 70. The method of embodiment 69, wherein the first region or the third region of the selected coupled sequencing read overlaps with the second region of at least a portion of other coupled sequencing reads in the plurality of overlapping coupled sequencing reads.

Embodiment 71. The method of embodiment 69 or 70, wherein the variant status of the selected coupled sequencing read indicates a variant in the first region or the third region of the selected coupled sequencing read.

Embodiment 72. The method of embodiment 71, wherein the second region of the selected coupled sequencing read overlaps with the second region of at least a portion of other coupled sequencing reads in the plurality of overlapping coupled sequencing reads.

Embodiment 73. The method of embodiment 71 or 72, wherein the variant status of the selected coupled sequencing read indicates a variant in the second region of the selected coupled sequencing read.

Embodiment 74. A method for detecting a short genetic variant in a test sample, comprising:

generating a coupled sequencing read pair according to any one of embodiments 1-25;

comparing the sequencing data associated with a sequence of third region of the polynucleotide to expected sequencing data for an expected sequence of the third region of the polynucleotide; and calling the presence or absence of the short genetic variant in the second region of the polynucleotide.

Embodiment 75. The method of embodiment 74, wherein:

comparing the sequencing data associated with the sequence of the third region of the polynucleotide to an expected sequencing data for the third region of the polynucleotide comprises determining a match score indicative of a likelihood that the sequencing data generated for the third region of the polynucleotide matches the expected sequencing data for the third region of the polynucleotide; and calling the presence or absence of the short genetic variant in the second region of the polynucleotide comprises using the determined match score.

Embodiment 76. The method of embodiment 74 or 75, wherein the expected sequencing data for the third region of the polynucleotide is obtained by sequencing and expected sequence of the third region of the polynucleotide in silico.

Embodiment 77. The method of any one of embodiments 1-76, wherein the sequencing data associated with the sequence of the first region or the sequencing data associated with the sequence of the third region comprises flow signals representing a base count indicative of a number of bases incorporated at each flow position within a plurality of flow positions.

Embodiment 78. The method of embodiment 77, wherein the flow signals comprise a statistical parameter indicative of a base count likelihood for at least one base count at each flow position.

Embodiment 79. The method of embodiment 78, wherein the flow signals comprises a statistical parameter indicative of a base count likelihood for a plurality of base counts at each flow position.

Embodiment 80. The method of embodiment 75 or 76, wherein:
  the sequencing data associated with the sequence of the third region comprises flow signals representing a base count indicative of a number of bases incorporated at each flow position within a plurality of flow positions, wherein the flow signals comprise a statistical parameter indicative of a base count likelihood for a plurality of base counts; and
  the method further comprises selecting the statistical parameter at each flow position in the sequencing data that corresponds with a base count of the expected sequence at that flow position, and determining a match score indicative of the likelihood that the sequencing data set matches the expected sequence.

Embodiment 81. The method of embodiment 80, wherein the match score is a combined value of the selected statistical parameters across the flow positions in the sequencing data.

Embodiment 82. The method of any one of embodiments 1-81, wherein the flow-cycle order comprises 4 separate flows repeated in the same order.

Embodiment 83. The method of any one of embodiments 1-81, wherein the flow-cycle order comprises 5 or more separate flows.

Embodiment 84. The method of any one of embodiments 1-83, wherein generating the coupled sequencing read pair further comprises:
  further extending the primer through a fourth region using nucleotides provided in a fourth region flow order, wherein (i) the primer is extended through the fourth region without detecting the presence or absence of a label of a nucleotide incorporated into the extending primer, (ii) a mixture of at least two different types of nucleotide bases are used in at least one step of the fourth region flow order, or (iii) extension of the primer through the fourth region proceeds faster than the extension of the primer through the first region or the third region; and
  generating sequencing data associated with a sequence of a fifth region of the polynucleotide by further extending the primer extended through the fourth using labeled nucleotides, and detecting the presence or absence of an incorporated labeled nucleotide.

Embodiment 85. The method of embodiment 84, further comprising associating the sequencing data of the fifth region with the sequencing data of the first region or the sequencing data of the third region.

Embodiment 86. The method of any one of embodiments 1-85, wherein the polynucleotide is amplified using rolling circle amplification.

Embodiment 87. A method of detecting a short genetic variant in a test sample, comprising:
  (a) amplifying a polynucleotide using rolling circle amplification (RCA) to generate a RCA-amplified polynucleotide comprising at least a first copy of the polynucleotide and a second copy of the polynucleotide;
  (b) hybridizing the RCA-amplified polynucleotide to a primer to form a hybridized template;
  (c) generating sequencing data associated with a sequence of a first region of the polynucleotide within the first copy of the polynucleotide by extending the primer using labeled nucleotides, and detecting the presence or absence of an incorporated labeled nucleotide;
  (d) further extending the primer through a second region of the polynucleotide within the first copy of the polynucleotide using nucleotides provided in a second region flow order, wherein (i) the primer is extended through the second region of the polynucleotide within the first copy of the polynucleotide without detecting the presence or absence of a label of a nucleotide incorporated into the extending primer, (ii) a mixture of at least two different types of nucleotide bases are used in at least one step of the second region flow order, or (iii) extension of the primer through the second region of the polynucleotide within the first copy of the polynucleotide proceeds faster than the extension of the primer through the first region;
  (e) generating sequencing data associated with a sequence of a third region of the polynucleotide by further extending the primer using labeled nucleotides, and detecting the presence or absence of an incorporated labeled nucleotide;
  (f) comparing the sequencing data generated for the third region of the polynucleotide to expected sequencing data for an expected sequence of the third region of the polynucleotide;
  (g) calling the presence of the short genetic variant in the second region of the polynucleotide;
  (h) generating sequencing data associated with a sequence of the second region of the polynucleotide within the second copy of the polynucleotide by extending the primer using labeled nucleotides, and detecting the presence or absence of an incorporated labeled nucleotide; and
  (i) calling the identity of the short genetic variant in the second region of the polynucleotide.

Embodiment 88. The method of embodiment 87, wherein extension of the primer through the second region of the polynucleotide within the first copy of the polynucleotide proceeds faster than the extension of the primer through the first region of the polynucleotide within the first copy of the polynucleotide.

Embodiment 89. A method of detecting a short genetic variant in a test sample, comprising:
  (a) amplifying a polynucleotide using rolling circle amplification (RCA) to generate a RCA-amplified polynucleotide comprising at least a first copy of the polynucleotide and a second copy of the polynucleotide;
  (b) hybridizing a primer to a first region of the polynucleotide within the first copy of the polynucleotide to form a hybridized template;
  (c) extending the primer through a second region of the polynucleotide within the first copy of the polynucleotide using nucleotides provided in a second region flow order, wherein (i) the primer is extended through the second region of the polynucleotide within the first copy of the polynucleotide without detecting the presence or absence of a label of a nucleotide incorporated into the extending primer, or (ii) a mixture of at least two different types of nucleotide bases are used in at least one step of the second region flow order;
  (d) generating sequencing data associated with a sequence of a third region of the polynucleotide by further extending the primer using labeled nucleotides, and detecting the presence or absence of an incorporated labeled nucleotide;

(e) comparing the sequencing data generated for the third region of the polynucleotide to expected sequencing data for an expected sequence of the third region of the polynucleotide;

(f) calling the presence of the short genetic variant in the second region of the polynucleotide;

(g) generating sequencing data associated with a sequence of the second region of the polynucleotide within the second copy of the polynucleotide by extending the primer using labeled nucleotides, and detecting the presence or absence of an incorporated labeled nucleotide; and (h) calling the identity of the short genetic variant in the second region of the polynucleotide.

Embodiment 90. The method of embodiment 89, wherein the first region comprises a naturally occurring sequence targeted by the primer.

Embodiment 91. The method of any one of embodiments 87-90, wherein the sequencing data associated with the sequence of the second region of polynucleotide within the second copy of the polynucleotide is dynamically generated based on calling the presence of the short genetic variant in the second region of the polynucleotide.

Embodiment 92. The method of any one of embodiments 87-91, wherein the primer is extended through the second region of the polynucleotide within the first copy of the polynucleotide without detecting the presence or absence of a label of a nucleotide incorporated into the extending primer.

Embodiment 93. The method of any one of embodiments 87-92, wherein at least a portion of the nucleotides used to extend the primer through the second region of the polynucleotide within the first copy of the polynucleotide are unlabeled nucleotides.

Embodiment 94. The method of any one of embodiments 87-92, wherein the nucleotides used to extend the primer through the second region of the polynucleotide within the first copy of the polynucleotide are unlabeled nucleotides.

Embodiment 95. The method of any one of embodiments 87-94, wherein a mixture of at least two different types of nucleotide bases are used in at least one step of the second region flow order.

Embodiment 96. The method of any one of embodiments 87-95, wherein a mixture of three different types of nucleotide bases are used in at least one step of the second region flow order.

Embodiment 97. A method of synchronizing sequencing primers within a sequencing cluster, comprising:

(a) hybridizing primers to polynucleotide copies within a sequencing cluster;

(b) extending the primers through a first region of the polynucleotide copies using labeled nucleotides according to a first region flow cycle;

(c) extending the primers through a second region of the polynucleotide copies using one or more re-phasing flows, wherein a mixture of at least two different types of nucleotide bases are used in at least one of the one or more re-phasing flows; and (d) extending the primers through a third region of the polynucleotide copies using labeled nucleotides according to a third region flow cycle.

Embodiment 98. The method of embodiment 97, wherein a mixture of three different types of nucleotide bases are used in at least one of the one or more re-phasing flows.

Embodiment 99. The method of embodiment 97 or 98, wherein the one or more re-phasing flows comprises four or more flow steps.

Embodiment 100. The method of embodiment 99, wherein the one or more re-phasing flows comprises, in any order:

(i) a first flow comprising a mixture comprising A, C, and G nucleotides and omitting T nucleotides;

(ii) a second flow comprising a mixture comprising T, C, and G nucleotides and omitting A nucleotides;

(iii) a third flow comprising a mixture comprising T, A, and G nucleotides and omitting C nucleotides; and (iv) a fourth flow comprising a mixture comprising T, A, and C nucleotides and omitting G nucleotides.

Embodiment 101. The method of any one of embodiments 97-100, comprising generating sequencing data associated with a sequence of the first region by detecting the presence or absence of an incorporated labeled nucleotide while extending the primers through the first region.

Embodiment 102. The method of any one of embodiments 97-101, comprising generating sequencing data associated with a sequence of the third region by detecting the presence or absence of an incorporated labeled nucleotide while extending the primers through the third region.

Embodiment 103. A system, comprising:
one or more processors; and
a non-transitory storage medium comprising one or more programs executable by the one or more processors to:
receive information related to one or more coupled sequencing reads; and
perform the method of any one of embodiments 26-52 and 57-86.

Embodiment 104. The system of embodiment 103, wherein the one or more coupled sequencing reads are generated according to the method of any one of embodiments 1-25, 53-56, and 87-96.

EXAMPLES

The application may be better understood by reference to the following non-limiting examples, which is provided as exemplary embodiments of the application. The following examples are presented in order to more fully illustrate embodiments and should in no way be construed, however, as limiting the broad scope of the application. While certain embodiments of the present application have been shown and described herein, it will be obvious that such embodiments are provided by way of example only. Numerous variations, changes, and substitutions may occur to those skilled in the art without departing from the spirit and scope of the invention. It should be understood that various alternatives to the embodiments described herein may be employed in practicing the methods described herein.

Example 1

Figure 19A:
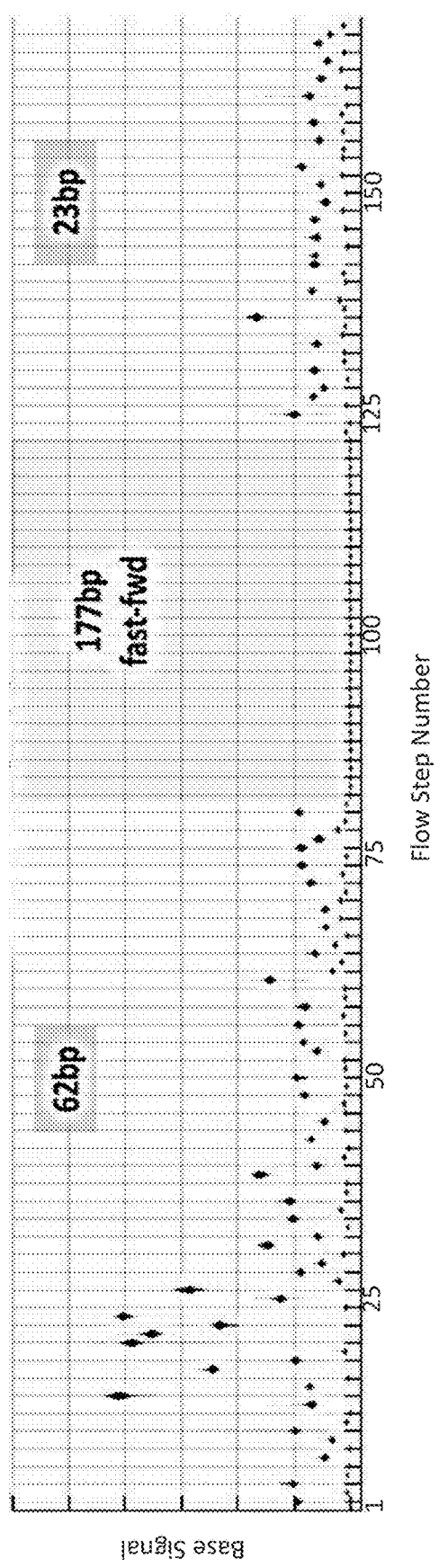
FIG. 19A show the signal coming from an incorporated base after each flow sequencing cycle in the first and third regions when extending a sequencing primer through a polynucleotide. Data was not collected within the second region because extension of the primer was accelerated through this region without detected base incorporation.

A nucleic acid construct having 262 bases was sequenced using a flow sequencing method that includes a fast-forward region, and again using a standard flow sequencing method (i.e., which does not include a fast forward region). A polynucleotide was ligated to an adapter sequence and tethered to a bead, which was amplified and associated with a sequencing surface. A sequencing primer was hybridized to a hybridization region within the adapter sequence, which allowed for the start of the flow sequencing method. In the first method, 62 bases were sequenced by extending the sequencing primer using alternating flows of a single type of fluorescently labeled, non-terminating nucleotide, and nucleotide incorporation after each step was determined using a fluorescence detector. The next 177 bases were exposed to alternating flows of un-labeled, non-terminating nucleotides where each flow has three of the four nucleotides present (i.e., "fast forward" mode) to allow the primer to be extended through the second region. Following extension of the primer through the "dark" (i.e., without detecting incorporated nucleotides) second region, another 23 bases were sequenced alternating flows of a single type of fluorescently labeled, non-terminating nucleotide, and nucleotide incorporation after each step was determined using a fluorescence detector. The results are shown in FIG. 19A, which shows the flow step number on the horizontal access and measure of sequencing signal (i.e., normalized fluorescence signal) in the vertical access. The method results in high-quality sequencing data following the fast forward regime.

Figure 19B:
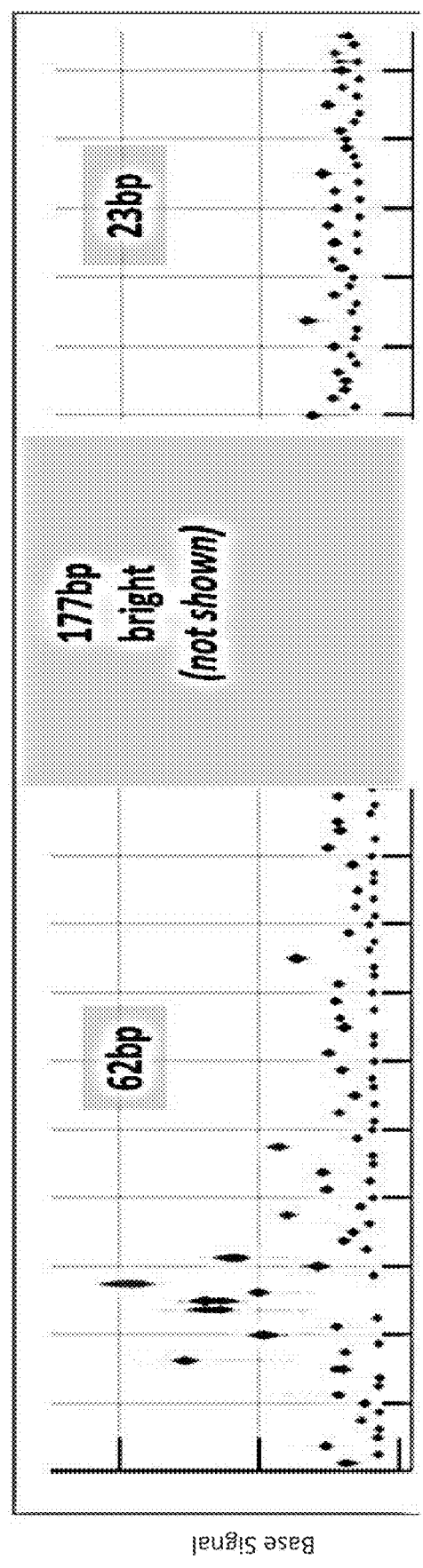
FIG. 19B show the signal coming from an incorporated base after each flow sequencing cycle in the first and third regions when extending a sequencing primer through a polynucleotide. Data was collected through the second region, but is not shown to condense the size of the figure.

The same 262 base construct was sequenced entirely in a standard flow sequencing method without an intervening fast forward regime. That is, the full 262 bases were sequenced alternating flows of a single type of fluorescently labeled, non-terminating nucleotide, and nucleotide incorporation after each step was determined using a fluorescence detector. Results are shown in FIG. 19B, which omits data from the corresponding 177 base region to compress the figure.

The sequencing construct advances more rapidly using the fast-forward flow sequencing method than the standard flow-sequencing method. The sequencing data from both ends of the polynucleotide can be associated to generate a coupled sequencing read pair and analyzed.

Example 2

Detection of a variant within SEQ ID NO: 4 (with a C4G single nucleotide polymorphism variant at base position 15 relative to reference sequence SEQ ID NO: 1) is described in this example. A coupled sequencing read pair can be generated for SEQ ID NO: 4 by hybridizing a primer to a hybridization sequence at the 5' end of SEQ ID NO: 4, and extending the primer using a flow sequencing method. In this example, 5 cycles are used, with Cycle 1 being used to extend the primer through the first region, Cycle 2 and Cycle 3 being used to extend the primer through the second region, and Cycle 4 and Cycle 5 being used to extend the primer through the third region. Cycle 1, Cycle 4, and Cycle 5 use labeled nucleotides to extend the primer, and the incorporation of a nucleotide into the primer is detected after each cycle step. In contrast, incorporation of a nucleotide into the primer may be skipped during Cycle 2 and Cycle 3. Each cycle has 4 steps, with Cycles 1, 4, and 5 include the sequential and independent addition of A-C-T-G labeled nucleotides, with a single base type being added at each cycle step, and incorporation of a labeled nucleotide being detected after each step. Cycle 2 and Cycle 3 are implemented in a "fast forward" mode, and include 4 cycle steps, wherein Step 1 omits A nucleotides (i.e., includes C, T, and G), Step 2 omits C nucleotides (i.e., includes A, T, and G), Step 3 omits T nucleotides (i.e., includes A, C, and G), and Step 4 omits G nucleotides (i.e., includes A, C, and T). Nucleotide incorporation is not detected during the fast forward mode of Cycle 2 and Cycle 3. Because Cycles 2 and 3 include multiple different nucleotide base types simultaneously during primer extension, the primer is extended faster than if only a single base type was used at any given step. The flowgrams for SEQ ID NO: 1 (the reference sequence) and SEQ ID NO: 4 (the SNP sequence) are shown in Table 6. The sequencing data indicates that the third region (Cycle 4 and Cycle 5) of SEQ ID NO: 1 is 3'-CTGAC-5', and that the third region (Cycle 4 and Cycle 5) of SEQ ID NO: 4 is 3'-CCTGC-5'. The difference between the sequencing data between SEQ ID NO: 1 and SEQ ID NO: 4 indicates the presence of a variant within the second region.

TABLE 6

| | | Cycle | | | | | | | | | | | | | |
|---|---|---|---|---|---|---|---|---|---|---|---|---|---|---|---|
| | | 1 | | | | 2 | | | | 3 | | | | 4 | 5 |
| | | | | | | | | Cycle Step | | | | | | | |
| | | 1 | 2 | 3 | 4 | 1 | 2 | 3 | 4 | 1 | 2 | 3 | 4 | 1 2 3 4 | 1 2 3 4 |
| | | | | | | | | | | Flow Bases | | | | | |
| | | A | C | T | G | C/T/G | A/T/G | A/C/G | A/C/T | A/C/G | C/T/G | A/T/G | A/C/G | A C T G | A C T G |
| | | First Region | | | | Second Region (Fast-Forward Region) | | | | | | | | Third Region | |
| SEQ ID NO: 4 | Number of Bases Incorporated | 1 | 1 | 1 | 1 | 0 | 2 | 1 | 3 | 1 | 1 | 1 | 5 | 0 0 0 2 | 1 1 0 1 |
| | Base(s) Incorporated | A | C | T | G | — | AA | C | TTA | G | A | C | TATAC- - -GG | A C - G |
| SEQ ID NO: 1 | Number of Bases Incorporated | 1 | 1 | 1 | 1 | 0 | 2 | 1 | 3 | 4 | 3 | 6 | 2 | 0 0 0 1 | 1 1 1 1 |
| | Base(s) Incorporated | A | C | T | G | — | AA | C | TTA | GGCT | ATA | CGGACG | TC | - - - G | A C T G |

SEQ ID NO: 4: 3'-TGACTTGAATCTGATATGCCTGCAGCTGAC-5'

SEQ ID NO: 1: 3'-TGACTTGAATCCGATATGCCTGCAGCTGAC-5'

TABLE 7

| | Cycle 1 | | | | Cycle 2 | | | | Cycle 3 | | | | Cycle 4 | | | | Cycle 5 | | | |
|---|---|---|---|---|---|---|---|---|---|---|---|---|---|---|---|---|---|---|---|---|
| Cycle Step | 1 | 2 | 3 | 4 | 1 | 2 | 3 | 4 | 1 | 2 | 3 | 4 | 1 | 2 | 3 | 4 | 1 | 2 | 3 | 4 |
| Flow Bases | A | C | T | G | G | C/T/G | A/T/G | A/C/T | A/C/G | C/T/G | A/T/G | A/C/G | A/C/T | A | C | T | G | A | C | T | G |
| Region | First Region | | | | Second Region (Fast-Forward Region) | | | | | | | | | Third Region | | | | | | | |
| SEQ ID NO: 8 — Number of Bases Incorporated | 1 | 1 | 1 | 1 | 0 | 2 | 1 | 3 | 4 | 3 | 6 | 2 | 0 | 0 | 0 | 1 | 0 | 0 | 1 | 0 |
| Base(s) Incorporated | A | C | T | G | — | AA | C | TTA | GGCT | ATA | CGGACG | TA | — | — | — | G | — | — | T | — |
| SEQ ID NO: 1 — Number of Bases Incorporated | 1 | 1 | 1 | 1 | 0 | 2 | 1 | 3 | 4 | 3 | 6 | 2 | 0 | 0 | 0 | 1 | 1 | 1 | 1 | 1 |
| Base(s) Incorporated | A | C | T | G | — | AA | C | TTA | GGCT | ATA | CGGACG | TC | — | — | — | G | A | C | T | G |

SEQ ID NO: 8: 3'-TGACTTGAATCCGATATGCCTGCATCAGCTGAC-5'

SEQ ID NO: 1: 3'-TGACTTGAATCCGATATGCCTGCAGCTGAC-5'

TABLE 8

| | Cycle 1 | | | | Cycle 2 | | | | Cycle 3 | | | | Cycle 4 | | | | Cycle 5 | | | |
|---|---|---|---|---|---|---|---|---|---|---|---|---|---|---|---|---|---|---|---|---|
| Cycle Step | 1 | 2 | 3 | 4 | 1 | 2 | 3 | 4 | 1 | 2 | 3 | 4 | 1 | 2 | 3 | 4 | 1 | 2 | 3 | 4 |
| Flow Bases | A | C | T | G | G | C/T/G | A/T/G | A/C/T | A/C/G | C/T/G | A/T/G | A/C/G | A/C/T | A | C | T | G | A | C | T | G |
| Region | First Region | | | | Second Region (Fast-Forward Region) | | | | | | | | | Third Region | | | | | | | |
| SEQ ID NO: 9 — Number of Bases Incorporated | 1 | 1 | 1 | 1 | 0 | 2 | 1 | 3 | 4 | 3 | 4 | 0 | 0 | 0 | 1 | 1 | 0 | 0 | 0 | 0 |
| Base(s) Incorporated | A | C | T | G | — | AA | C | TTA | GGCT | ATA | CGAC | - | — | — | T | G | — | — | — | — |
| SEQ ID NO: 1 — Number of Bases Incorporated | 1 | 1 | 1 | 1 | 0 | 2 | 1 | 3 | 4 | 3 | 6 | 2 | 0 | 0 | 0 | 1 | 1 | 1 | 1 | 1 |
| Base(s) Incorporated | A | C | T | G | — | AA | C | TTA | GGCT | ATA | CGGACG | TC | — | — | — | G | A | C | T | G |

SEQ ID NO: 9: 3'-TGACTTGAATCCGATATGCTGAC-5'

SEQ ID NO: 1: 3'-TGACTTGAATCCGATATGCCTGCAGCTGAC-5'

TABLE 9

| | Cycle 1 | | | | Cycle 2 | | | | Cycle 3 | | | | Cycle 4 | | | | Cycle 5 | | | |
|---|---|---|---|---|---|---|---|---|---|---|---|---|---|---|---|---|---|---|---|---|
| Cycle Step | 1 | 2 | 3 | 4 | 1 | 2 | 3 | 4 | 1 | 2 | 3 | 4 | 1 | 2 | 3 | 4 | 1 | 2 | 3 | 4 |
| Flow Bases | A | C | T | G | C/T/G | A/T/G | A/C/G | A/C/T | C/T/G | A/T/G | A/C/G | A/C/T | A | C | T | G | A | C | T | G |
| Region | First Region | | | | Second Region | | | | (Fast-Forward Region) | | | | Third Region | | | | | | | |
| SEQ ID NO: 12 Number of Bases Incorporated | 1 | 1 | 1 | 1 | 0 | 2 | 1 | 3 | 4 | 5 | 9 | 1 | 0 | 0 | 0 | 1 | 0 | 0 | 0 | 0 |
| Base(s) Incorporated | A | C | T | G | – | AA | C | TTA | GGCT | ATATG | CAGGCCGAC | T | – | – | – | G | – | – | – | – |
| SEQ ID NO: 1 Number of Bases Incorporated | 1 | 1 | 1 | 1 | 0 | 2 | 1 | 3 | 4 | 3 | 6 | 2 | 0 | 0 | 0 | 1 | 1 | 1 | 1 | 1 |
| Base(s) Incorporated | A | C | T | G | – | AA | C | TTA | GGCT | AEA | CGGACG | TC | – | – | – | G | A | C | T | G |

SEQ ID NO: 12: 3'-TGACTTGAATCCGATATACGTCCGGCTGAC-5'

SEQ ID NO: 1: 3'-TGACTTGAATCCGATATGCCTGCAGCTGAC-5'

Example 3

Detection of a variant within SEQ ID NO: 8 (which includes an ATC insert following base position 23 relative to the reference sequence SEQ ID NO: 1) is described in this example. A coupled sequencing read pair can be generated for SEQ ID NO: 1 and SEQ ID NO: 8 using a flow sequencing method that includes a fast forward portion through a second region. In this example, 5 cycles are used, with Cycle 1 being used to extend the primer through the first region, Cycle 2 and Cycle 3 being used to extend the primer through the second region, and Cycle 4 and Cycle 5 being used to extend the primer through the third region. Cycle 1, Cycle 4, and Cycle 5 use labeled nucleotides to extend the primer, and the incorporation of a nucleotide into the primer is detected after each cycle step. In contrast, incorporation of a nucleotide into the primer may be skipped during Cycle 2 and Cycle 3. Each cycle has 4 steps, with Cycles 1, 4, and 5 include the sequential and independent addition of A-C-T-G labeled nucleotides, with a single base type being added at each cycle step, and incorporation of a labeled nucleotide being detected after each step. Cycle 2 and Cycle 3 are implemented in a "fast forward" mode, and include 4 cycle steps, wherein Step 1 omits A nucleotides (i.e., includes C, T, and G), Step 2 omits C nucleotides (i.e., includes A, T, and G), Step 3 omits T nucleotides (i.e., includes A, C, and G), and Step 4 omits G nucleotides (i.e., includes A, C, and T). Nucleotide incorporation is not detected during the fast forward mode of Cycle 2 and Cycle 3. Because Cycles 2 and 3 include multiple different nucleotide base types simultaneously during primer extension, the primer is extended faster than if only a single base type was used at any given step. The flowgrams for SEQ ID NO: 1 (the reference sequence) and SEQ ID NO: 8 are shown in Table 7. The sequencing data indicates that the third region (Cycle 4 and Cycle 5) of SEQ ID NO: 1 is 3'-CTGAC-5', and that the third region (Cycle 4 and Cycle 5) of SEQ ID NO: 8 is 3'-AC-5'. The difference between the sequencing data between SEQ ID NO: 1 and SEQ ID NO: 8 indicates the presence of a variant within the second region.

Example 4

Detection of a variant within SEQ ID NO: 9 (which includes a deletion of the GCCTGCA bases following base position 17 relative to reference sequence SEQ ID NO: 1) is described in this example. A coupled sequencing read pair can be generated for SEQ ID NO: 1 and SEQ ID NO: 9 using a flow sequencing method that includes a fast forward portion through a second region. In this example, 5 cycles are used, with Cycle 1 being used to extend the primer through the first region, Cycle 2 and Cycle 3 being used to extend the primer through the second region, and Cycle 4 and Cycle 5 being used to extend the primer through the third region. Cycle 1, Cycle 4, and Cycle 5 use labeled nucleotides to extend the primer, and the incorporation of a nucleotide into the primer is detected after each cycle step. In contrast, incorporation of a nucleotide into the primer may be skipped during Cycle 2 and Cycle 3. Each cycle has 4 steps, with Cycles 1, 4, and 5 include the sequential and independent addition of A-C-T-G labeled nucleotides, with a single base type being added at each cycle step, and incorporation of a labeled nucleotide being detected after each step. Cycle 2 and Cycle 3 are implemented in a "fast forward" mode, and include 4 cycle steps, wherein Step 1 omits A nucleotides (i.e., includes C, T, and G), Step 2 omits C nucleotides (i.e., includes A, T, and G), Step 3 omits T nucleotides (i.e., includes A, C, and G), and Step 4 omits G nucleotides (i.e., includes A, C, and T). Nucleotide incorporation is not detected during the fast forward mode of Cycle 2 and Cycle 3. Because Cycles 2 and 3 include multiple different nucleotide base types simultaneously during primer extension, the primer is extended faster than if only a single base type was used at any given step. The flowgrams for SEQ ID NO: 1 (the reference sequence) and SEQ ID NO: 9 are shown in Table 8. The sequencing data indicates that the third region (Cycle 4 and Cycle 5) of SEQ ID NO: 1 is 3'-CTGAC-5', and that the third region (Cycle 4 and Cycle 5) of SEQ ID NO: 9 is 3'-AC-S'. The difference between the sequencing data between SEQ ID NO: 1 and SEQ ID NO: 8 indicates the presence of a variant within the second region.

Example 5

Detection of a variant within SEQ ID NO: 12 (which includes an inversion of bases GCCTGCA bases following base position 17 relative to reference sequence SEQ ID NO: 1) is described in this example. A coupled sequencing read pair can be generated for SEQ ID NO: 1 and SEQ ID NO: 12 using a flow sequencing method that includes a fast forward portion through a second region. In this example, 5 cycles are used, with Cycle 1 being used to extend the primer through the first region, Cycle 2 and Cycle 3 being used to extend the primer through the second region, and Cycle 4 and Cycle 5 being used to extend the primer through the third region. Cycle 1, Cycle 4, and Cycle 5 use labeled nucleotides to extend the primer, and the incorporation of a nucleotide into the primer is detected after each cycle step. In contrast, incorporation of a nucleotide into the primer may be skipped during Cycle 2 and Cycle 3. Each cycle has 4 steps, with Cycles 1, 4, and 5 include the sequential and independent addition of A-C-T-G labeled nucleotides, with a single base type being added at each cycle step, and incorporation of a labeled nucleotide being detected after each step. Cycle 2 and Cycle 3 are implemented in a "fast forward" mode, and include 4 cycle steps, wherein Step 1 omits A nucleotides (i.e., includes C, T, and G), Step 2 omits C nucleotides (i.e., includes A, T, and G), Step 3 omits T nucleotides (i.e., includes A, C, and G), and Step 4 omits G nucleotides (i.e., includes A, C, and T). Nucleotide incorporation is not detected during the fast forward mode of Cycle 2 and Cycle 3. Because Cycles 2 and 3 include multiple different nucleotide base types simultaneously during primer extension, the primer is extended faster than if only a single base type was used at any given step. The flowgrams for SEQ ID NO: 1 (the reference sequence) and SEQ ID NO: 12 are shown in Table 9. The sequencing data indicates that the third region (Cycle 4 and Cycle 5) of SEQ ID NO: 1 is 3'-CTGAC-5', and that the third region (Cycle 4 and Cycle 5) of SEQ ID NO: 12 is 3'-G-5'. The difference between the sequencing data between SEQ ID NO: 1 and SEQ ID NO: 12 indicates the presence of a variant within the second region.

Example 6

Figure 20C:
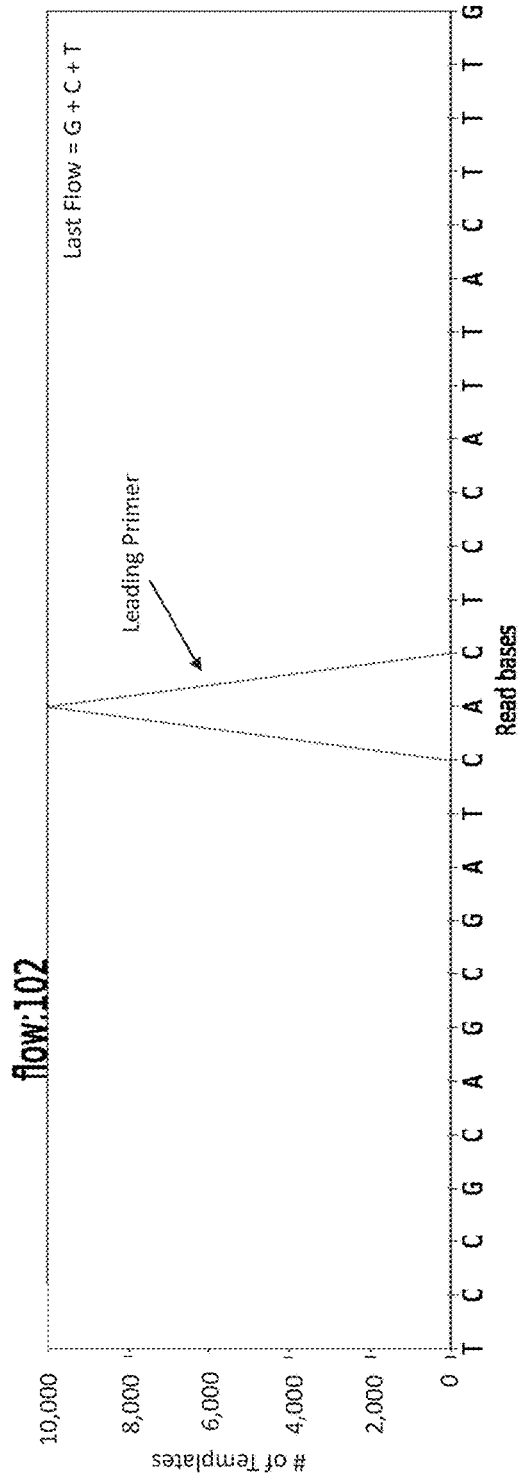
Figure 20D:
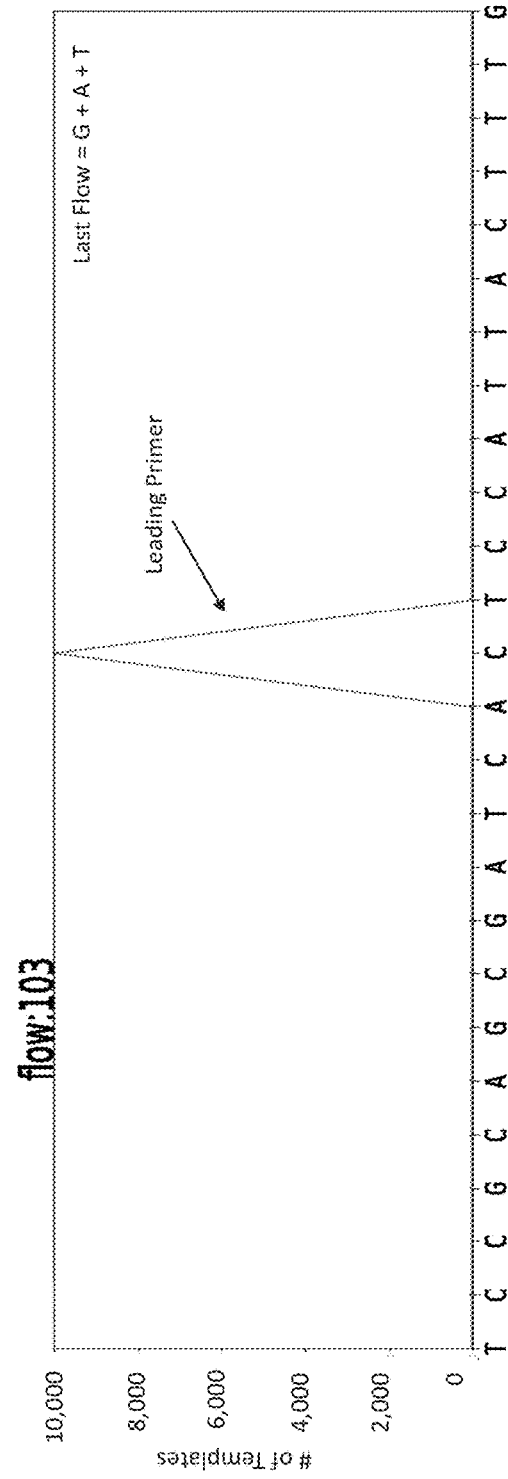
Figure 20E:
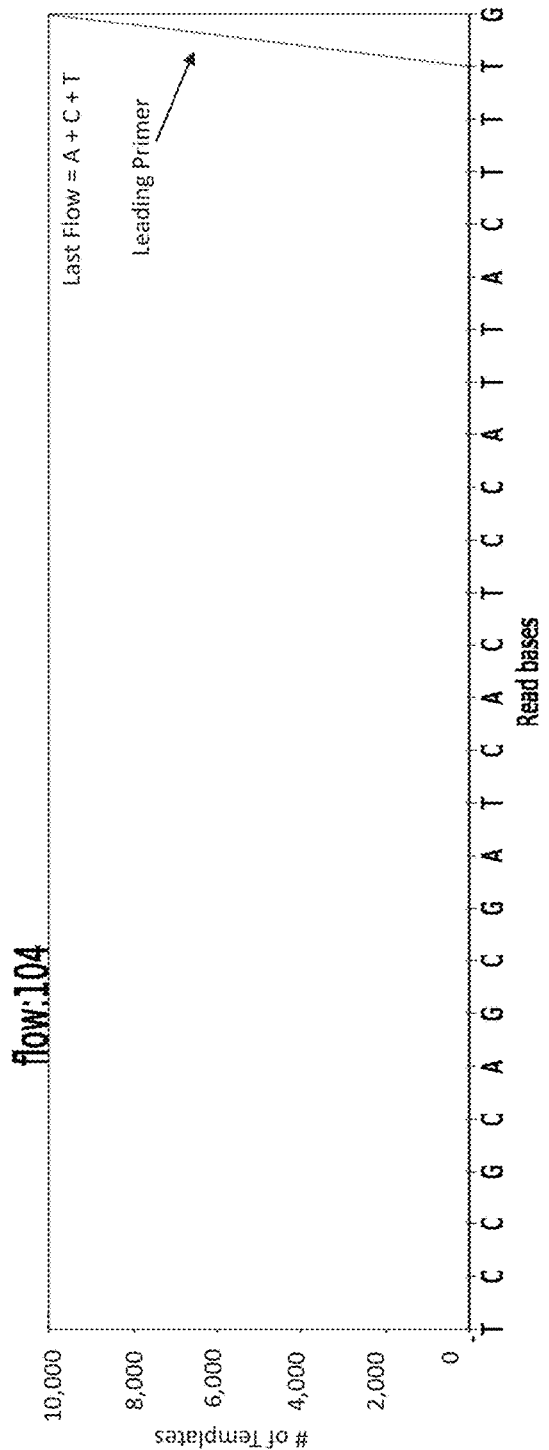
Figure 21A:
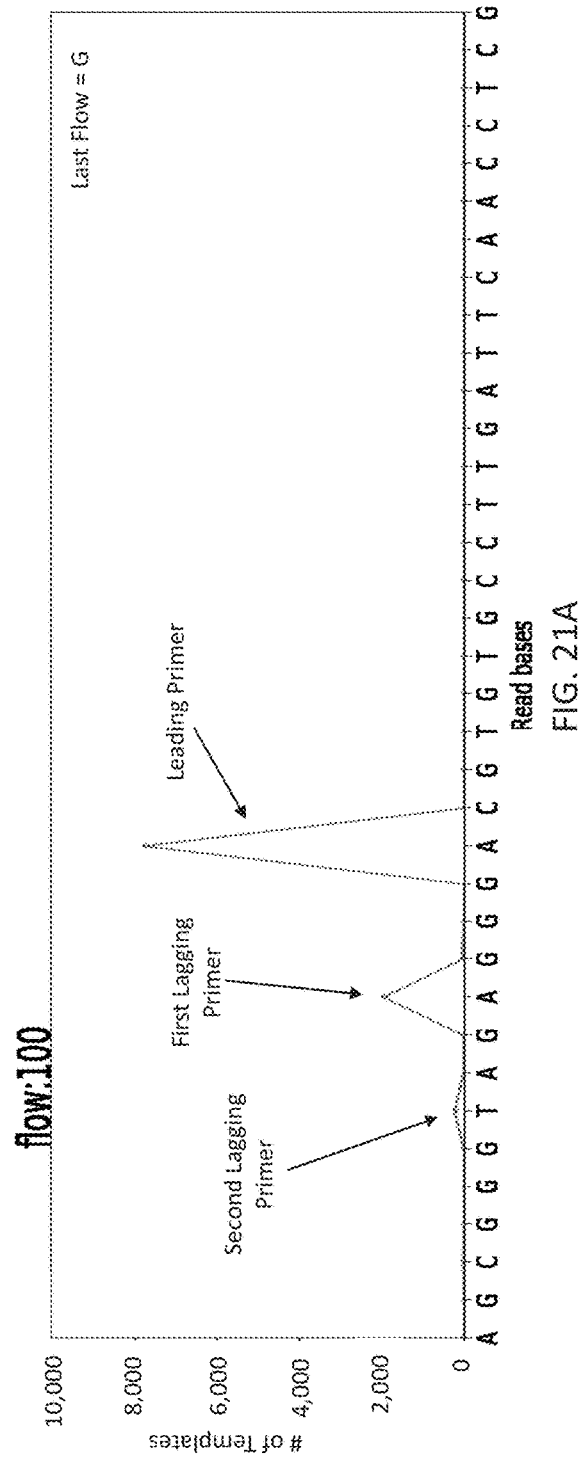
FIG. 21A-21E shows the number of primers extended against identical polynucleotide templates in another exemplary simulated sequencing protocol after 100 nucleotide flows (FIG. 21A), and re-phasing flows designed to synchronize primers within a sequencing cluster. The illustrated re-phasing flow order is a four-step order that includes nucleotide flow 101 (FIG. 21B), flow 102 (FIG. 21C), flow 103 (FIG. 21D), and flow 104 (FIG. 21E).
Figure 21B:
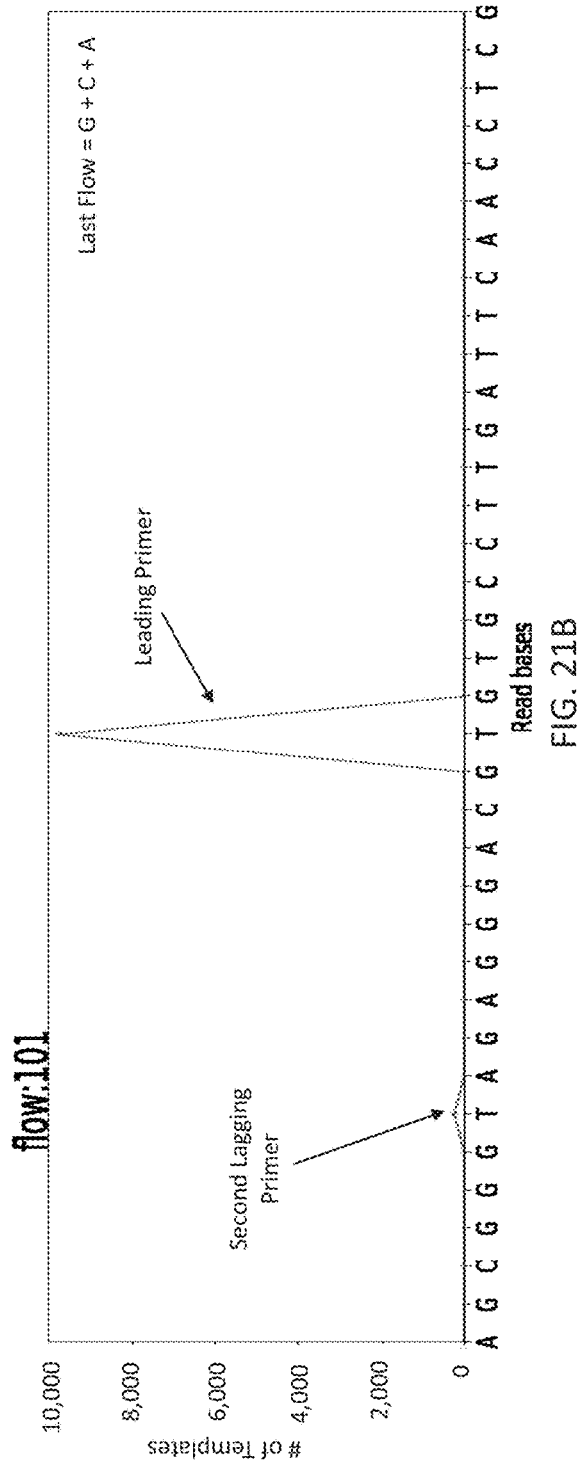
Figure 21C:
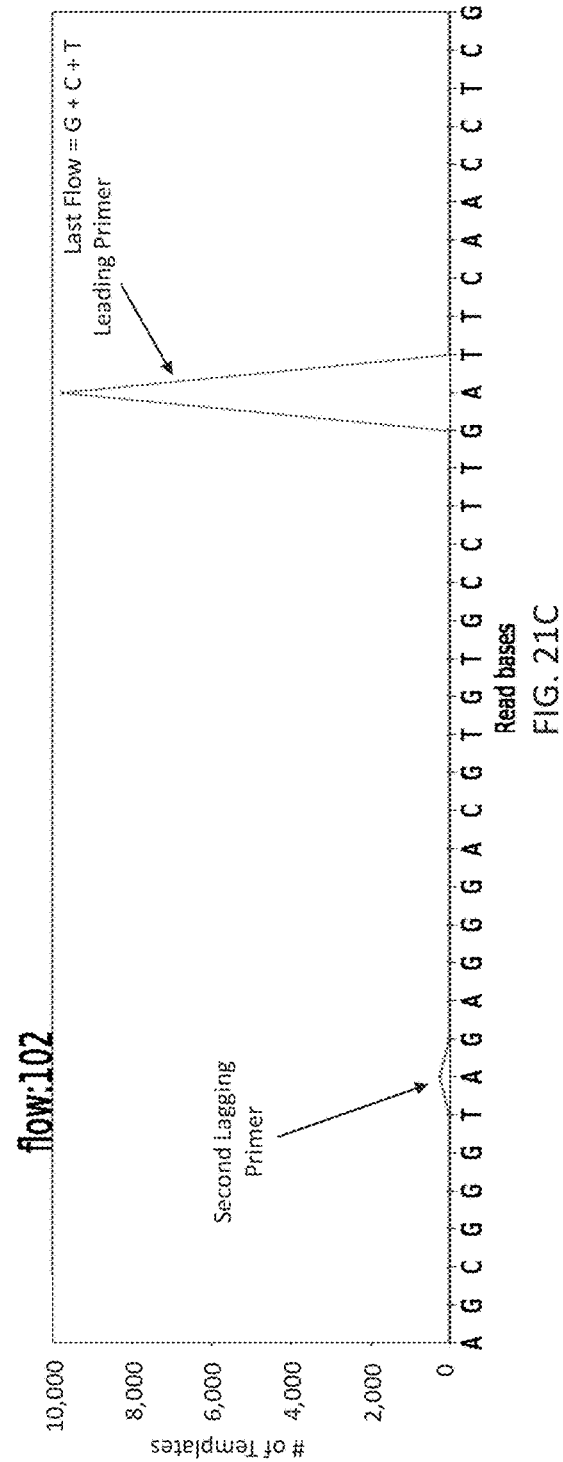
Figure 21D:
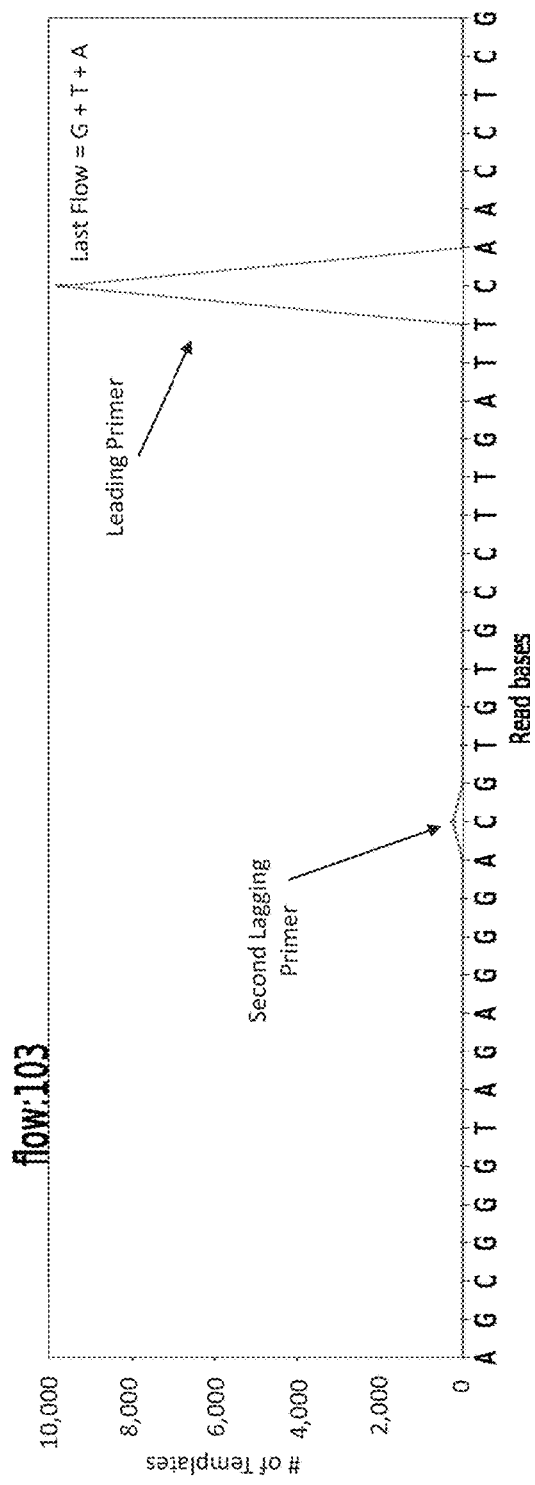
Figure 21E:
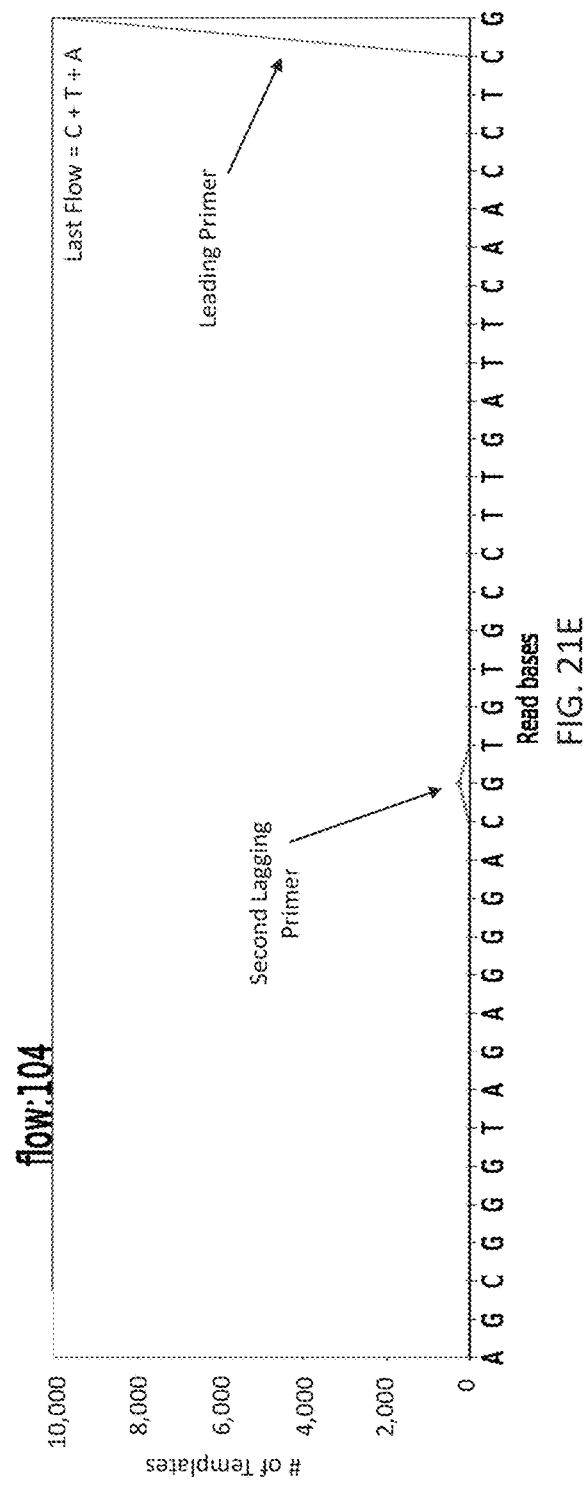
Figure 22A:
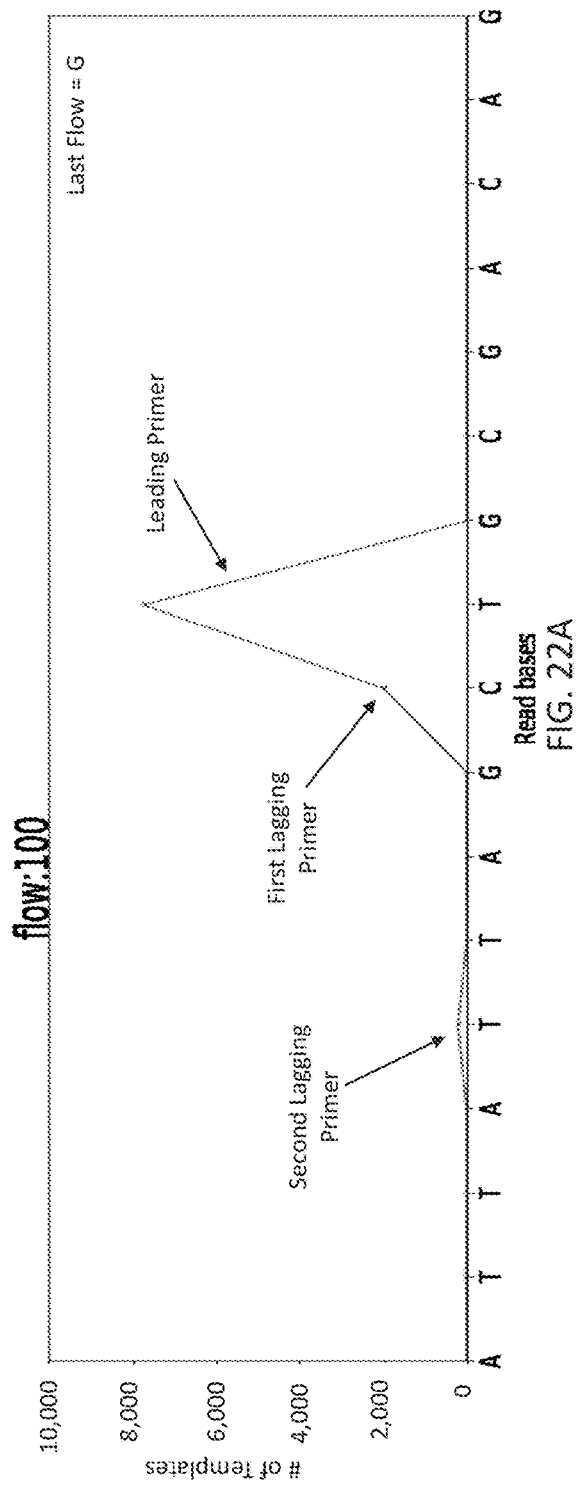
Figure 22B:
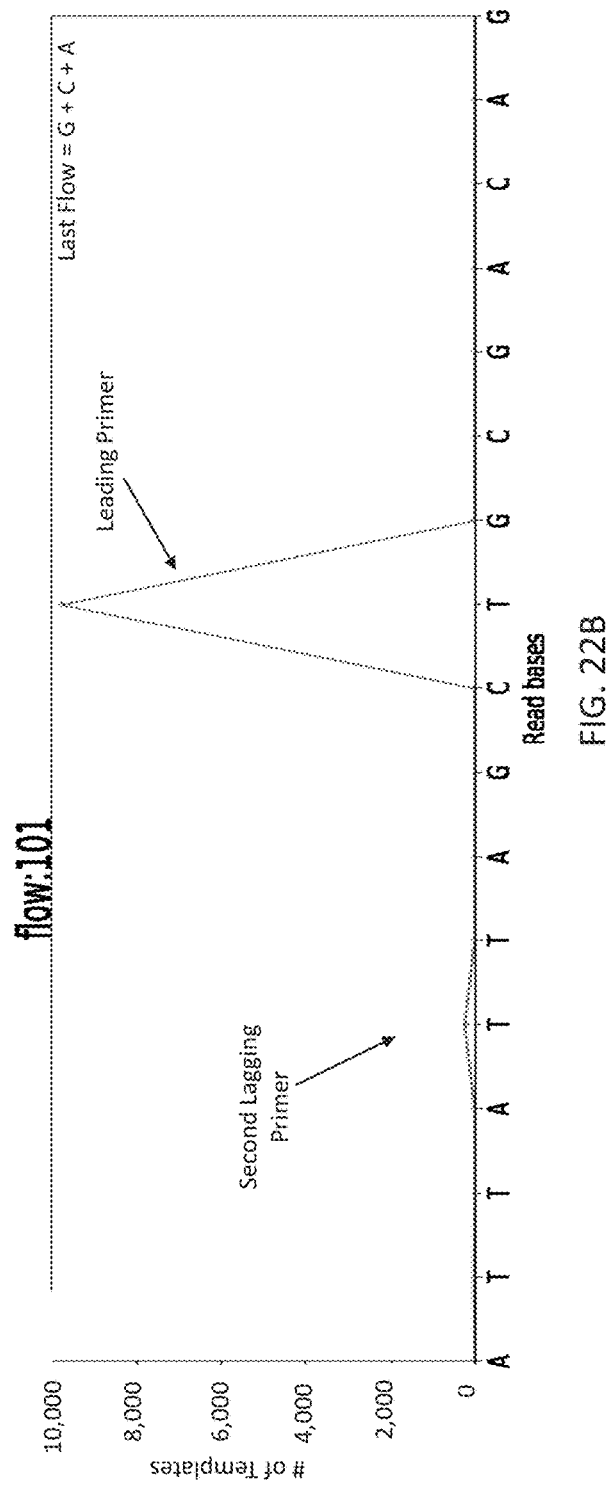
Figure 22E:
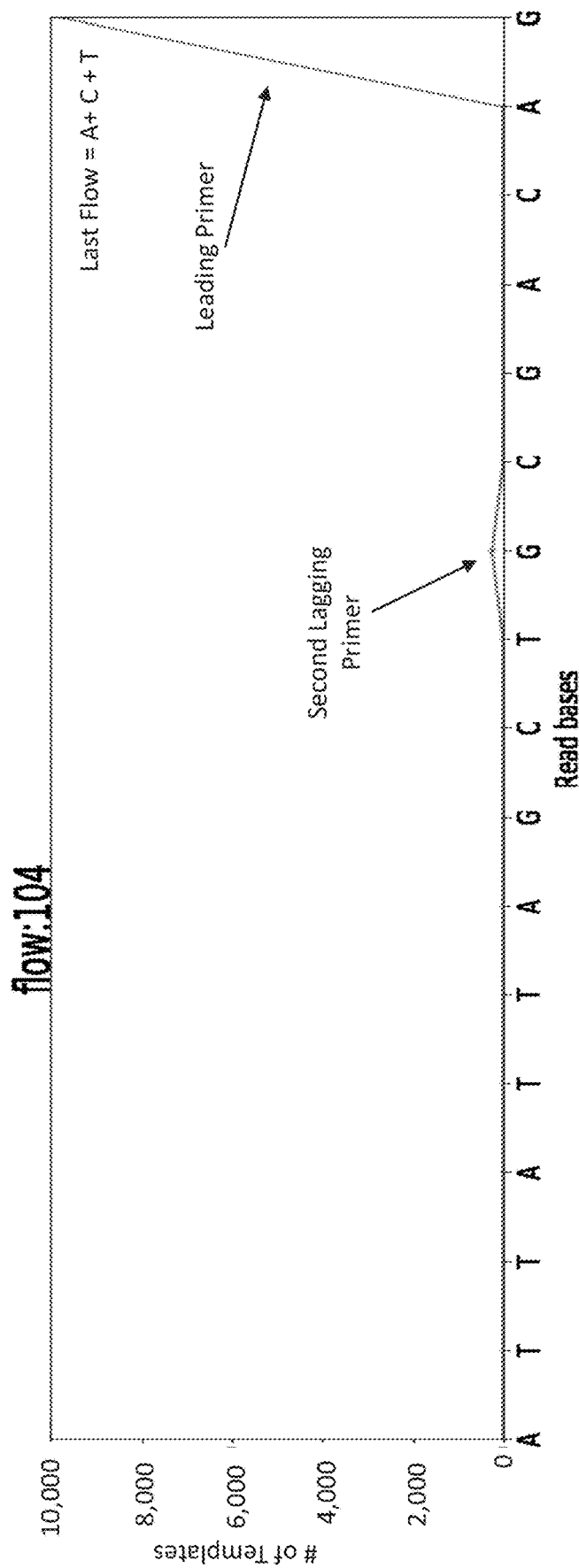

Sequencing-by-synthesis methods generally have imperfect incorporation of nucleotides into the extending primer. Over time, within a sequencing cluster, the primers can become desynchronized, resulting in degrading signal and lower confidence in making base incorporation calls. Primer desynchronization within a sequencing cluster was simulated by assuming a sequencing cluster with 10,000 identical template strands, and sequencing the template strands using non-terminating nucleotides assuming a flow order of A-C-T-G, wherein each flow has a single nucleotide. The probability of failed incorporation (i.e., a nucleotide did not incorporate into the extending primer strand when the template indicated the nucleotide should have been incorporated) was set to 0.5%. FIG. 20A shows the number of primers (strands) extended at each read base after 100 flow steps, with the 100th flow having a G non-terminating nucleotide. The sequencing cluster includes templates hybridized to a leading sequencing primer wherein the G nucleotide was incorporated into the extending primer such that the next expected incorporated nucleotide is an A, a first lagging primer wherein a G nucleotide was incorporated into the extending primer such that the next expected incorporated nucleotide is a C, and a second lagging primer no nucleotide was incorporated into the extending primer from the 100th flow. The first lagging primer and second lagging primer represent primers for which incorporation of an expected nucleotide into the extending primer failed at some point during the sequencing process. Synchronization of the extension primers using a re-phasing flow order was simulated using synchronizing flow order. At flow 101, the primer was extended using a mixture of G, C, and A non-terminating nucleotides (FIG. 20B), which extended the first and second lagging primers until synchronized with the leading primer. Because flow 101 did not include a T nucleotide, it did not extend further. The simulated synchronizing flow order continued with flow 102, which had a mixture of G, C, and T non-terminating nucleotides (FIG. 20C), flow 103, which had a mixture of G, T, and A non-terminating nucleotides (FIG. 20D), and flow 104, which had a mixture of T, A, and C non-terminating nucleotides (FIG. 20E).

The simulated synchronizing flow order was tested using additional sequences as seen in FIG. 21A-21E and FIG. 22A-22E. Other successful simulations were conducted using a synchronizing flow order and different template sequences.

Example 7

Figure 23:
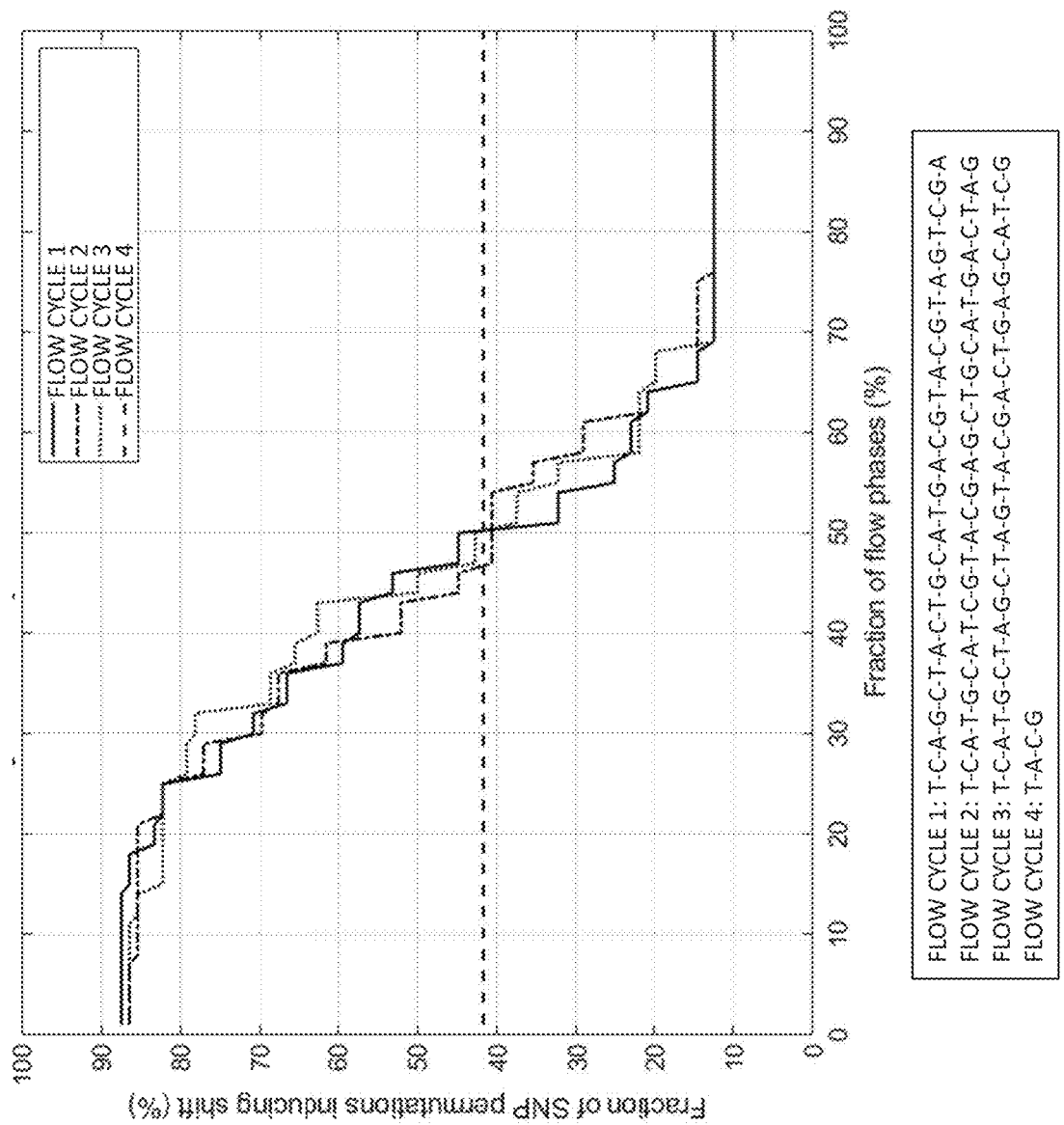
FIG. 23 shows, for four exemplary flow cycle orders (including three of which that are extended flow cycle orders), the sensitivity of detected a SNP permutation given random sequencing start positions.

More than a million extended sequencing flow orders were tested in silico for their likelihood to induce a signal change in more than two flow positions over the set of all possible SNPs (XYZ→XQZ where Q≠Y (and Q, X, Y, and Z are each any one of A, C, G, and T)). Extended flow orders were designed to have a minimum of 12 base sequences with all valid 2-base flow permutations, and flow orders having sequential base repeats were removed. All possible starting positions for the flow order were tested to assess sensitivity of the extended flow orders to induce the signal change at more than two flow positions. FIG. 23 and Table 4 show exemplary results of this analysis. In FIG. 23, the x-axis indicates the fraction of the flow phases (or fragmentation start positions), and the y-axis indicates the fraction of SNP permutations having induced a signal change at more than two flow positions. Several flow orders induce two or more signal differences at all possible (87.5%) SNP permutations for approximately 10% of reads (or flow start positions). A four base periodic flow only induces cycle shifts in only 42% of possible SNPs but it does this with all reads or flow phases. A final evaluation of efficiency was performed against a million read subset of human reference genome to establish viability. This is a practical measure of how efficiently the flow order extends the sequence given the patterns and biases in a real organism.

Example 8

Figure 24:
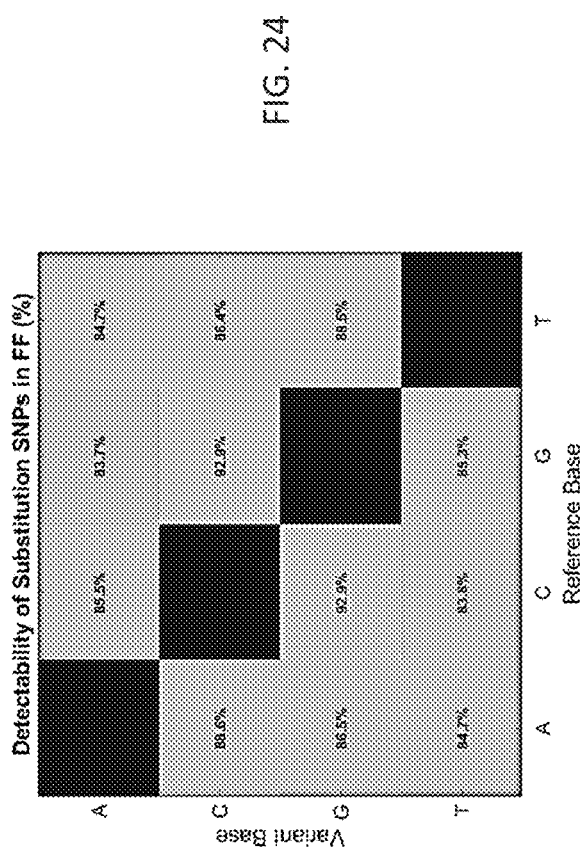
FIG. 24 shows a matrix showing the base detection sensitivity for various SNP variants detected using a simulated fast forward sequencing protocol, wherein the second regions of the synthetic polynucleotides are sequenced using a repeated four-step flow cycle, each flow having a single nucleotide base.

To test sensitivity of fast forward sequencing to detect SNPs, the sequencing method was simulated in silico to sequence Approximately 1.14 million synthetic nucleic acid molecules within the hg38 reference genome, each synthetic nucleic acid molecule being a 2 kilobase segment with a random starting point within the reference genome. 502 bp segments from each synthetic sequencing read was generated, and all three possible single base mutations queried at each base within the ~502 bp segment (i.e., a total of 500×~1.14M×3 possible variants (i.e., ABC→ADC, wherein B≠D)) were queried for SNP detection. For each SNP variant ABC→ADC, the SNP was considered non-detectable when (A=B and D=C) or (A=D and B=C), as neither SNP would generate a new zero or new non-zero signal in a flowgram. A matrix of variant base to reference base detection sensitivity is shown in FIG. 24.

Figure 25A:
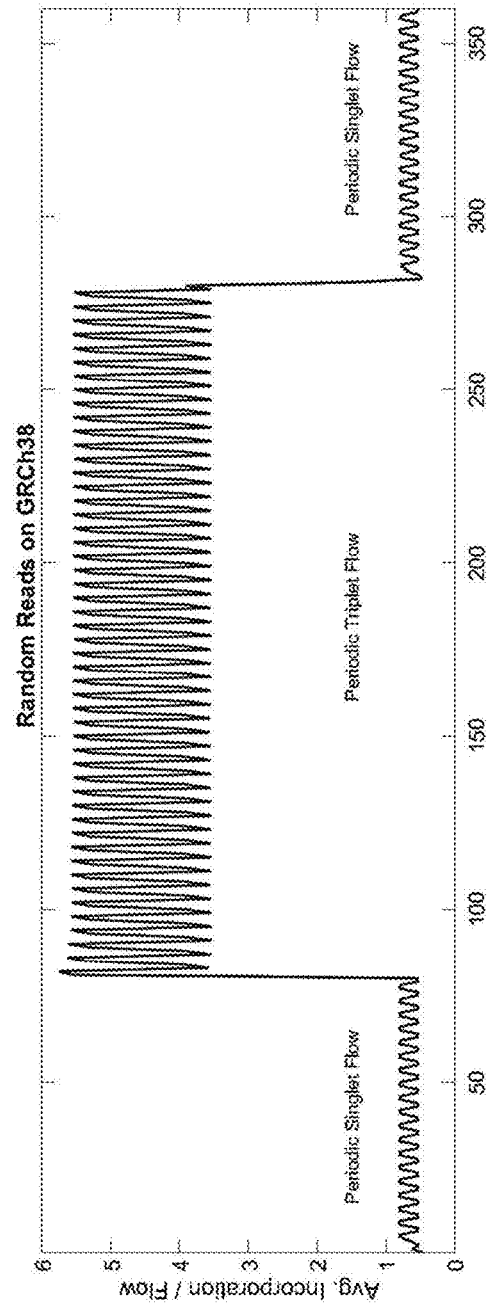
FIG. 25A shows average base incorporation across the flows in the first, second and third regions for a simulated fast-forward sequencing protocol using a repeated four-step flow cycle, wherein each flow includes a mixture of three different nucleotide bases. A matrix of variant base to reference base detection sensitivity is shown in FIG. 25B.
Figure 25B:
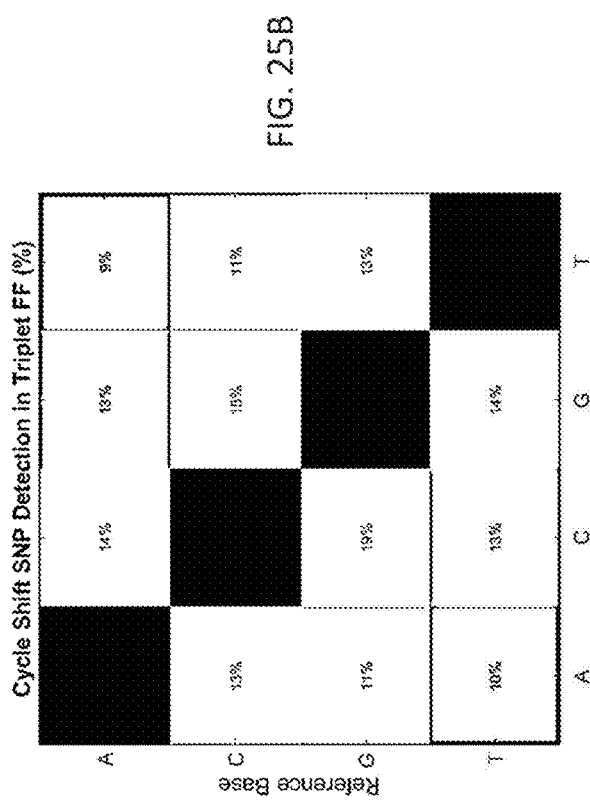
FIG. 25C shows the distribution of base coverage across the synthetic reads.
Figure 25C:
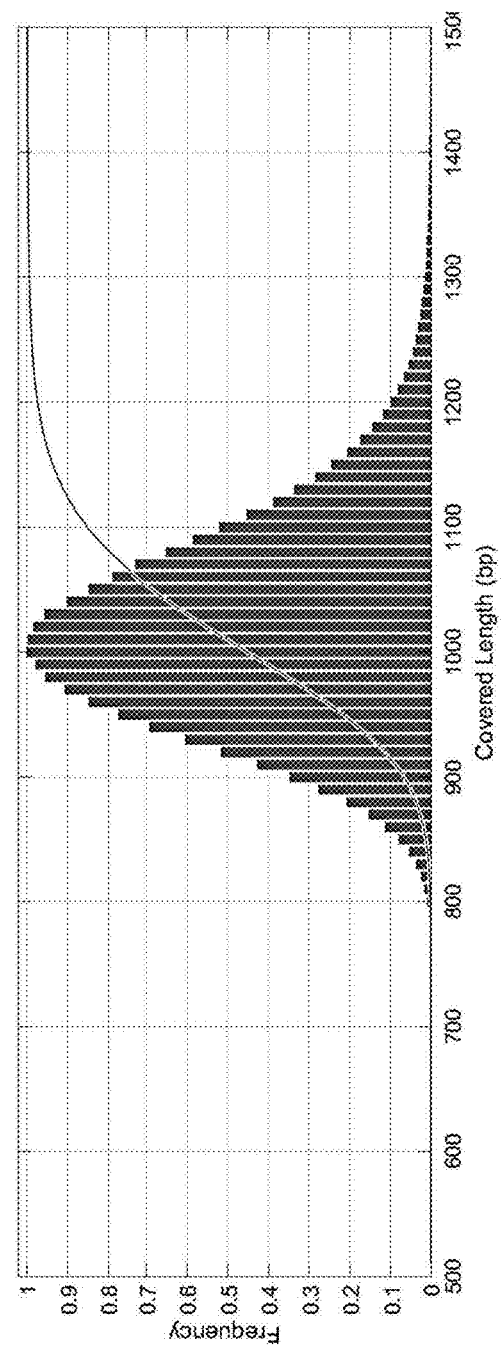

The synthetic nucleic acid molecules were then sequenced in silico using a four-step flow cycle, where each flow included a mixture of three nucleotides in a middle (second) region. The first regions of the synthetic nucleic acid molecules were sequenced using 80 nucleotide flows according to a four-step flow cycle, wherein each step included a single nucleotide base type. The sequencing primer extended across 54±7 bases in the 80 flows in the first region (~0.675 bases per flow). The second regions of the synthetic nucleic acid molecules were sequenced using 200 nucleotides according to a four-step flow cycle, wherein each step included three and omitted one nucleotide base type (i.e., (i) A, C, T, and not G; (ii) G, A, C, and not T; (iii) T, G, A, and not C; and (iv) C, T, G, and not A). The sequencing primer extended across 915±89 bases in the 200 flows in the second region (~4.575 bases per flow). The third regions of the synthetic nucleic acid molecules were sequenced using 80 nucleotide flows according to a four-step flow cycle, wherein each step included a single nucleotide base type. The sequencing primer extended across 54±7 bases in the 80 flows in the third region (~0.675 bases per flow). The flowgram of the third (downstream) region for each synthetic variant nucleic acid molecule was compared to the flowgram of the third region for a corresponding synthetic wild-type nucleic acid molecule. A new non-zero flowgram entry and/or a new zero flowgram entry in the third region of the synthetic variant nucleic acid molecule, compared to the corresponding synthetic wild-type nucleic acid molecule, indicated detection of the SNP introduced into the second region. FIG. 25A shows average base incorporation across the flows in the first, second and third regions. A matrix of variant base to reference base detection sensitivity is shown in FIG. 25B. FIG. 25C shows the distribution of base coverage across the synthetic reads.

Example 9

The effect of re-phasing using re-phasing flow steps having a mixture of two or three different nucleotide bases was studied using a simulated sequencing methodology. Approximately 10,000 synthetic sequencing reads, each 600 bp in length, were generated by random start-site selection from a human genome. In a control group, simulated flowgrams were generated by in silico sequencing of the synthetic sequencing reads using 105 rounds of a T-G-C-A flow cycle (420 total flows). The probability of lag phasing (i.e., a fraction of nucleotides that did not incorporate into an extending primer strand when the template indicated the nucleotide should have been incorporated per nucleotide correctly incorporated) was set to 0.2%, and the probability of lead phasing (i.e., a fraction of sequencing reads wherein an extra nucleotide was incorporated into the extending primer after each flow) was set to 0.5%. The average read length for the control group was 322 bp±18 bp.

Figure 26A:
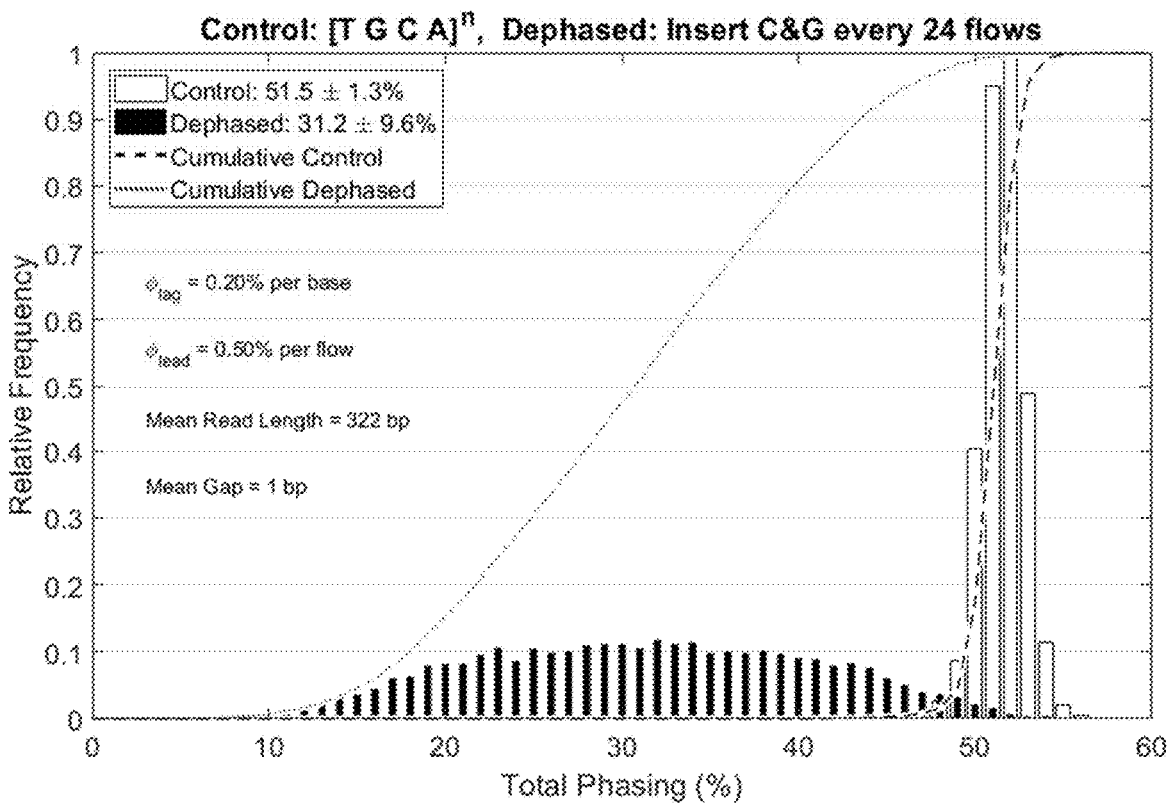
FIG. 26A shows the distribution of the sum of accumulated total phasing error (lag phasing error plus lead phasing error) over 10,000 simulated flowgrams for a control protocol (105 rounds of a T-G-C-A flow cycle) or a re-phasing protocol (105 rounds of a T-G-C-A flow cycle, wherein a re-phasing flow containing a mixture of C and G was used after every 24th flow). The mean and standard deviations are shown in the key. The integral of the distribution for the control and re-phasing protocols is also shown.
Figure 26B:
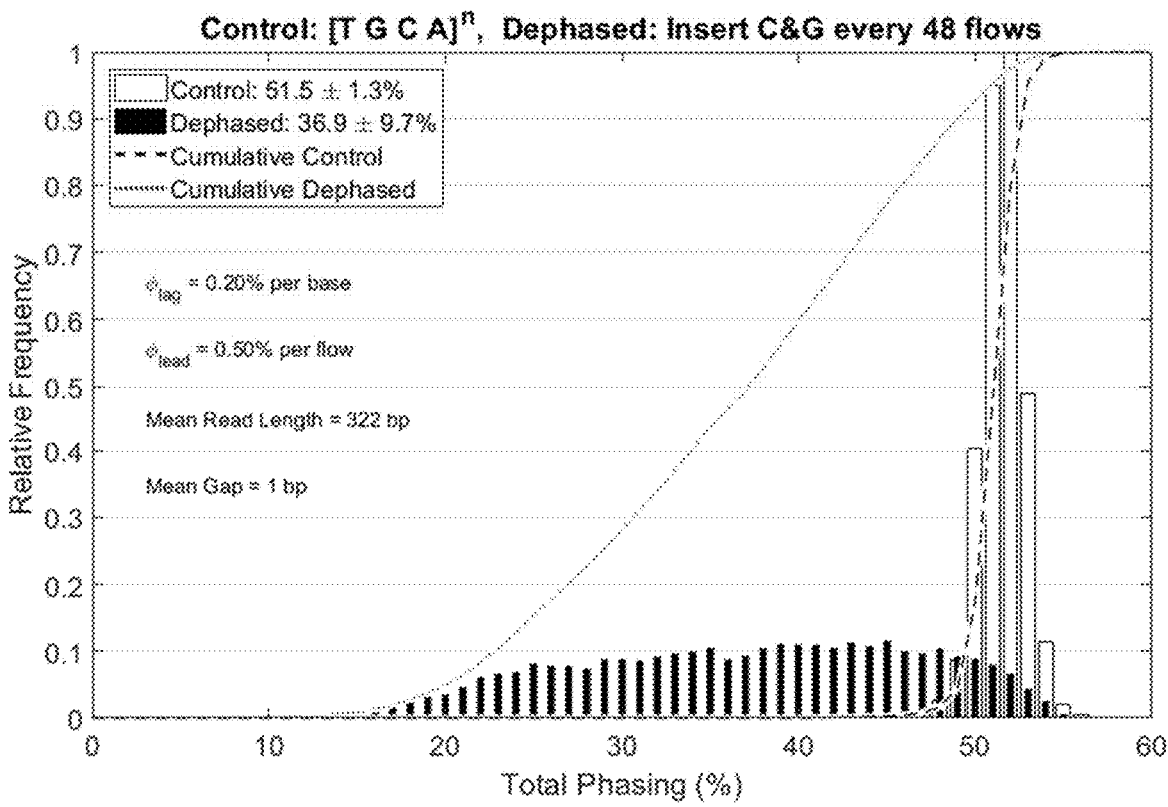
FIG. 26B shows the distribution of the sum of accumulated total phasing error (lag phasing error plus lead phasing error) over 10,000 simulated flowgrams for a control protocol (105 rounds of a T-G-C-A flow cycle) or a re-phasing protocol (105 rounds of a T-G-C-A flow cycle, wherein a re-phasing flow containing a mixture of C and G was used after every 48th flow). The mean and standard deviations are shown in the key. The integral of the distribution for the control and re-phasing protocols is also shown.
Figure 26C:
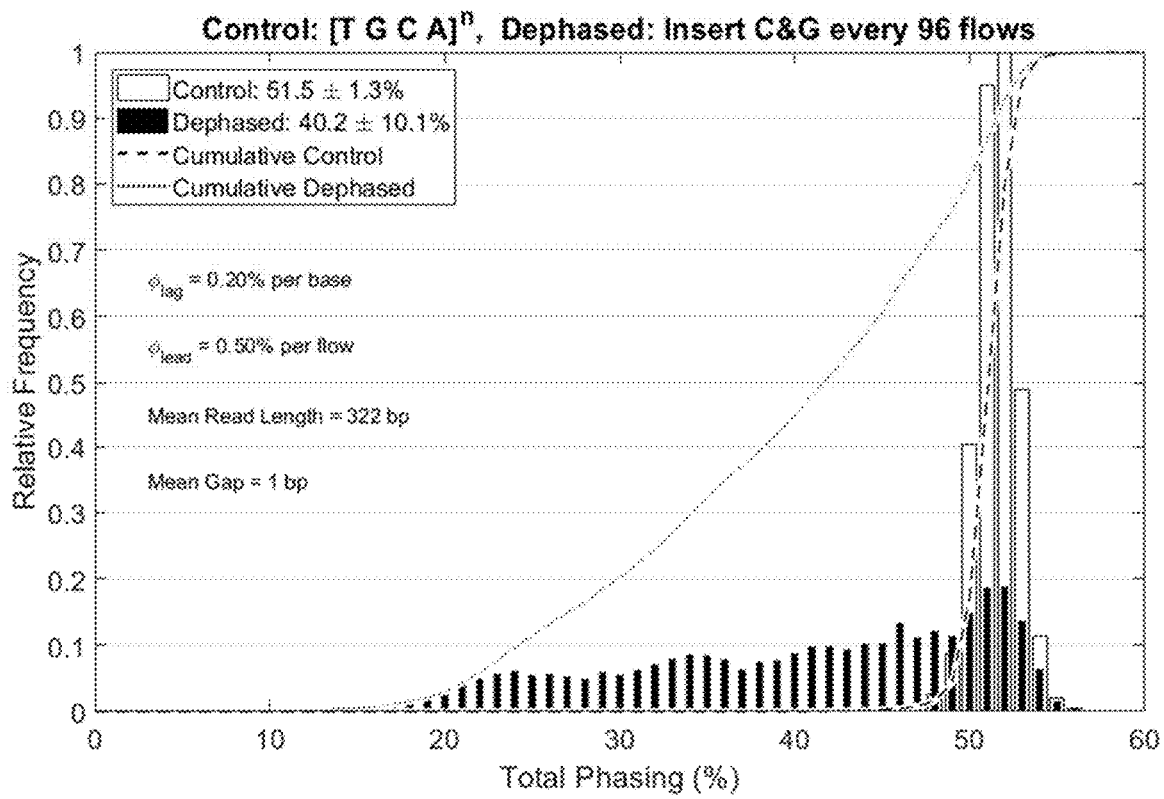
FIG. 26C shows the distribution of the sum of accumulated total phasing error (lag phasing error plus lead phasing error) over 10,000 simulated flowgrams for a control protocol (105 rounds of a T-G-C-A flow cycle) or a re-phasing protocol (105 rounds of a T-G-C-A flow cycle, wherein a re-phasing flow containing a mixture of C and G was used after every 96th flow). The mean and standard deviations are shown in the key. The integral of the distribution for the control and re-phasing protocols is also shown
Figure 26D:
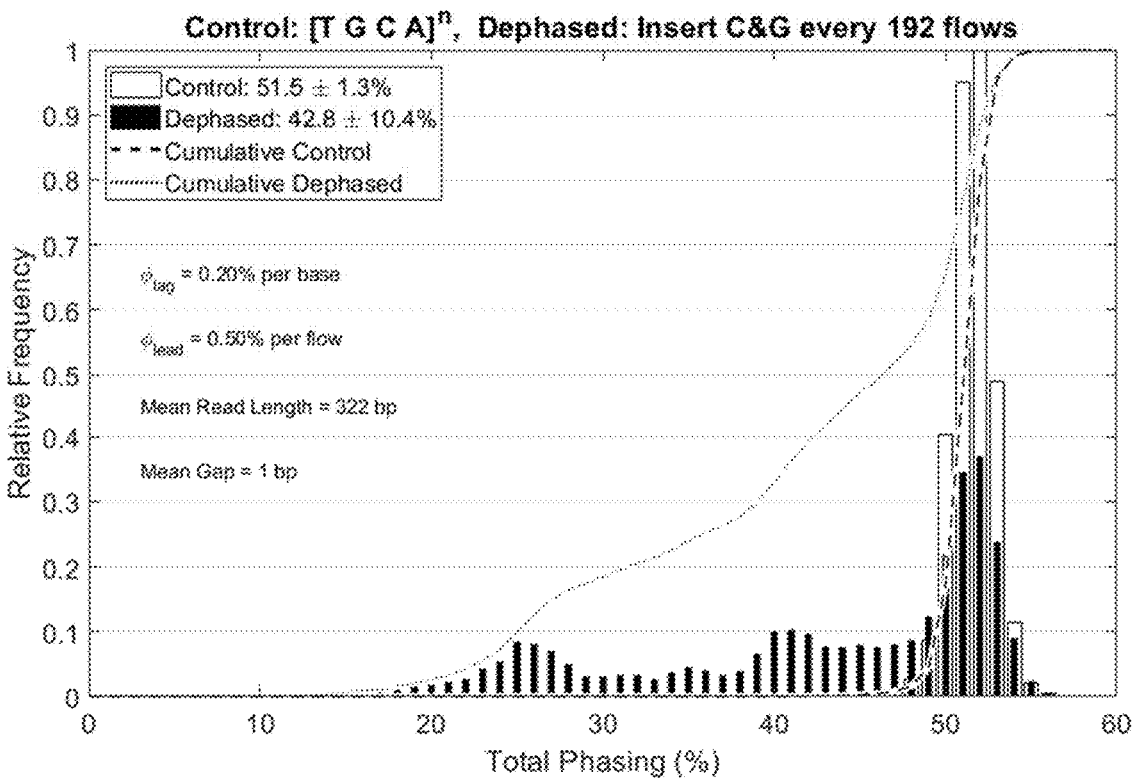
FIG. 26D shows the distribution of the sum of accumulated total phasing error (lag phasing error plus lead phasing error) over 10,000 simulated flowgrams for a control protocol (105 rounds of a T-G-C-A flow cycle) or a re-phasing protocol (105 rounds of a T-G-C-A flow cycle, wherein a re-phasing flow containing a mixture of C and G was used after every 192nd flow). The mean and standard deviations are shown in the key. The integral of the distribution for the control and re-phasing protocols is also shown
Figure 26E:
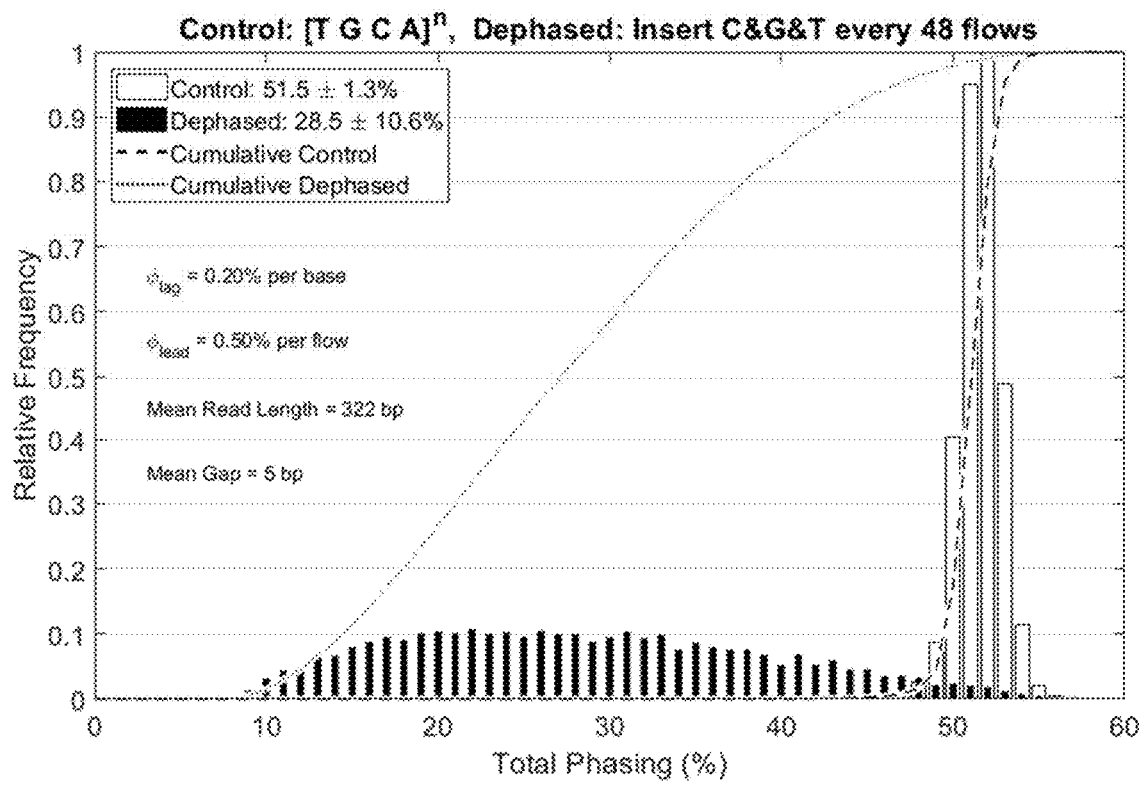
FIG. 26E shows the distribution of the sum of accumulated total phasing error (lag phasing error plus lead phasing error) over 10,000 simulated flowgrams for a control protocol (105 rounds of a T-G-C-A flow cycle) or a re-phasing protocol (105 rounds of a T-G-C-A flow cycle, wherein a re-phasing flow containing a mixture of C, G, and T was used after every 48th flow). The mean and standard deviations are shown in the key. The integral of the distribution for the control and re-phasing protocols is also shown.
Figure 26F:
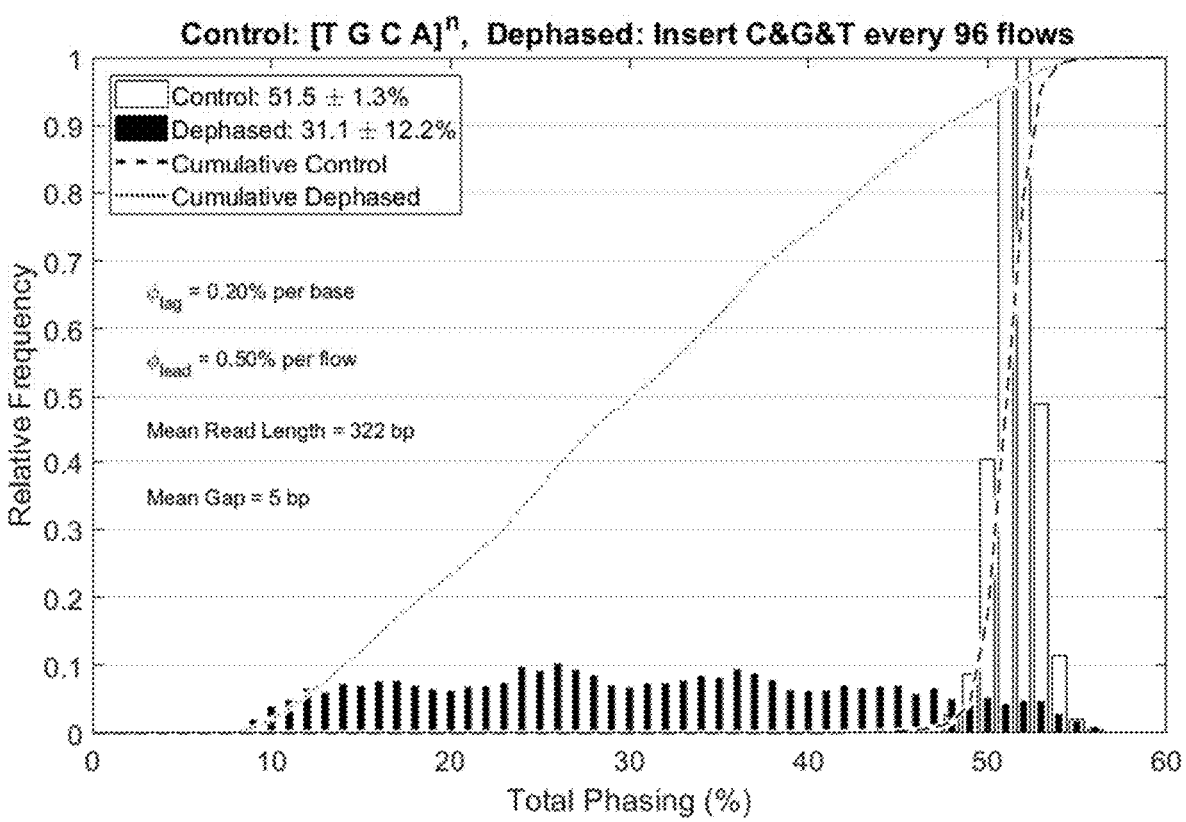
FIG. 26F shows the distribution of the sum of accumulated total phasing error (lag phasing error plus lead phasing error) over 10,000 simulated flowgrams for a control protocol (105 rounds of a T-G-C-A flow cycle) or a re-phasing protocol (105 rounds of a T-G-C-A flow cycle, wherein a re-phasing flow containing a mixture of C, G, and T was used after every 96th flow). The mean and standard deviations are shown in the key. The integral of the distribution for the control and re-phasing protocols is also shown.
Figure 26G:
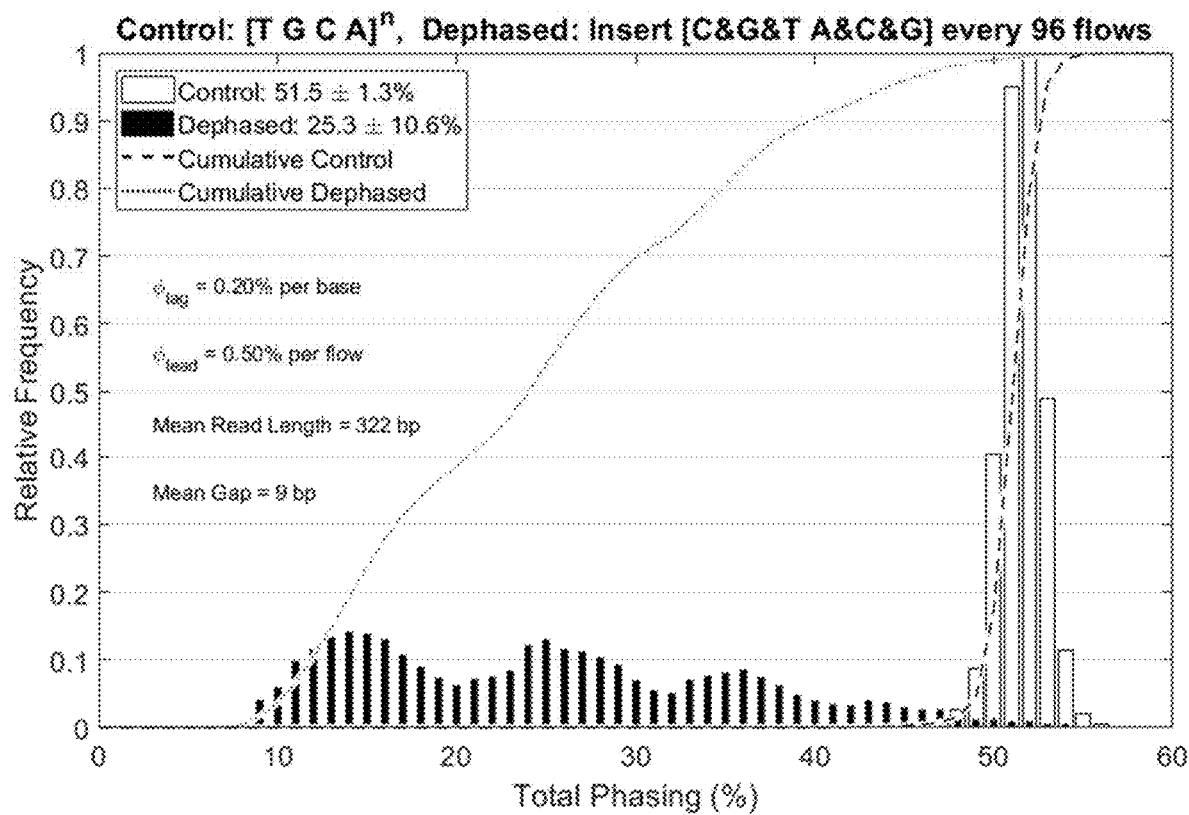
FIG. 26G shows the distribution of the sum of accumulated total phasing error (lag phasing error plus lead phasing error) over 10,000 simulated flowgrams for a control protocol (105 rounds of a T-G-C-A flow cycle) or a re-phasing protocol (105 rounds of a T-G-C-A flow cycle, wherein a first re-phasing flow containing a mixture of C, G, and T and a second re-phasing flow containing a mixture of A, C, and G was used after every 96th flow). The mean and standard deviations are shown in the key. The integral of the distribution for the control and re-phasing protocols is also shown.
Figure 26H:
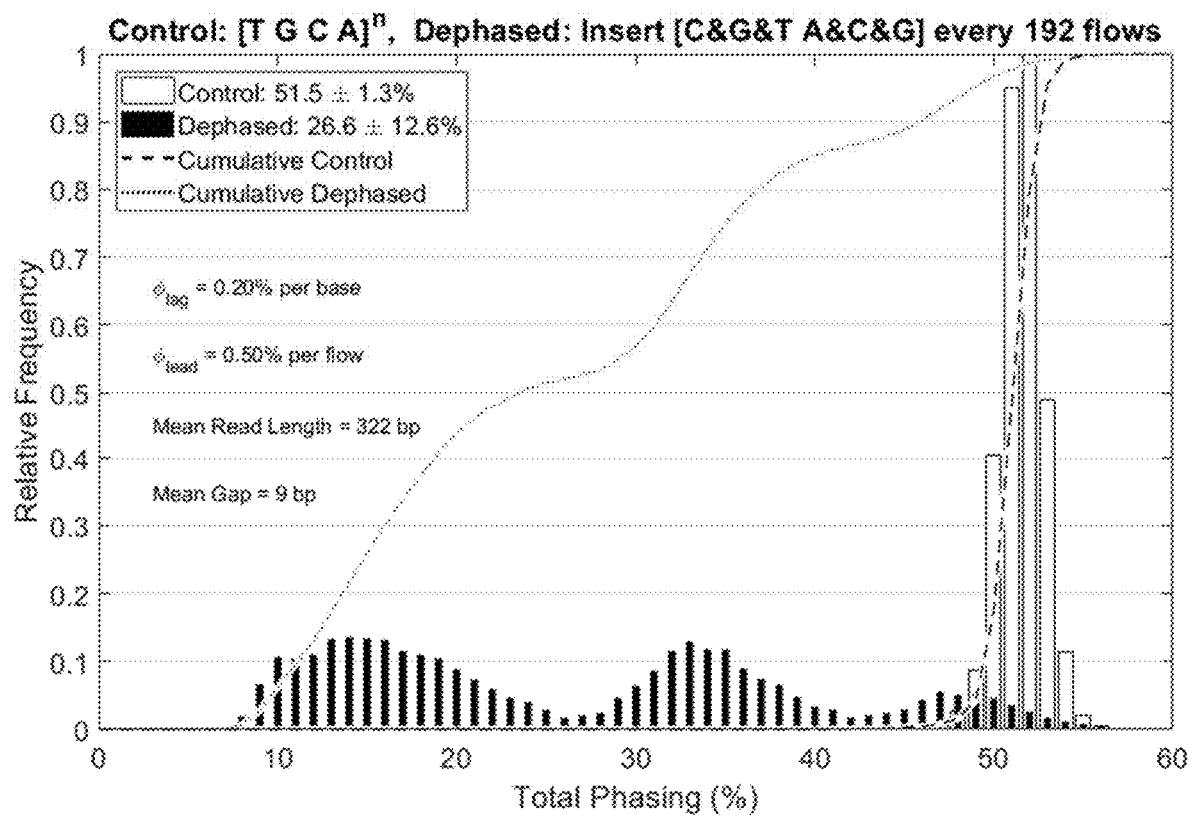
FIG. 26H shows the distribution of the sum of accumulated total phasing error (lag phasing error plus lead phasing error) over 10,000 simulated flowgrams for a control protocol (105 rounds of a T-G-C-A flow cycle) or a re-phasing protocol (105 rounds of a T-G-C-A flow cycle, wherein a first re-phasing flow containing a mixture of C, G, and T and a second re-phasing flow containing a mixture of A, C, and G was used after every 192nd flow). The mean and standard deviations are shown in the key. The integral of the distribution for the control and re-phasing protocols is also shown.
Figure 26I:
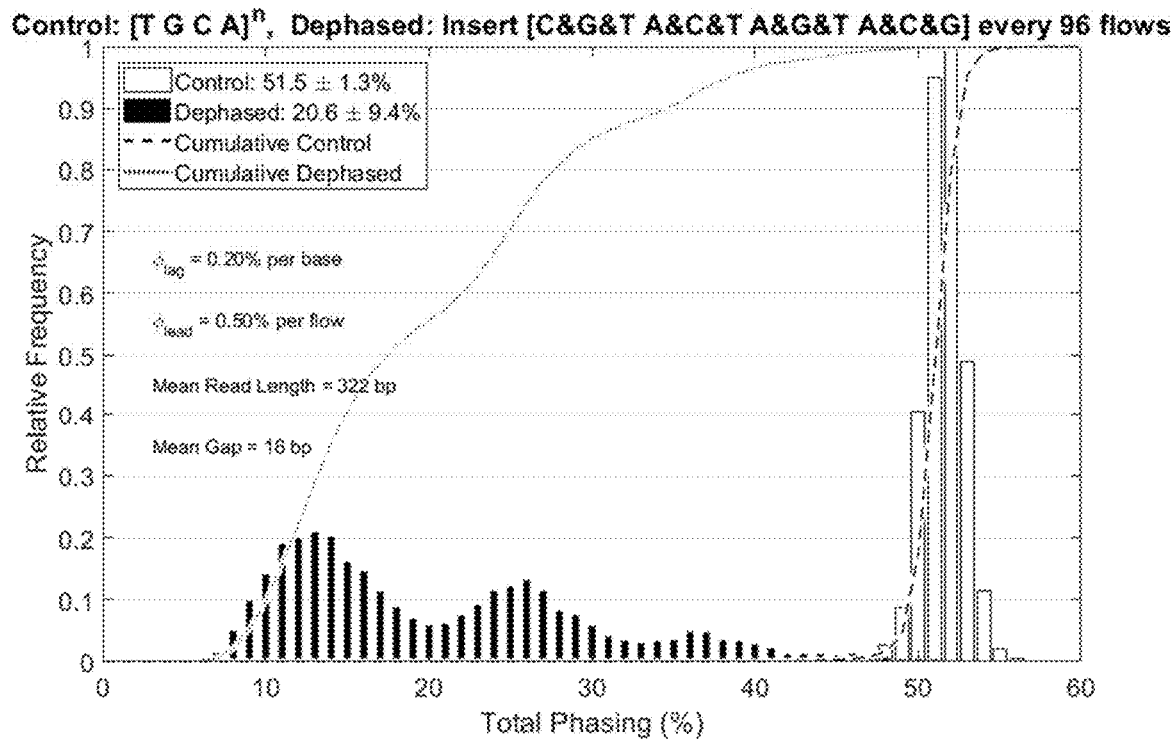
FIG. 26I shows the distribution of the sum of accumulated total phasing error (lag phasing error plus lead phasing error) over 10,000 simulated flowgrams for a control protocol (105 rounds of a T-G-C-A flow cycle) or a re-phasing protocol (105 rounds of a T-G-C-A flow cycle, wherein a f first re-phasing flow containing a mixture of C, G, and T, a second re-phasing flow containing a mixture of A, C, and T, a third re-phasing flow containing a mixture of A, G, and T, and a fourth rephrasing flow containing a mixture of A, C, and G was used after every 96th flow). The mean and standard deviations are shown in the key. The integral of the distribution for the control and re-phasing protocols is also shown.
Figure 26J:
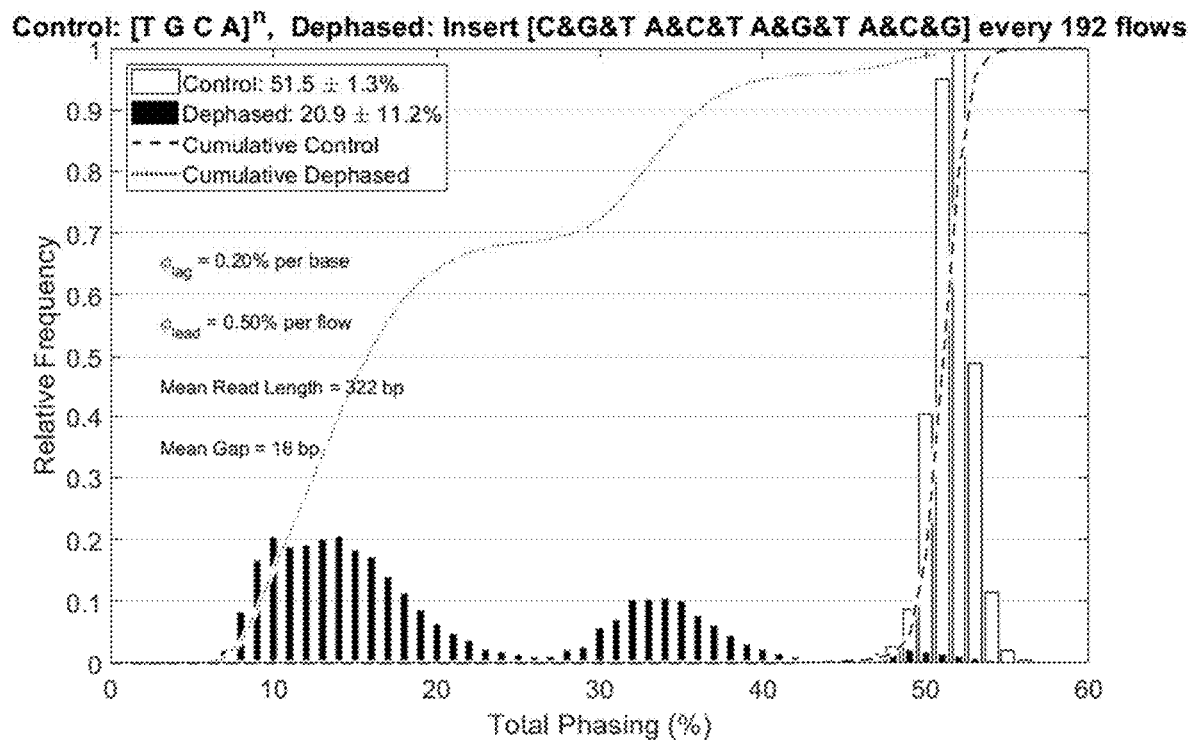
FIG. 26J shows the distribution of the sum of accumulated total phasing error (lag phasing error plus lead phasing error) over 10,000 simulated flowgrams for a control protocol (105 rounds of a T-G-C-A flow cycle) or a re-phasing protocol (105 rounds of a T-G-C-A flow cycle, wherein a f first re-phasing flow containing a mixture of C, G, and T, a second re-phasing flow containing a mixture of A, C, and T, a third re-phasing flow containing a mixture of A, G, and T, and a fourth rephrasing flow containing a mixture of A, C, and G was used after every 192nd flow). The mean and standard deviations are shown in the key. The integral of the distribution for the control and re-phasing protocols is also shown

In a series of test groups, simulated flowgrams were generated by in silico sequencing of the synthetic sequencing reads using 105 rounds of a T-G-C-A flow cycle (420 total flows), except for one of the following conditions: (1) after every 24th flow, a re-phasing flow containing a mixture of C and G was inserted (FIG. 26A); (2) after every 48th flow, a re-phasing flow containing a mixture of C and G was inserted (FIG. 26B); (3) after every 96th flow, a re-phasing flow containing a mixture of C and G was inserted (FIG. 26C); (4) after every 192nd flow, a re-phasing flow containing a mixture of C and G was inserted (FIG. 26D); (5) after every 48th flow, a re-phasing flow containing a mixture of C, G, and T was inserted, followed by a single A flow (to avoid redundant flow) before reverting back to the T-G-C-A cycle according to the control protocol (FIG. 26E); (6) after every 96th flow, a re-phasing flow containing a mixture of C, G, and T was inserted, followed by a single A flow (to avoid redundant flow) before reverting back to the T-G-C-A cycle according to the control protocol (FIG. 26F); (7) after every 96th flow, a re-phasing flow containing a mixture of C, G, and T was inserted, followed by a re-phasing flow containing a mixture of A, C, and G (FIG. 26G); (8) after every 192nd flow, a re-phasing flow containing a mixture of C, G, and T was inserted, followed by a re-phasing flow containing a mixture of A, C, and G (FIG. 26H); (9) after every 96th flow, a re-phasing flow containing a mixture of C, G, and T was inserted, followed by a re-phasing flow containing a mixture of A, C, and T, followed by a re-phasing flow containing a mixture of A, G, and T followed by a re-phasing flow containing a mixture of A, C, and G (FIG. 26I); or (10) after every 192nd flow, a re-phasing flow containing a mixture of C, G, and T was inserted, followed by a re-phasing flow containing a mixture of A, C, and T, followed by a re-phasing flow containing a mixture of A, G, and T followed by a re-phasing flow containing a mixture of A, C, and G (FIG. 26J).

The use of any of the tested re-phasing flows resulted in a substantial decrease in total phasing error (i.e., the sum of the fraction of strands having a lag phasing error and the fraction of strands having a lead phasing error, relative to a nominally sequenced strand where no lag or lead error was introduced) after the full round of in silico sequencing, compared to the control, with minimal loss of sequencing data. FIGS. 26A-26J show the distribution of the sum of total phasing error for the control protocol and each respective re-phasing flow protocol. Using a re-phasing flow containing a mixture of C and G after every 24th flow reduced the mean total accumulated phasing error to 31.2±9.6% (compared to 51.5±1.3% control) (FIG. 26A), after every 48th flow reduced the mean total accumulated phasing error to 36.9±9.7% (FIG. 26B), after every 96th flow reduced the mean total accumulated phasing error to 40.2±10.1% (FIG. 26C), and after every 192nd flow reduced the mean total accumulated phasing error to 42.8±10.4% (FIG. 26D), while only generating a ~1 bp mean primer extension (i.e., sequencing gap) per re-phasing flow. Using a re-phasing flow containing a mixture of C, G, and T after every 48th flow reduced the mean total accumulated phasing error to 28.5±10.6% (FIG. 26E), and after every 96th flow reduced the mean total accumulated phasing error to 31.1±12.2% (FIG. 26F), while only generating a ~5 bp mean primer extension per re-phasing flow. Using a first re-phasing flow containing a mixture of C, G, and T and a second re-phasing flow containing a mixture of A, C, and G after every 96th flow reduced the mean total accumulated phasing error to 25.3±10.6% (FIG. 26G), and after every 192nd flow reduced the mean total accumulated phasing error to 26.6±12.6% (FIG. 26H), while only generating a ~9 bp mean primer extension per re-phasing doublet flow. Using a first re-phasing flow containing a mixture of C, G, and T, a second re-phasing flow containing a mixture of A, C, and T, a third re-phasing flow containing a mixture of A, G, and T, and a fourth rephrasing flow containing a mixture of A, C, and G after every 96th flow reduced the mean total accumulated phasing error to 20.6±9.4% (FIG. 26I), and after every 192nd flow reduced the mean total accumulated phasing error to 20.9±11.2% (FIG. 26J), while only generating ~18 bp mean primer extension per re-phasing quadruplet flow.

What is claimed is:

1. A method of synchronizing sequencing primers within a sequencing cluster, comprising:
   hybridizing primers to polynucleotide copies within a sequencing cluster;
   extending the primers through a first region of the polynucleotide copies using a mixture of labeled and unlabeled nucleotides according to a first region flow cycle;
   extending the primers through a second region of the polynucleotide copies using one or more re-phasing flows without detecting incorporation of nucleotides into the primers during the one or more re-phasing flows, wherein a mixture of at least two different types of nucleotide bases is used in each of the one or more re-phasing flows; and
   extending the primers through a third region of the polynucleotide copies using labeled nucleotides according to a third region flow cycle, wherein only a single type of nucleotide base is used at a time during a flow of the third region flow cycle.

2. The method of claim 1, wherein a mixture of three different types of nucleotide bases are used in at least one of the one or more re-phasing flows.

3. The method of claim 1, wherein a mixture of three different types of nucleotide bases are used in each of the one or more re-phasing flows.

4. The method of claim 1, wherein the one or more re-phasing flows comprises four or more flow steps.

5. The method of claim 4, wherein a mixture of three different types of nucleotide bases are used in at least one of the one or more re-phasing flows.

6. The method of claim 5, wherein a mixture of three different types of nucleotide bases are used in each of the one or more re-phasing flows.

7. The method of claim 4, wherein the one or more re-phasing flows comprises, in any order:
   (i) a first flow comprising a mixture comprising A, C, and G nucleotides and omitting T nucleotides;
   (ii) a second flow comprising a mixture comprising T, C, and G nucleotides and omitting A nucleotides;
   (iii) a third flow comprising a mixture comprising T, A, and G nucleotides and omitting C nucleotides; and
   (iv) a fourth flow comprising a mixture comprising T, A, and C nucleotides and omitting G nucleotides.

8. The method of claim 1, wherein the one or more re-phasing flows comprises one or more of, in any order, (i) a flow comprising a mixture comprising A and C nucleotides and omitting G and T nucleotides; (ii) a flow comprising a mixture comprising T and G nucleotides, and omitting A and C nucleotides; (iii) a flow comprising a mixture comprising A and G nucleotides and omitting T and C nucleotides; (iv) a flow comprising a mixture comprising T and C nucleotides and omitting A and G nucleotides; (v) a flow comprising a mixture comprising A and T nucleotides and omitting G and C nucleotides; (vi) a flow comprising a mixture comprising C and G nucleotides and omitting A and T nucleotides; (vii) a flow comprising a mixture comprising A, G, and C nucleotides and omitting T nucleotides; (viii) a flow comprising a mixture comprising T, A, and G nucleotides and omitting C nucleotides; (ix) a flow comprising a mixture comprising C, T, and A nucleotides and omitting G nucleotides; or (x) a flow step comprising a mixture of G, C, and T nucleotides and omitting A nucleotides.

9. The method of claim 1, wherein at least one of the one or more re-phasing flows comprises a mixture of A, C, G, and T nucleotides, wherein three base types are non-terminating nucleotides and one base type comprises a reversible terminator.

10. The method of claim 9, wherein the one or more re-phasing flows comprises (i) a flow comprising a mixture comprising non-terminating A nucleotides, non-terminating C nucleotides, non-terminating G nucleotides, and T nucleotides comprising a reversible terminator; (ii) a flow comprising a mixture comprising non-terminating T nucleotides, non-terminating A nucleotides, non-terminating C nucleotides, and G nucleotides comprising a reversible terminator; (iii) a flow comprising a mixture comprising non-terminating G nucleotides, non-terminating T nucleotides, non-terminating A nucleotides, and C nucleotides comprising a reversible terminator; or (iv) a flow comprising a mixture comprising non-terminating C nucleotides, non-terminating G nucleotides, non-terminating T nucleotides, and A nucleotides comprising a reversible terminator.

11. The method of claim 1, comprising generating sequencing data associated with a sequence of the first region by detecting the presence or absence of an incorporated labeled nucleotide while extending the primers through the first region.

12. The method of claim 11, comprising generating sequencing data associated with a sequence of the third region by detecting the presence or absence of an incorporated labeled nucleotide while extending the primers through the third region.

13. The method of claim 1, comprising generating sequencing data associated with a sequence of the third region by detecting the presence or absence of an incorporated labeled nucleotide while extending the primers through the third region.

14. The method of claim 1, wherein at least a portion of the nucleotides used to extend the primers through the second region are unlabeled nucleotides.

15. The method of claim 1, wherein the nucleotides used to extend the primers through the second region are unlabeled nucleotides.

16. The method of claim 1, wherein the sequencing cluster is attached to a bead or a flowcell.

17. The method of claim 1, wherein the polynucleotide copies within the sequencing cluster are substantially identical to each other.

18. The method of claim 1, wherein the sequencing cluster is formed by bridge amplification or emulsion PCR.

19. The method of claim 1, wherein the sequencing cluster is formed on a bead by emulsion PCR, and wherein the bead is further attached to a surface.

\* \* \* \* \*

SEQUENCE LISTING

```
Sequence total quantity: 22
SEQ ID NO: 1                moltype = DNA  length = 30
FEATURE                     Location/Qualifiers
misc_feature                1..30
                            note = Synthetic Construct
source                      1..30
                            mol_type = other DNA
                            organism = synthetic construct
SEQUENCE: 1
cagtcgacgt ccgtatagcc taagttcagt                                           30

SEQ ID NO: 2                moltype =   length =
SEQUENCE: 2
000

SEQ ID NO: 3                moltype =   length =
SEQUENCE: 3
000

SEQ ID NO: 4                moltype = DNA  length = 30
FEATURE                     Location/Qualifiers
misc_feature                1..30
                            note = Synthetic Construct
source                      1..30
                            mol_type = other DNA
                            organism = synthetic construct
SEQUENCE: 4
cagtcgacgt ccgtatagtc taagttcagt                                           30

SEQ ID NO: 5                moltype =   length =
SEQUENCE: 5
000

SEQ ID NO: 6                moltype =   length =
SEQUENCE: 6
000

SEQ ID NO: 7                moltype =   length =
SEQUENCE: 7
000

SEQ ID NO: 8                moltype = DNA  length = 33
FEATURE                     Location/Qualifiers
misc_feature                1..33
                            note = Synthetic Construct
source                      1..33
                            mol_type = other DNA
                            organism = synthetic construct
SEQUENCE: 8
cagtcgacta cgtccgtata gcctaagttc agt                                       33

SEQ ID NO: 9                moltype = DNA  length = 23
FEATURE                     Location/Qualifiers
misc_feature                1..23
                            note = Synthetic Construct
source                      1..23
                            mol_type = other DNA
                            organism = synthetic construct
SEQUENCE: 9
cagtcgtata gcctaagttc agt                                                  23

SEQ ID NO: 10               moltype =   length =
SEQUENCE: 10
000

SEQ ID NO: 11               moltype =   length =
SEQUENCE: 11
000

SEQ ID NO: 12               moltype = DNA  length = 30
FEATURE                     Location/Qualifiers
misc_feature                1..30
                            note = Synthetic Construct
source                      1..30
                            mol_type = other DNA
                            organism = synthetic construct
SEQUENCE: 12
cagtcggcct gcatatagcc taagttcagt                                           30
```

```
SEQ ID NO: 13           moltype =    length =
SEQUENCE: 13
000

SEQ ID NO: 14           moltype =    length =
SEQUENCE: 14
000

SEQ ID NO: 15           moltype = DNA   length = 12
FEATURE                 Location/Qualifiers
misc_feature            1..12
                        note = Synthetic Construct
source                  1..12
                        mol_type = other DNA
                        organism = synthetic construct
SEQUENCE: 15
tatggtcgtc ga                                                          12

SEQ ID NO: 16           moltype = DNA   length = 12
FEATURE                 Location/Qualifiers
misc_feature            1..12
                        note = Synthetic Construct
source                  1..12
                        mol_type = other DNA
                        organism = synthetic construct
SEQUENCE: 16
tatggtcatc ga                                                          12

SEQ ID NO: 17           moltype = DNA   length = 12
FEATURE                 Location/Qualifiers
misc_feature            1..12
                        note = Synthetic Construct
source                  1..12
                        mol_type = other DNA
                        organism = synthetic construct
SEQUENCE: 17
tggtcgtcga gc                                                          12

SEQ ID NO: 18           moltype = DNA   length = 12
FEATURE                 Location/Qualifiers
misc_feature            1..12
                        note = Synthetic Construct
source                  1..12
                        mol_type = other DNA
                        organism = synthetic construct
SEQUENCE: 18
tatatggtcg tc                                                          12

SEQ ID NO: 19           moltype = DNA   length = 19
FEATURE                 Location/Qualifiers
misc_feature            1..19
                        note = Synthetic Construct
source                  1..19
                        mol_type = other DNA
                        organism = synthetic construct
SEQUENCE: 19
tatatggtca tcgagctat                                                   19

SEQ ID NO: 20           moltype = DNA   length = 19
FEATURE                 Location/Qualifiers
misc_feature            1..19
                        note = Synthetic Construct
source                  1..19
                        mol_type = other DNA
                        organism = synthetic construct
SEQUENCE: 20
tatatggtcg tcgagctat                                                   19

SEQ ID NO: 21           moltype = DNA   length = 12
FEATURE                 Location/Qualifiers
misc_feature            1..12
                        note = Synthetic Construct
source                  1..12
                        mol_type = other DNA
                        organism = synthetic construct
SEQUENCE: 21
tatggtcgtc ga                                                          12
```

```
SEQ ID NO: 22          moltype = DNA   length = 12
FEATURE                Location/Qualifiers
misc_feature           1..12
                       note = Synthetic Construct
source                 1..12
                       mol_type = other DNA
                       organism = synthetic construct
SEQUENCE: 22
tatggtcgat cg                                                                  12
```